(12) United States Patent
Delgoffe et al.

(10) Patent No.: US 11,786,569 B2
(45) Date of Patent: Oct. 17, 2023

(54) EXPRESSION OF METABOLIC MODULATORS IN TUMOR MICROENVIRONMENT TO IMPROVE TUMOR THERAPY

(71) Applicant: University of Pittsburgh—Of the Commonwealth System of Higher Education, Pittsburgh, PA (US)

(72) Inventors: Greg M. Delgoffe, Pittsburgh, PA (US); Dayana Rivadeneira, Pittsburgh, PA (US); Padmavathi Sampath, Pittsburgh, PA (US); Stephen H. Thorne, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 471 days.

(21) Appl. No.: 16/959,025

(22) PCT Filed: Jan. 28, 2019

(86) PCT No.: PCT/US2019/015434
§ 371 (c)(1),
(2) Date: Jun. 29, 2020

(87) PCT Pub. No.: WO2019/148109
PCT Pub. Date: Aug. 1, 2019

(65) Prior Publication Data
US 2020/0330534 A1    Oct. 22, 2020

Related U.S. Application Data

(60) Provisional application No. 62/622,547, filed on Jan. 26, 2018.

(51) Int. Cl.
| | |
|---|---|
| *A61K 38/00* | (2006.01) |
| *A61K 35/763* | (2015.01) |
| *A61P 35/00* | (2006.01) |
| *A61K 35/768* | (2015.01) |
| *C07K 14/495* | (2006.01) |
| *C07K 14/54* | (2006.01) |
| *C07K 14/545* | (2006.01) |
| *C07K 14/55* | (2006.01) |
| *C07K 14/56* | (2006.01) |
| *C07K 14/57* | (2006.01) |
| *C07K 14/575* | (2006.01) |
| *C12N 7/00* | (2006.01) |
| *A61K 45/06* | (2006.01) |

(52) U.S. Cl.
CPC .......... *A61K 35/763* (2013.01); *A61K 35/768* (2013.01); *A61P 35/00* (2018.01); *C07K 14/495* (2013.01); *C07K 14/545* (2013.01); *C07K 14/5406* (2013.01); *C07K 14/5418* (2013.01); *C07K 14/5425* (2013.01); *C07K 14/5428* (2013.01); *C07K 14/5437* (2013.01); *C07K 14/5443* (2013.01); *C07K 14/55* (2013.01); *C07K 14/56* (2013.01); *C07K 14/57* (2013.01); *C07K 14/5759* (2013.01); *C12N 7/00* (2013.01); *A61K 45/06* (2013.01)

(58) Field of Classification Search
CPC .... A61K 35/768; A61K 38/00; C07K 14/495; C07K 14/5759; A61P 35/00; C12N 7/00; C12N 15/76
See application file for complete search history.

(56) References Cited

U.S. PATENT DOCUMENTS

| | | |
|---|---|---|
| 2006/0099188 A1 | 5/2006 | Tagawa |
| 2011/0256123 A1 | 10/2011 | Ilan et al. |
| 2012/0114612 A1 | 5/2012 | Evans et al. |

FOREIGN PATENT DOCUMENTS

| | | |
|---|---|---|
| JP | 2017-522025 | 8/2017 |
| WO | WO 2009/065547 | 5/2009 |
| WO | WO 2016/008976 A1 | 1/2016 |
| WO | WO 2017/043815 A1 | 3/2017 |

OTHER PUBLICATIONS

Samad, Biomed J Sci & Tech Res 18(1)-2019.*
Borysiewicz et al., Lancet, 1996, 347, 1523-27.*
de Gruijl et al., "Arming oncolytic viruses to leverage antitumor immunity," *Expert Opinion of Biological Therapy*, vol. 15, No. 7, pp. 959-971, 2015.
Liu et al., "Rational combination of oncolytic vaccinia virus and PD-L1 blockade works synergistically to enhance therapeutic efficacy," *Nature Communications*, vol. 8, Article No. 14754 (12 pages), 2017.
Morsy et al., "An adenoviral vector deleted for all viral coding sequences results in enhanced safety and extended expression of a leptin transgene," *Proceedings of the National Academy of Sciences*, vol. 95, pp. 7866-7871, 1998.
Suryawanshi et al., "Oncolytic viruses: emerging options for the treatment of breast cancer," *Medical Oncology*, vol. 34, Article No. 43 (11 pages), 2017.
Rivadeneira et al., "Fueling antitumor immunity using oncolytic viruses encoding metabolic modulators," 33rd Annual Meeting & Pre-Conference Programs of The Society for Immunotherapy of Cancer (SITC 2018), Poster 616, *Journal for ImmunoTherapy of Cancer*, 6(Suppl 1), pp. 332-333, 2018.

(Continued)

*Primary Examiner* — Jeanette M Lieb
(74) *Attorney, Agent, or Firm* — Klarquist Sparkman, LLP

(57) ABSTRACT

Recombinant oncolytic viruses (OVs) that express one or more metabolic modulator proteins, such as an adipokine (e.g., leptin or chemerin), insulin, and/or IGF-1, and methods of their use to treat cancer, for example in immunotherapy anti-cancer treatments. In some examples, such recombinant OVs and methods increase T cell infiltration into the tumor or tumor microenvironment.

20 Claims, 33 Drawing Sheets
Specification includes a Sequence Listing.

(56) References Cited

OTHER PUBLICATIONS

Watanabe et al., "Oncolytic Adenovirus Expressing Cytokines Enhances Anti-Tumor Efficacy of Mesothelin-Redirected CAR-T Cells," *Blood*, 128 (22): 3360 (6 pages), 2016.
Fountzilas et al., "Review: Oncolytic virotherapy, updates and future directions," *Oncotarget* 8:102617-39, 2017.
Guo et al., "Oncolyte Immunotherapy: Conceptual Evolution, Current Strategies, and Futures Perspectives," *Front. Immunol.* 8:555, 2017 (15 pages).
Jhawar et al., "Oncolytic Viruses—Natural and Genetically Engineered Cancer Immunotherapies," *Front. Immunol.* 7:202, 2017 (11 pages).
Rivadeneira et al., "Oncolyte Viruses Engineered to Enforce Leptin Expression Reprogram Tumor-Infiltrating T Cell Metabolism and Promote Tumor Clearance," *Immunity. 51*:548-560, 2019.
PCT/US2019/015434 Written Opinion and International Search Report dated Apr. 15, 2019 (8 pages).

\* cited by examiner

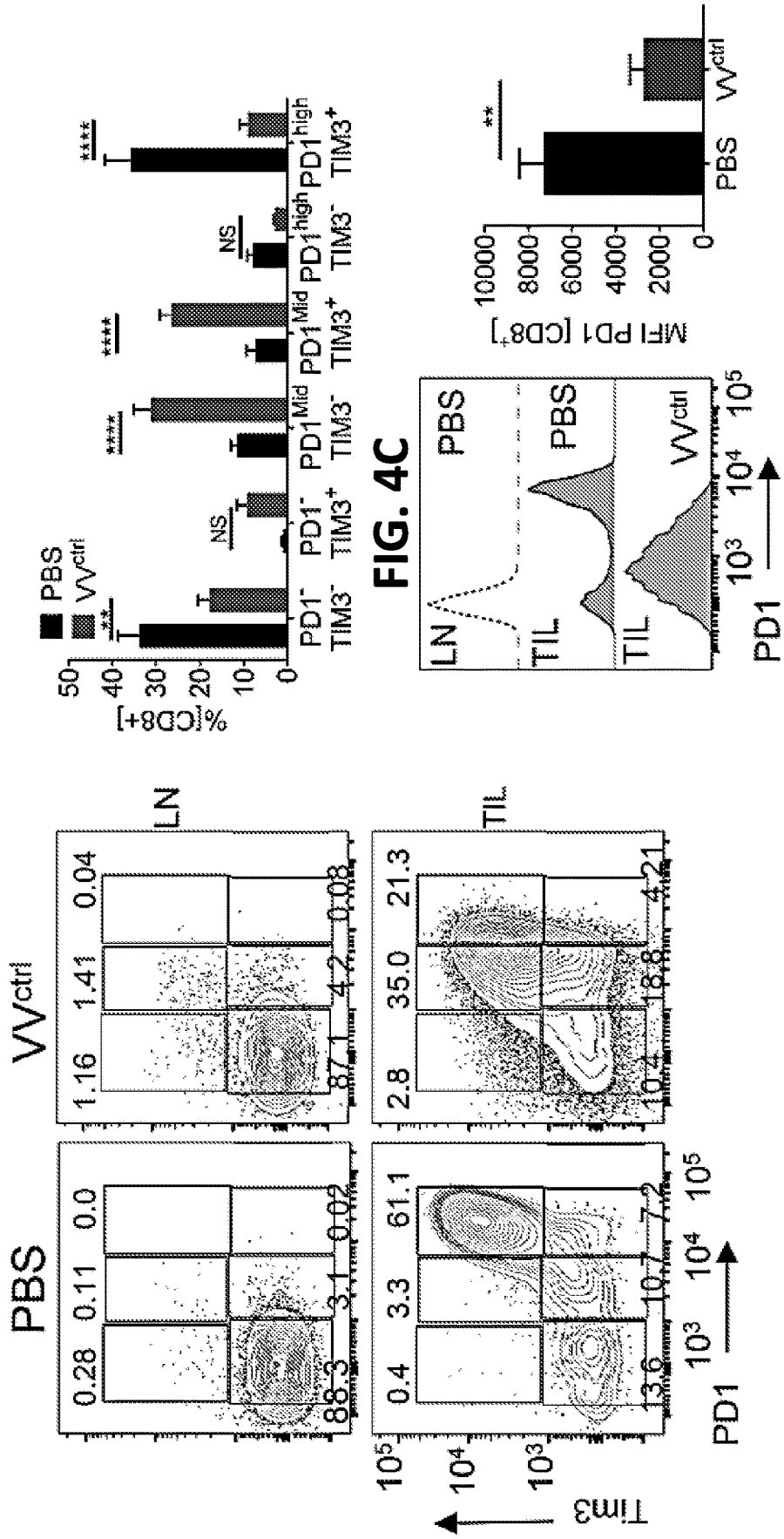

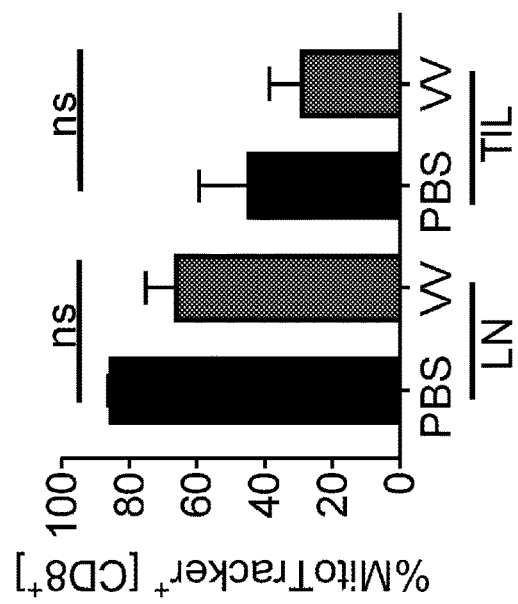
FIG. 4D
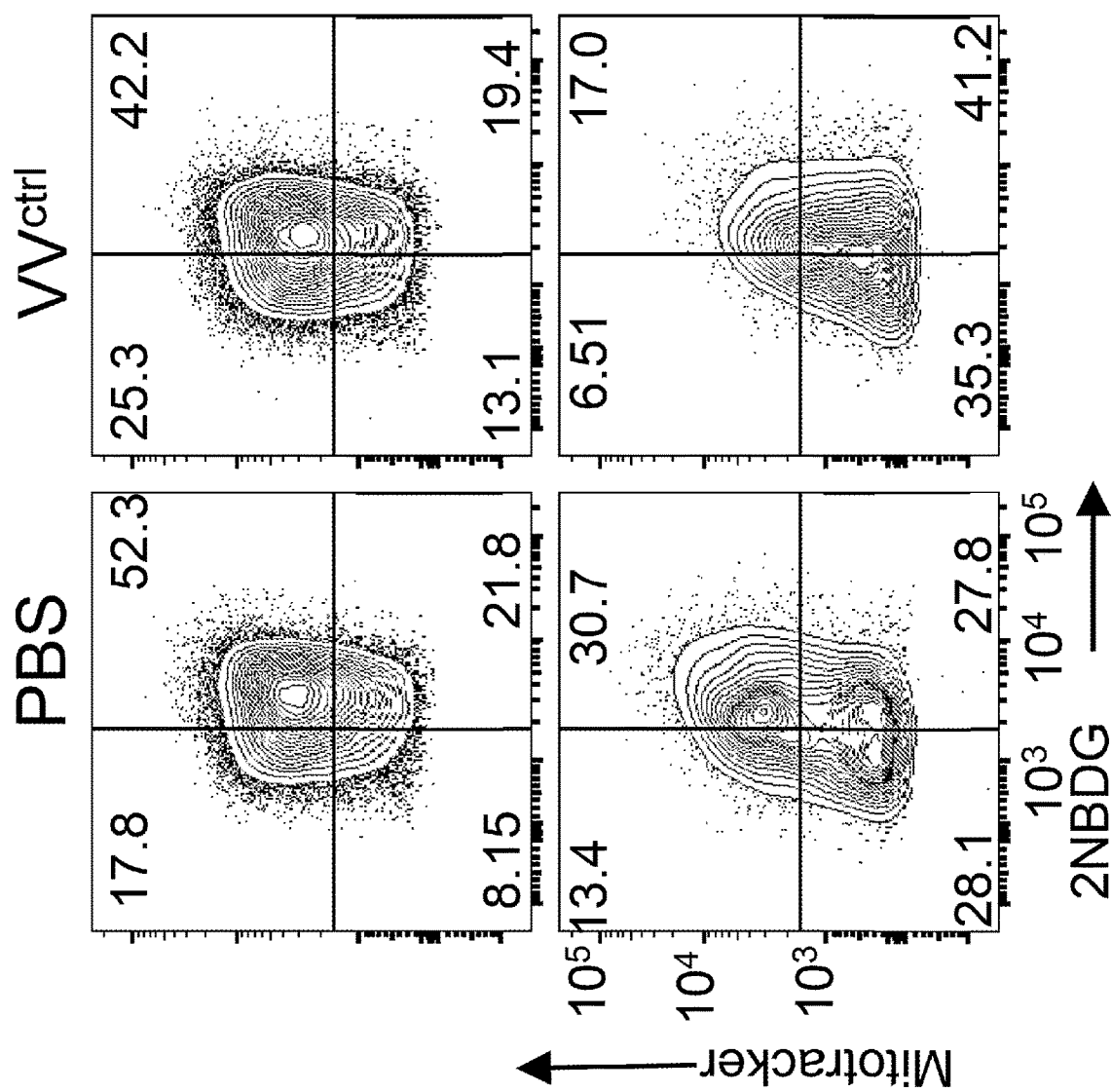

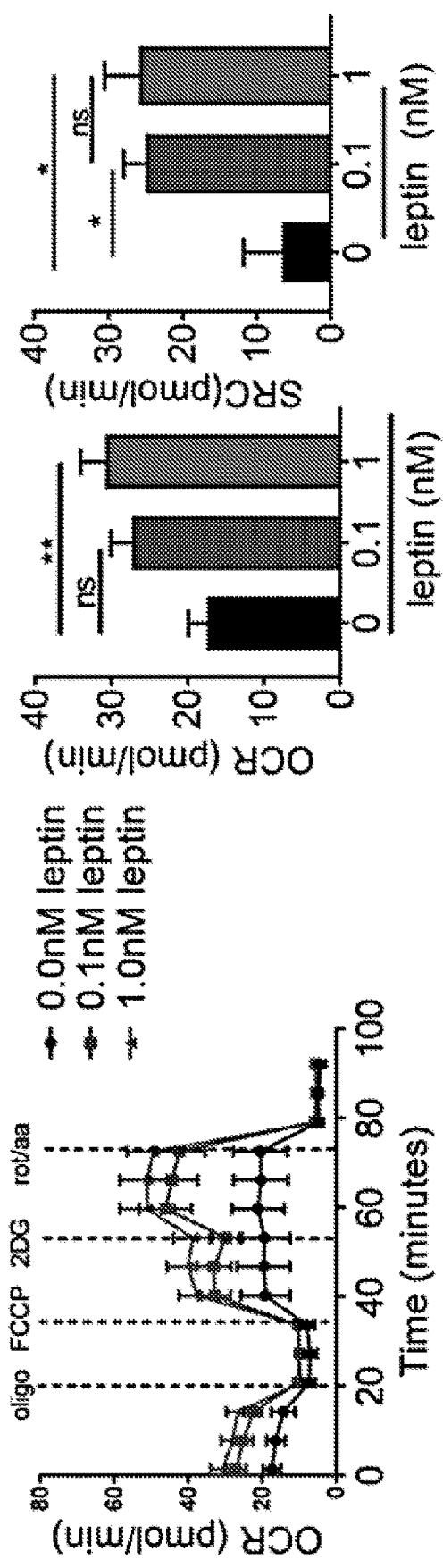
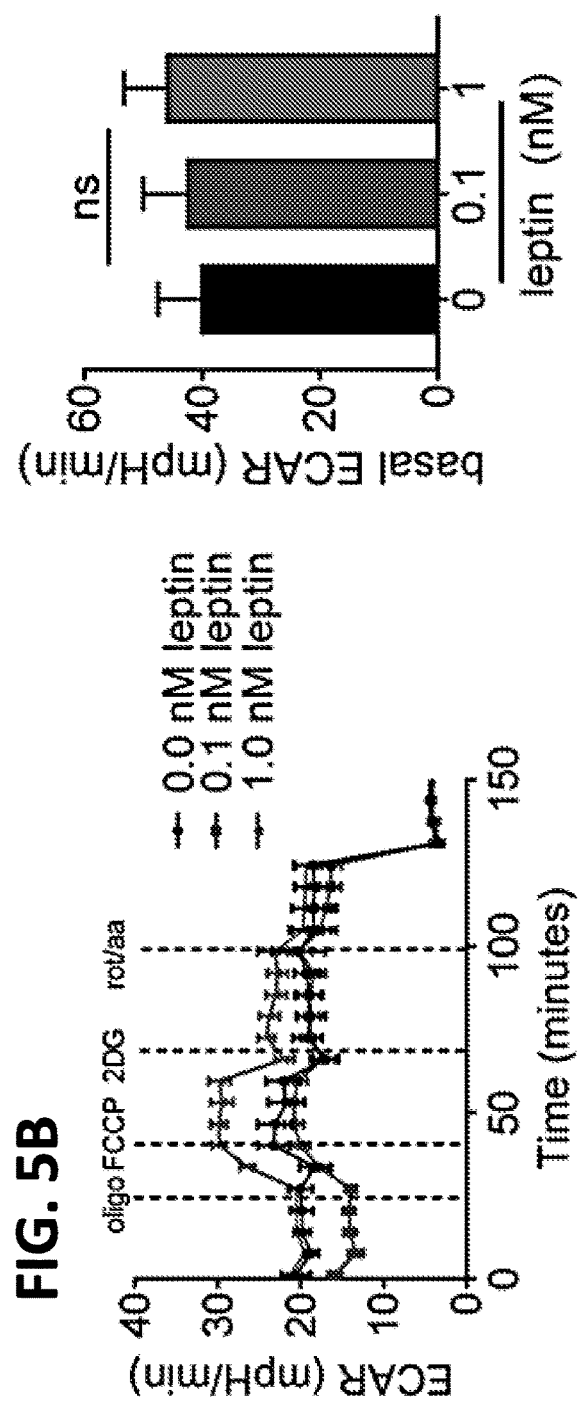
FIG. 5A
FIG. 5B

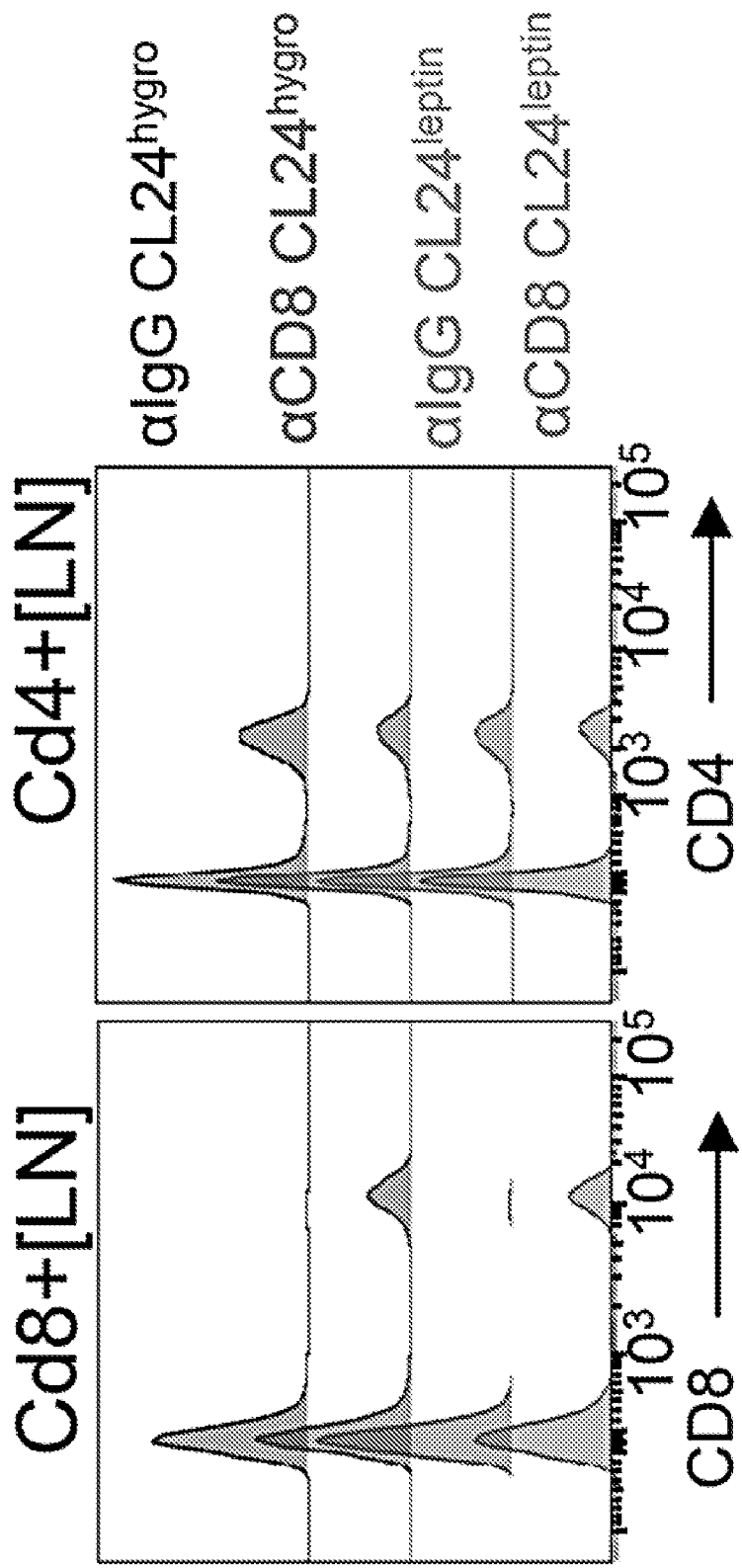

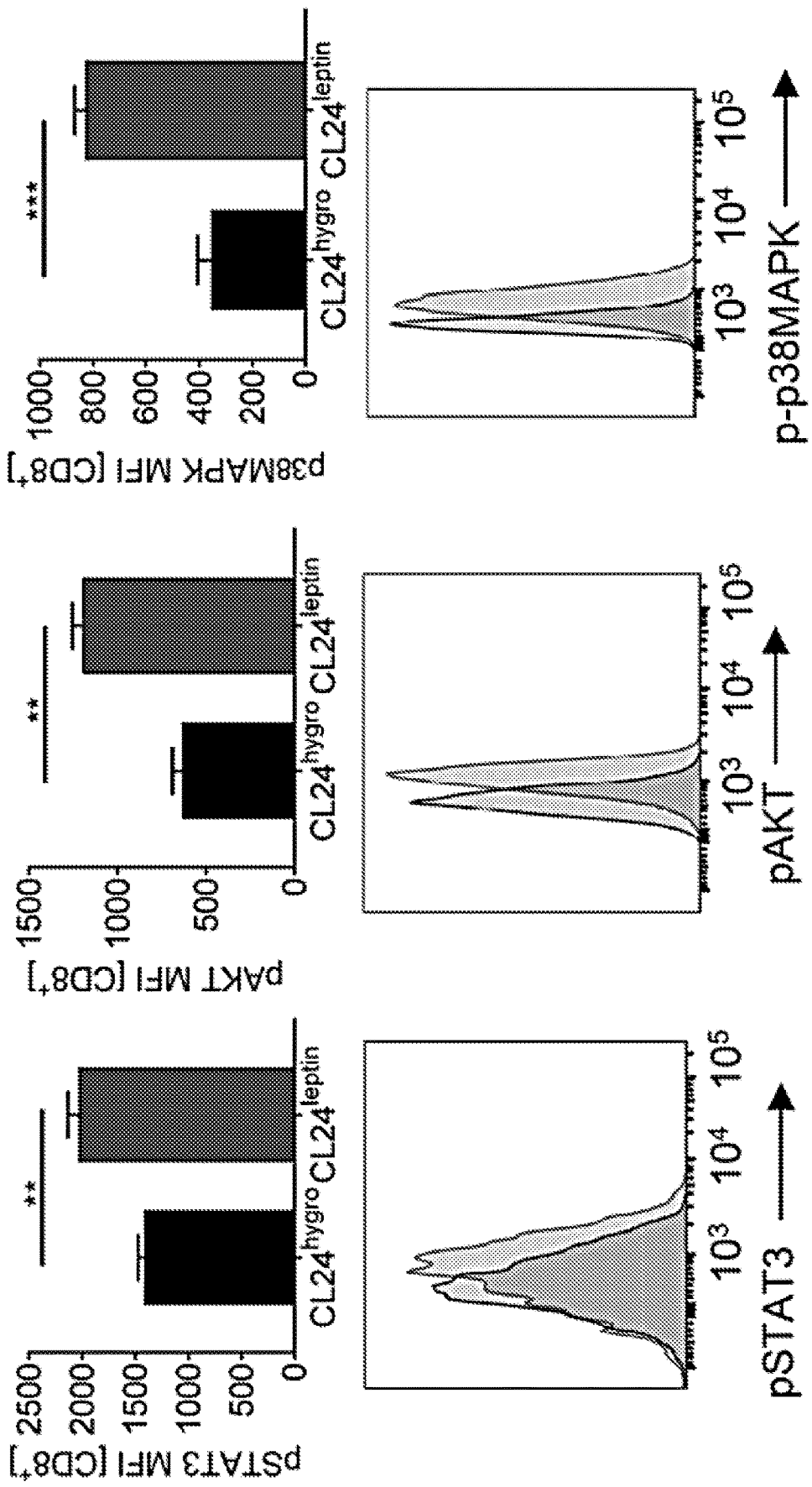

VV ctrl

VV leptin

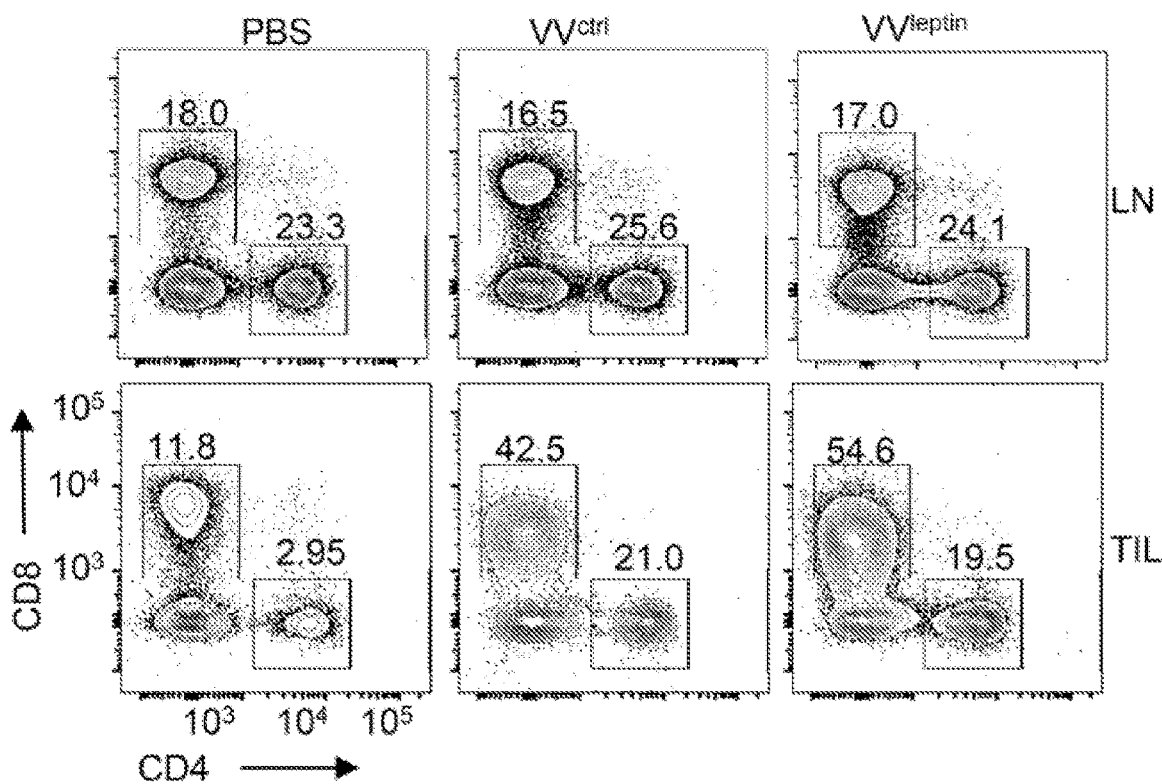
FIG. 9B
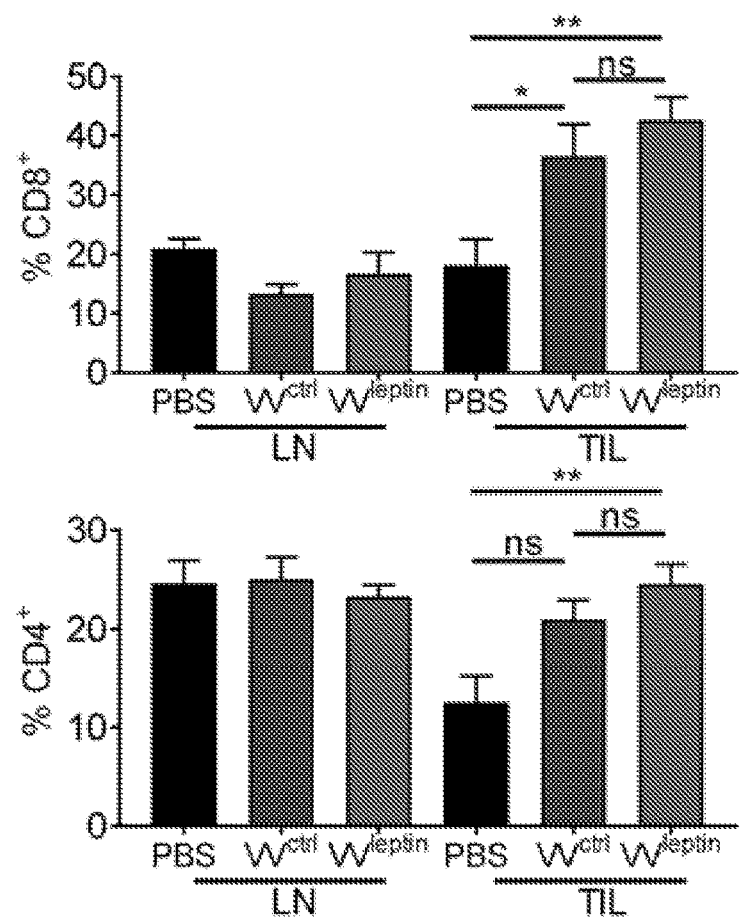

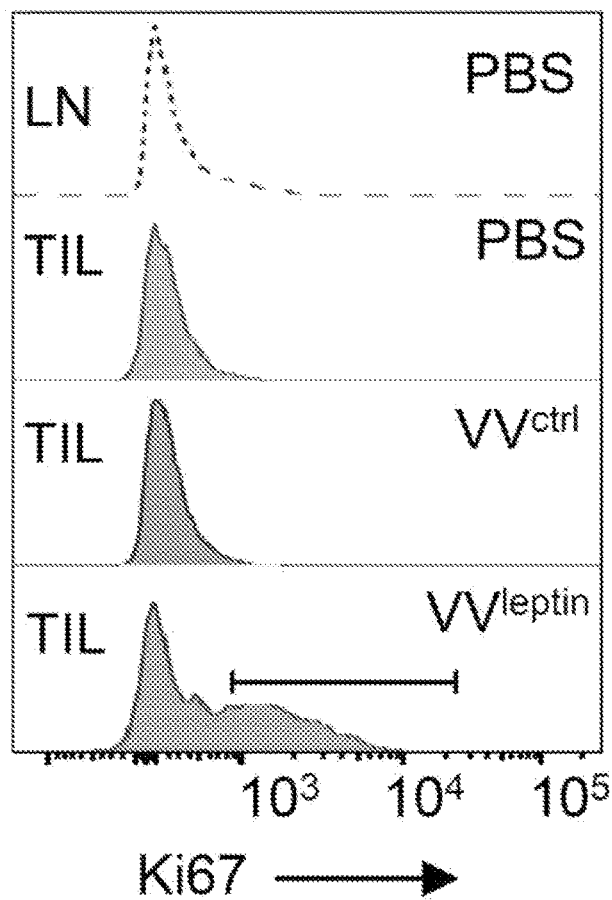
FIG. 10C
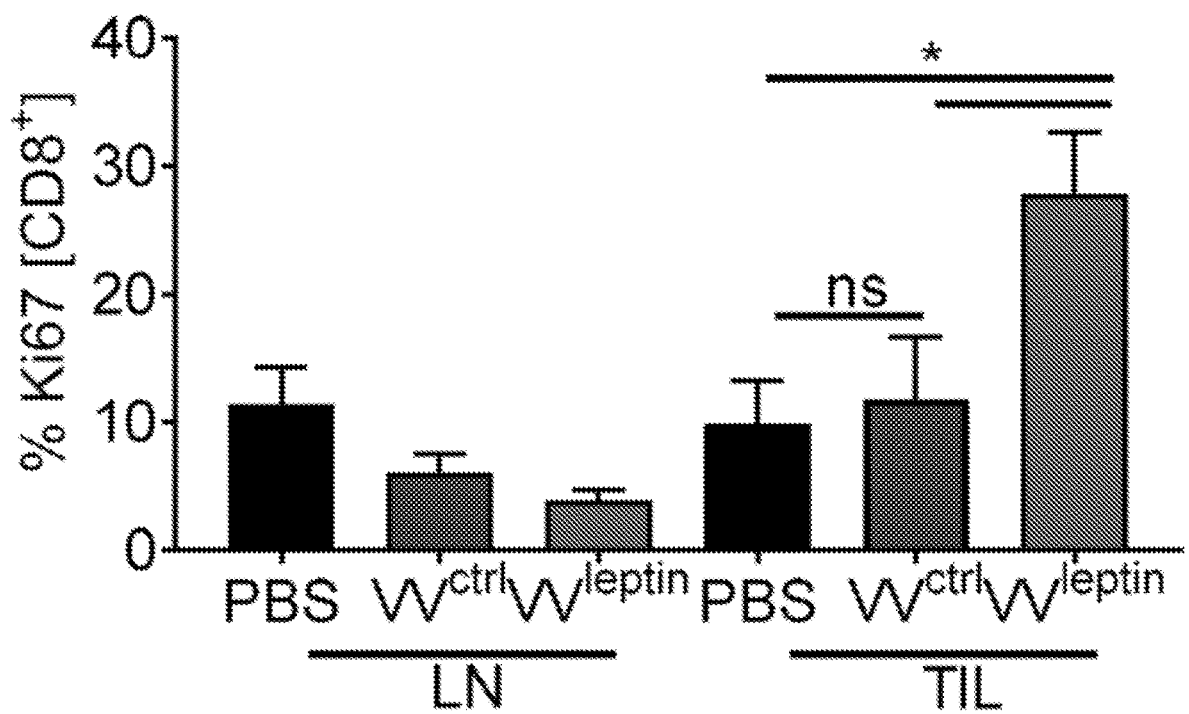

EXPRESSION OF METABOLIC MODULATORS IN TUMOR MICROENVIRONMENT TO IMPROVE TUMOR THERAPY

CROSS REFERENCE TO RELATED APPLICATION

This is the U.S. National Stage of International Application No. PCT/US2019/015434, filed Jan. 28, 2019, which was published in English under PCT Article 21(2), which in turn claims the benefit of U.S. provisional application No. 62/622,547 filed Jan. 26, 2018, both herein incorporated by reference in their entireties.

FIELD

The preset disclosure provides recombinant oncolytic viruses (OVs) that express one or more metabolic modulator proteins, such as leptin, kits including the same, and methods of their use to treat cancer.

BACKGROUND

The successes associated with immunotherapy as a cancer treatment have resulted in a major shift in both cancer research and clinical practice, with a dominant focus on understanding and modulating immune activity at the tumor site. However, the reality of single agent immunotherapies is that the majority of patients will not experience long-term durable benefits. This resistance likely occurs for multiple reasons, but one is a failure to recruit T cells to the tumor and other, more dominant immunosuppressive mechanisms which limit T cell function in the tumor microenvironment (Sharma et al., Cell 2017; 168(4):707-23). Therefore, there is the need for new therapeutic modalities that could overcome these resistance mechanisms.

Leptin is a canonical adipokine with potent metabolic reprogramming functions such as the promotion of glucose and fatty oxidation as well as mitochondrial biogenesis. However, to date the study of leptin in immunity has not been ascertained therapeutically, much less in the context of cancer therapy.

SUMMARY

The infiltrate of aggressive melanomas induced by oncolytic Vaccinia virus is provided herein. It is shown that while oncolytic viruses promote the infiltration of a robust tumor infiltrate, it is ultimately ineffective at promoting complete responses, due in part to metabolic insufficiency. The utility of leptin as a tool to overcome the observed metabolic insufficiency by promoting the metabolic reprogramming of tumor-infiltrating T cells is demonstrated, in some embodiments of this disclosure. Using a novel melanoma model in which leptin is locally elevated in the tumor microenvironment, potent T cell activation and tumor control that was linked to metabolic reprogramming was observed. Further, the Vaccinia virus used was engineered to genetically express and deliver leptin to the tumor microenvironment. This therapy resulted in complete therapeutic responses compared to wild type virus. Leptin expressing vaccinia virus simultaneously lyses tumor cells, leading to stimulation of new T cell infiltration, while also metabolically supporting the activity of that infiltrate through the local secretion of leptin.

Provided herein, in some embodiments, are recombinant oncolytic viruses (OVs) that can include a nucleic acid molecule that can code for one or more proteins capable of inducing metabolic reprogramming of T cells into, e.g., resulting in enhanced infiltration of T cells in tumors, or are capable of modulating an anti-tumor immune response in the tumor microenvironment. For instance, in some cases, the OVs can include one or more nucleic acid molecules that can code for one or more metabolic modulating proteins (e.g., hormones such as an adipokine (e.g., leptin, adiponectin, apelin, chemerin, interleukin-6 (IL-6), monocyte chemotactic protein-1 (MCP-1), plasminogen activator inhibitor-1 (PAI-1), retinol binding protein 4 (RBP4), tumor necrosis factor-alpha (TNFα), visfatin, omentin, vaspin, progranulin or CTRP-4), insulin, and/or insulin-like growth factor 1 (IGF-1)). In some examples, the nucleic acid can be operably linked to a promoter. Examples of OVs include a herpes simplex virus (HSV) (such as T-VEC), vaccinia virus (such as Western Reserve strain), adenovirus, poxvirus, reovirus, poliovirus, coxsackie virus, measles virus, vesicular stomatitis virus (VSV), Seneca valley virus, ECHO virus, Newcastle disease virus, chicken anemia virus, or parovirus. In some examples, the recombinant OV expresses a recombinant protein having at least 80%, at least 90%, or at least 95% sequence identity to SEQ ID NO: 2, 4, 6, or 8. In some examples the recombinant OV includes a nucleic acid molecule encoding a metabolic modulating protein having at least 80%, at least 90%, or at least 95% sequence identity to SEQ ID NO:1, 3, 5 or 7. In some examples the metabolic modulating protein(s) expressed by the recombinant OV is part of a fusion protein, such as a fusion protein that includes two portions, (1) a metabolic modulating protein and (2) second protein (such as a cytokine (e.g., IL-2 or IL-15), chemokine, an interferon, an interleukin, a lymphokine, and/or a tumor necrosis factor). In one example, the fusion protein has the metabolic modulating protein at its N-terminus, and a cytokine at its C-terminus. In some examples, the two portions of the fusion protein are joined by a linker (such as a GSG peptide). In a specific example, the recombinant OV expresses a fusion protein that includes leptin-linker-IL-2, leptin-IL-2, leptin-linker-IL-15, or leptin-IL-15.

Also provided are methods of treating a tumor in a subject, increasing T cell infiltration into a tumor or tumor microenvironment, or both. In some examples, such methods include administering a therapeutically effective amount of one or more recombinant OVs disclosed herein to the subject, thereby treating the tumor. In some examples, such methods include administering a therapeutically effective amount of one or more metabolic modulating proteins (such as leptin, insulin, chemerin, and/or insulin-like growth factor 1) or nucleic acid molecules encoding the protein(s) to the subject, thereby treating the tumor. In some examples, the tumor is a cancer, such as a cancer of the lung, breast, prostate, liver, pancreas, skin, colon, head and neck, kidney, cervix, or ovary. In a specific example, the cancer is melanoma. In a specific example, the cancer is breast cancer. Such methods can further include administering a therapeutically effect amount of one or more further therapies, such as additional anti-cancer agents, such as chemotherapy, radiotherapy, a biologic, surgery, or combinations thereof. In one example, the anti-cancer agent includes one or more immunomodulatory agents, such as, an antagonist of PD-1, an antagonist of PD-L1, a CTLA4 antagonist, and a T cell agonist (such as an agonist of 4-1BB, an agonist of OX40, an agonist of glucocorticoid-induced tumor necrosis factor (TNF) receptor (GITR)), or combinations thereof. In one example, the anti-cancer agent includes a T cell agonist, such as an agonist of 4-1BB, an agonist of OX40, or an agonist of GITR (such as a monoclonal antibody (mAb) specific for an immune check point protein, such as one of the proteins listed above, a ligand of one of these proteins, or an aptamer of one of these proteins).

Also provided are kits and compositions that can include (1) one or more recombinant OVs provided herein, and (2) one or more of an immunomodulatory agent (e.g., an immune checkpoint inhibitor), such as an antagonist of PD-1, an antagonist of PD-L1, a CTLA4 antagonist, and a T cell agonist (such as an agonist of 4-1BB, an agonist of OX40, or an agonist of GITR). The components of a kit can be in separate containers. In some examples, the kit includes (1) one or more recombinant OVs provided herein, and (2) a T cell agonist (such as an agonist of 4-1BB, an agonist of OX40, an agonist of GITR, or a combination thereof). In some examples, the composition includes (1) one or more recombinant OVs provided herein, and (2) one or more a T cell agonists (such as an agonist of 4-1BB, an agonist of OX40, or an agonist of GITR). Such a composition can further include a pharmaceutically acceptable carrier. In some examples, such a composition is lyophilized. In some examples, such composition is present in a container, such as a glass or plastic container.

The foregoing and other objects and features of the disclosure will become more apparent from the following detailed description, which proceeds with reference to the accompanying figures.

BRIEF DESCRIPTION OF THE DRAWINGS

FIGS. 4A-4D. The leptin receptor is upregulated in tumor infiltrating T cells and leptin is capable of metabolic reprogramming C57BL/6J mice were injected subdermally with CL24 cells. 5-7 days after tumor cell injection tumors were treated intratumorally with PBS, control Vaccinia virus (VV$^{ctrl1}$). (A) CD8 and CD4 expression analysis on LN and TIL from mice treated as in (A). Representative flow cytogram of CD8 and CD4 staining in LN and TIL and tabulated flow cytometric data. (B) Expression of inhibitory molecules PD1 and TIM3 from mice treated as in (A). Representative PD1 and Tim3 staining in LN and TIL and tabulated flow cytometric data. (C) Representative histogram PD1 expression on CD8+ T cells and tabulated data. (D) Mitochondrial content analyzed by mitotracker staining in CD8+ T cells from mice treated as in (A). Representative flow cytogram of mitotracker against 2NBDG staining in LN and TIL and tabulated flow cytometric data. Data represents at least 3 independent experiments *p<0.05, p<0.01, *p<0.001 by paired t-test. Error bars indicate s.e.m.

FIGS. 5A-5E. The leptin receptor is upregulated in tumor infiltrating T cells and leptin is capable of metabolic reprogramming (A) Representative OCR trace and tabulated OCR and Spare Respiratory Capacity (SRC) of CD8+ T cells activated with 3 ug/ml: immobilized anti-CD3 in the presence of antiCD28 (2 ug/mL) for 24 h. Cells were treated with 0.0, 0.1, and 1.0 nM of mouse recombinant leptin for 24 h. (B) Representative ECAR trace for cells treated as (A). (C) Mitochondrial content analyzed by mitotracker staining and glucose uptake by 2NBDG staining in CD8+ T cells from mice treated as in (A). Representative flow cytogram of mitotracker against 2NBDG staining in LN and TIL and tabulated flow cytometric data. (D) Leptin receptor staining of CD8+ T cells from mouse lymph nodes (LN) and tumor infiltrating CD8+ T cells (TIL) from tumor bearing mice. (E) Leptin receptor expression staining of PD1 and Tim3 in CD8+ T cells in LN and TIL. Data represents at least 3 independent experiments *p<0.05 by unpaired t-test. Error bars indicate s.e.m. Data represents at least 3 independent experiments *p<0.05, p<0.01, *p<0.001 by paired t-test. Error bars indicate s.e.m.

FIGS. 6A-6F. Characterization of leptin overexpression in tumor cells and effects in the tumor microenvironment. (A) Immunoblot analysis of mouse leptin protein expression of CL24 cell line stably transduced with control plasmid (CL24$^{hygro}$) and mouse leptin gene plasmid (CL24$^{leptin}$). (B) ELISA analysis of leptin in the media of cells transduced with control plasmid and leptin gene. (C) In vitro growth analysis between CL24$^{hygro}$ and CL24$^{leptin}$ cell lines. (H) NK1.1 and B220 analysis for natural killer cells and B cells respectively on LN and TIL from mice injected with CL24$^{hygro}$ and CL24$^{leptin}$. (D) C57BL/6J mice were treated every other day with anti-CD8 (200 ug). At day 6 mice were injected with either CL24$^{hygro}$ or CL24$^{leptin}$ and tumor growth was monitored. CD8 and CD4 expression analysis in lymph node (LN). (E) Representative flow cytogram for NK1.1 and B220 staining in LN and TIL and tabulated flow cytometric data are shown. (F) Representative flow cytogram and tabulated flow cytometric data for CD8+ T cells from LN and TIL from mice injected with CL24$^{hygro}$ and CL24$^{leptin}$ analyzed for pSTAT3, pAKT and pp38MAPK expression. Data represents at least 3 independent experiments *p<0.05, p<0.01, *p<0.001 by two-way ANOVA. Error bars indicate s.e.m.

FIGS. 9A-9E. Leptin-engineered Vaccinia virus promotes the accumulation of memory-like T cell clones. (A) C57BL/6J mice were injected subdermally with CL24 cells. 5-7 days after tumor cell injection tumors were treated intratumorally with PBS, VVcontrol, or VVleptin at 2.5×106 PFU and tumor growth monitored. Each line represents an individual mouse. On day 10 after treatment lymphocytes were isolated from TIL and LN. (B)) Representative flow cytogram and tabulated flow cytometric data for CD8 and CD4 expression. (C-D) TCR sequencing of genomic DNA extracted from CL24 bearing mice treated intratumorally with PBS, VVcontrol, or VVleptin at 2.5×106 PFU. (n=5 each treatment) (C) Total templates and productive rearrangements. (D) Analysis of sample clonality and mean frequency. (E) Mice were treated as in (A). Representative hystograms and tabulated flow cytometric data of CD8+ T cells stained for CD127 expression. Data represents at least 3 independent experiments $*p<0.05$, $p<0.01$, $*p<0.001$ by two-way ANOVA. Error bars indicate s.e.m.

FIGS. 10A-10C. Leptin qualitatively improves the oncolytic virally induced T cell infiltrate through metabolic reprogramming C57BL/6J mice were injected subdermally with CL24 cells. 5-7 days after tumor cell injection tumors were treated intratumorally with PBS, VV$^{control}$ or VV$^{leptin}$. On day 10 after treatment lymphocytes were isolated from TIL and LN. (A) Representative hystograms and tabulated flow cytometric data of CD8+ T cells isolated from LN and TIL were analyzed for mitochondrial protein VDAC. (B) Isolated lymphocytes were stimulated overnight with PMA and ionomycin. Representative flow cytogram and tabulated flow cytometric data for cytokine production analysis by staining for IFNγ and TNFα. (C) Representative hystograms and tabulated flow cytometric data for CD8+ T cells from LN and TIL from mice treated as in (A) analyzed for Ki67 expression. Data represents at least 3 independent experiments $*p<0.05$, $p<0.01$, $*p<0.001$ by two-way ANOVA. Error bars indicate s.e.m.

SEQUENCE LISTING

Figure 1A:
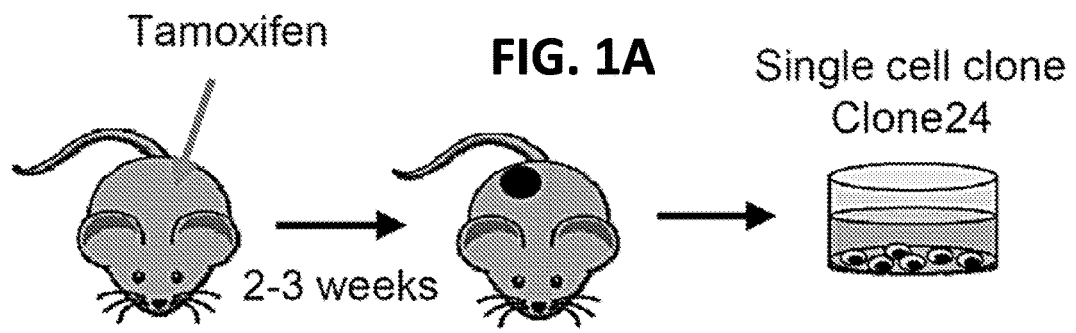
FIGS. 1A-1C. Generation of Clone 24 from Ptenf/fBrafLSL-V600ETyrCre.ERT2 mice, and depletion of CD8+ T cells from CL24lep or CL24hygro bearing mice. (A) C57BL/6J mice were from mice injected with CL24. Representative flow cytogram and tabulated flow cytometric data for CD8+ T cells from LN and TIL. (B) C57BL/6J mice were from mice injected with CL24. Tumors were then treated with anti-PD1 every other day and tumor growth monitored. Representative flow cytogram of CD8 and CD4 staining in LN and TIL. (C) C57BL/6J mice were treated every other day with anti-CD8 (200 ug). At day 6 mice were injected with either CL24hygro or CL24leptin.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The sequence listing filed here with, generated on Jun. 29, 2020, 28 kb, is herein incorporated by reference.

SEQ ID NOS: 1 and 2: Exemplary human leptin nucleic acid and protein sequence, respectively (see GenBank® Accession Nos. NM_000230.2 and NP_000221.1, respectively). Coding sequence is nt 58-561 of SEQ ID NO: 1. Signal peptide is aa 1-21, and the mature peptide is aa 22-167 of SEQ ID NO: 2.

SEQ ID NOS: 3 and 4: Exemplary human insulin nucleic acid and protein sequences, respectively (see GenBank® Accession Nos. AH002844.2 and AAA59172.1, respectively). Coding sequence is nt 2424..2610,3397..3542 of SEQ ID NO: 3. Signal peptide is aa 1-24, and the mature peptide is aa 25-110 of SEQ ID NO: 4.

SEQ ID NOS: 5 and 6: Exemplary human chemerin (also known as retinoic acid receptor responder protein 2) nucleic acid and protein sequences, respectively (see GenBank® Accession Nos. NM_002889.3 and NP_002880.1, respectively). Coding sequence is nt 118-609 of SEQ ID NO: 5. Signal peptide is aa 1-20, and the mature peptide is aa 21-157 of SEQ ID NO: 6.

SEQ ID NOS: 7 and 8: Exemplary human insulin like growth factor 1 (IGF-1) nucleic acid and protein sequences, respectively (see GenBank® Accession Nos. NM_001111283.2 and NP_001104753.1, respectively). Coding sequence is nt 265-741 of SEQ ID NO: 7. Signal peptide is aa 1-21, and the mature peptide is aa 49-118 of SEQ ID NO: 8.

DETAILED DESCRIPTION

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a*

*Comprehensive Desk Reference*, published by VCH Publishers, Inc., 1995; and other similar references.

As used herein, the singular forms "a," "an," and "the," may refer to both the singular as well as plural, unless the context clearly indicates otherwise. As used herein, the term "comprises" can mean "includes." Thus, "comprising a nucleic acid molecule" may mean "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references, including patent applications and patents, and sequences associated with the GenBank® Accession Numbers listed (as of Jan. 26, 2018) are herein incorporated by reference.

In order to facilitate review of the various embodiments of the disclosure, the following explanations of specific terms are provided:

Administration:

To provide or give a subject an agent, such as a disclosed recombinant OV or other therapeutic agent (such as an anti-cancer agent), by any effective route. Exemplary routes of administration include, but are not limited to, injection (such as subcutaneous, subdermal, intramuscular, intradermal, intraperitoneal, intratumoral, and intravenous), transdermal, intranasal, oral, vaginal, rectal, and inhalation routes.

Cancer:

A malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

Chemerin:

(e.g., OMIM 601973): Also known as retinoic acid receptor responder protein 2 (RARRES2). Chemerin is a chemoattractant protein that acts as a ligand for the G protein-coupled receptor CMKLR1. Due to its role in adipocyte differentiation and glucose uptake, chemerin is classified as an adipokine. Human chemerin is encoded by the RARRES2 gene on chromosome 7, and the native protein is about 14 kDa, which is secreted in an inactive form as prochemerin and is activated through cleavage of the C-terminus by inflammatory and coagulation serine proteases. Chemerin sequences are publically available, for example from the GenBank® sequence database (e.g., Accession Nos. NP_002880.1 and NP_001013445.1 provide exemplary chemerin protein sequences, while Accession Nos. NM_002889.3 and NM_001013427.1 provide exemplary chemerin nucleic acid sequences). One of ordinary skill in the art can identify additional chemerin nucleic acid and protein sequences, including chemerin variants, such as those having at least 80%, at least 85%, at least 90%, at least 92%, at least 95%, at least 98%, or at least 99% sequence identity to these GenBank® sequences, such as at least 80%, at least 85%, at least 90%, at least 92%, at least 95%, at least 98%, or at least 99% sequence identity to the peptide aa 21-157 of SEQ ID NO: 6.

Contact:

Placement in direct physical association, including a solid or a liquid form. Contacting can occur in vitro or ex vivo, for example, by adding a reagent to a sample (such as one containing tumor cells), or in vivo by administering to a subject.

Effective Amount (or Therapeutically Effective Amount):

The amount of an agent (such as recombinant OVs disclosed herein, as well as other anti-cancer agents) that is sufficient to effect beneficial or desired results.

An effective amount (also referred to as a therapeutically effective amount) may vary depending upon one or more of: the subject and disease condition being treated, the weight and age of the subject, the severity of the disease condition, the manner of administration and the like, which can readily be determined by one of ordinary skill in the art. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition.

In one embodiment, an "effective amount" (e.g., of a leptin, insulin, chemerin, or IGF-1 protein, recombinant OVs disclosed herein expressing such a protein) may be an amount sufficient to reduce the volume/size of a tumor, the weight of a tumor, the number/extent of metastases, reduce the volume/size of a metastasis, the weight of a metastasis, or combinations thereof, for example by at least about 10%, at least about 20%, at least about 25%, at least about 50%, at least about 70%, at least about 75%, at least about 80%, at least about 90%, at least about 95%, or at least about 99% (as compared to no administration of the therapeutic agent). In one embodiment, an "effective amount" (e.g., of leptin, insulin, chemerin, or IGF-1 or a OV expressing such a protein) may be an amount sufficient to increase T cell infiltration, for example into a tumor or tumor microenvironment, by at least about 10%, at least about 20%, at least about 25%, at least about 50%, at least about 70%, at least about 75%, at least about 80%, at least about 90%, at least about 95%, at least about 99%, at least about 100%, at least about 200%, at least about 300%, at least about 400%, at least about 500%, or at least about 600% (as compared to no administration of the therapeutic agent).

Fusion (or Chimeric) Protein:

A protein containing amino acid sequence from at least two different (heterologous) proteins or peptides. Fusion proteins can be generated, for example, by expression of a nucleic acid sequence engineered from nucleic acid sequences encoding at least a portion of two different (heterologous) proteins. To create a fusion protein, the nucleic acid sequences are typically in the same reading frame and contain no internal stop codons. In one example, a fusion protein including a metabolic modulating protein (such as an adipokine (e.g., leptin or chemerin), insulin, or IGF-1), and a cytokine (such as IL-2 or IL-15) can be expressed by an OV provided herein.

Fusion proteins include a first portion and a second portion, which can be joined directly or via a linker (such as a peptide linker). In some examples, the first portion is a metabolic modulating protein (such as an adipokine (e.g., leptin or chemerin), insulin, or IGF-1), and the second portion is a cytokine (such as IL-2 or IL-15). In some examples, the first portion is N-terminal and the second portion is C-terminal. In some examples, the first portion is C-terminal and the second portion is N-terminal.

Insulin:

(e.g., OMIM 176730): A hormone produced by beta cells of pancreatic islet cells. It regulated the metabolism of carbohydrates, fats and protein, for example by promoting the absorption of carbohydrates, especially glucose from the blood into liver, fat and skeletal muscle cells. Human insulin is encoded by the Ins gene on chromosome 11. Within vertebrates, the amino acid sequence of insulin is strongly conserved. Bovine insulin differs from human in only three amino acid residues, and porcine insulin in one. Insulin sequences are publically available, for example from the GenBank® sequence database (e.g., Accession Nos. AAA59172.1 and AAA41439.1 provide exemplary insulin protein sequences, while Accession Nos. AH002844.2 and V01242.1 provide exemplary insulin nucleic acid sequences). One of ordinary skill in the art can identify additional insulin nucleic acid and protein sequences, including insulin variants, such as those having at least 80%, at least 85%, at least 90%, at least 92%, at least 95%, at least 98%, or at least 99% sequence identity to these GenBank® sequences, such as at least 80%, at least 85%, at least 90%, at least 92%, at least 95%, at least 98%, or at least 99% sequence identity to the peptide aa 25-110 of SEQ ID NO: 4.

Insulin-Like Growth Factor 1 (IGF-1):

(e.g., OMIM 147440): Also called somatomedin C, is a hormone predominantly made by the liver, which is stimulated by growth hormone. Human IGF-1 is encoded by the IGF1 gene on chromosome 12, and the native protein is 70 amino acids. IGF-1 sequences are publically available, for example from the GenBank® sequence database (e.g., Accession Nos. NP_001104753.1 (mature peptide aa 49-118), and NP_034642.2 (mature peptide aa 49-116) provide exemplary IGF-1 protein sequences, while Accession Nos. NM_000618.4, NM_001111283.2 and NM_010512.5 provide exemplary IGF-1 nucleic acid sequences). One of ordinary skill in the art can identify additional IGF-1 nucleic acid and protein sequences, including IGF-1 variants, such as those having at least 80%, at least 85%, at least 90%, at least 92%, at least 95%, at least 98%, or at least 99% sequence identity to these GenBank® sequences, such as at least 80%, at least 85%, at least 90%, at least 92%, at least 95%, at least 98%, or at least 99% sequence identity to the peptide aa 49-118 of SEQ ID NO: 8.

Leptin:

(e.g., OMIM 164160): A hormone predominantly made by adipose cells, which helps to regulate energy balance by inhibiting hunger. Human leptin is encoded by the Lep gene on chromosome 7, and the native protein is 16 kDa and 167 amino acids. Leptin sequences are publically available, for example from the GenBank® sequence database (e.g., Accession Nos. NP_000221.1, NP_001003070.1, NP_999005.1, NP_037208.1, NP_032519.1, and NP_001036220.1 provide exemplary leptin protein sequences, while Accession Nos. NM_000230.2, NM_001003070.1, NM_213840.1 and NM_013076.3 provide exemplary leptin nucleic acid sequences). One of ordinary skill in the art can identify additional leptin nucleic acid and protein sequences, including leptin variants, such as those having at least 80%, at least 85%, at least 90%, at least 92%, at least 95%, at least 98%, or at least 99% sequence identity to these GenBank® sequences such as at least 80%, at least 85%, at least 90%, at least 92%, at least 95%, at least 98%, or at least 99% sequence identity to the peptide aa 22-167 of SEQ ID NO: 2.

Increase or Decrease:

A statistically significant positive or negative change, respectively, in quantity from a control value (such as a value representing no therapeutic agent). An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95%, or no more than 99%.

Isolated:

An "isolated" biological component (such as an OV, a nucleic acid molecule, or a protein) has been substantially separated, produced apart from, or purified away from other biological components in the cell or tissue of an organism in which the component occurs, such as other cells (e.g., RBCs), chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. Isolated recombinant OVs in some examples are at least 50% pure, such as at least 75%, at least 80%, at least 90%, at least 95%, at least 98%, or at least 100% pure.

Linker:

A moiety or group of moieties that joins or connects two or more discrete separate peptide or proteins, such as monomer domains, for example to generate a fusion protein. In one example a linker is a substantially linear moiety. Exemplary linkers that can be used to generate the fusion proteins provided herein include but are not limited to: peptides, nucleic acid molecules, peptide nucleic acids, and optionally substituted alkylene moieties that have one or more oxygen atoms incorporated in the carbon backbone. A linker can be a portion of a native sequence, a variant thereof, or a synthetic sequence. Linkers can include naturally occurring amino acids, non-naturally occurring amino acids, or a combination of both. In one example a linker is composed of at least 5, at least 10, at least 15 or at least 20 amino acids, such as 5 to 10, 5 to 20, or 5 to 50 amino acids. In one example the linker is a poly alanine. The linker can be a flexible linker (e.g., (GGGGS)n), rigid linker (e.g., (EAAAK)n), or a cleavable linker (e.g., disulfide, protease sensitive).

Metabolic Modulator Protein:

A protein that can increase or decrease the metabolic activity of a cell, such as a T cell, such as a T cell in a subject with cancer. In one example, a metabolic modulator protein increases the metabolic activity of a T cell, such as a tumor infiltrating T cell. In some examples, the metabolic modulator protein increases the metabolic activity of a cell, such as a T cell, such as a tumor infiltrating T cell, by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of the metabolic modulator protein (such as the absence of administering an OV expressing a metabolic modulator protein). In some examples, the metabolic modulator protein increases the mitochondrial function of a cell, such as a T cell, such as a tumor infiltrating T cell, by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of the metabolic modulator protein (such as the absence of administering an OV expressing a metabolic modulator protein). In some examples, the metabolic modulator protein increases the oxidative phosphorylation by a cell, such as a T cell, such as a tumor infiltrating T cell, by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of the metabolic modulator protein (such as the absence of administering an OV expressing a metabolic modulator protein). In some examples, the metabolic modulator protein increases memory T cells by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of the metabolic modulator protein (such as the absence of administering an OV expressing a metabolic modulator protein). In some examples, the metabolic modulator protein increases T cell clonal expansion in a tumor (e.g., cancer) by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of the metabolic modulator protein (such as the absence of administering an OV expressing a metabolic modulator protein). In some examples, combinations of one or more of these affects may be achieved.

In one example, the metabolic modulator protein is an adipokine. An adipokine can be a cytokine secreted by adipose tissue. Examples of adipokines include, but are not limited to: leptin, adiponectin, apelin, chemerin, interleukin-6 (IL-6), monocyte chemotactic protein-1 (MCP-1), plasminogen activator inhibitor-1 (PAI-1), retinol binding protein 4 (RBP4), tumor necrosis factor-alpha (TNFα), visfatin, omentin, vaspin, progranulin and CTRP-4. In one example, the metabolic modulator protein is insulin. In one example, the metabolic modulator protein is IGF-1.

Oncolytic Virus (OV):

A virus that preferentially infects and kills cancer cells. OVs can access cells through binding to receptors on their surface or through fusion with the plasma membrane and establish a lytic cycle in tumors, while leaving normal tissue essentially unharmed. As the infected cancer cells are destroyed by oncolysis, they release new infectious virus particles or virions to help destroy the remaining tumor. Exemplary oncolytic viruses include but are not limited to herpes simplex virus (HSV), vaccinia virus, adenovirus, poxvirus, reovirus, poliovirus, coxsackie virus, measles virus, vesicular stomatitis virus (VSV), Seneca valley virus, ECHO virus, Newcastle disease virus, chicken anemia virus, and parovirus. Specific examples of oncolytic viruses include the ECHO-7 strain enterovirus RIGVIR, a genetically modified adenovirus named H101, and talimogene laherparepvec (T-VEC).

A recombinant OV is an OV that includes non-native sequences, such as a nucleic acid molecule encoding a metabolic modulating protein, such as one or more of leptin, insulin, chemerin, and insulin-like growth factor 1, as well as a fusion protein including such and a cytokine.

Operably Linked:

A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence (such as a leptin, insulin, chemerin, or insulin-like growth factor 1 coding sequence). Generally, operably linked sequences are contiguous and, where necessary to join two protein coding regions, in the same reading frame.

Pharmaceutically Acceptable Carriers:

The pharmaceutically acceptable carriers useful in this invention are conventional. Remington's Pharmaceutical Sciences, by E. W. Martin, Mack Publishing Co., Easton, PA, 15th Edition (1975), describes compositions and formulations suitable for pharmaceutical delivery of a therapeutic agent, such as recombinant OV disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Promoter:

An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Examples of promoters that can used with the disclosed recombinant OVs include, but are not limited to viral promoters, such as 7.5 promoter, SV40 promoter, CMV enhancer-promoter, and the CMV enhancer/β-actin promoter. Both constitutive and inducible promoters can be used (see e.g., Bitter et al., *Methods in Enzymology* 153: 516-544, 1987). Also included are those promoter elements which are sufficient to render promoter-dependent gene expression controllable for cell-type specific, tissue-specific, or inducible by external signals or agents; such elements may be located in the 5' or 3' regions of the gene. Promoters produced by recombinant DNA or synthetic techniques can also be used to provide for transcription of the nucleic acid sequences.

Recombinant:

A recombinant nucleic acid molecule is one that has a sequence that is not naturally occurring (e.g., an OV with a non-native sequence, such as a mammalian leptin, insulin, chemerin, or insulin-like growth factor 1 coding sequence) or has a sequence that is made by an artificial combination of two otherwise separated segments of sequence. This artificial combination can be accomplished by routine methods, such as chemical synthesis or by the artificial manipulation of isolated segments of nucleic acids, such as by genetic engineering techniques. Similarly, a recombinant protein is one encoded for by a recombinant nucleic acid molecule. Similarly, a recombinant or transgenic cell is one that contains a recombinant nucleic acid molecule (such as a recombinant OV) and expresses a recombinant protein.

Sequence Identity:

The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Variants of a native leptin, insulin, chemerin, or IGF-1 protein or coding sequences are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Thus, a variant leptin, insulin, chemerin, or IGF-1 protein or nucleic acid sequence can have at least 80%, at least 85%, at least 90%, at least 91%, at least 92%, at least 93%, at least 94%, at least 95%, at least 96%, at least 97%, at least 98% or at least 99% sequence identity to any of the sequences shown in the GenBank® Accession Nos. provided herein (such as SEQ ID NO: 1, 2, 3, 4, 5, 6, 7, or 8).

Subject:

A vertebrate, such as a mammal, for example a human Mammals include, but are not limited to, murines, simians, humans, farm animals, sport animals, and pets. In one embodiment, the subject is a non-human mammalian subject, such as a monkey or other non-human primate, mouse, rat, rabbit, pig, goat, sheep, dog, cat, horse, or cow. In some examples, the subject has a tumor, such as a cancer, that can be treated using the recombinant OVs disclosed herein. In some examples, the subject is a laboratory animal/organism, such as a mouse, rabbit, or rat.

T Cells:

White blood cells containing a T cell receptor on their cell surface, which play a role in cell-mediated immunity.

Therapeutic Agent:

Refers to one or more molecules or compounds that confer some beneficial effect upon administration to a subject. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition.

Transduced and Transformed:

A virus or vector "transduces" a cell when it transfers nucleic acid into the cell. A cell is "transformed" or "transfected" by a nucleic acid transduced into the cell when the nucleic acid molecule becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses {Wolff, J. A., ed, Gene Therapeutics, Birkhauser, Boston, USA (1994)}.

Transgene:

An exogenous gene supplied by a vector, such as a recombinant OV. In one example, a transgene includes one or more leptin, insulin, chemerin, or IGF-1 coding sequences.

Treating, Treatment, and Therapy:

Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, blood and other clinical tests (such as imaging), and the like. In some examples, treatment with the disclosed methods results in a decrease in the number, volume, and/or weight of a tumor and/or metastases.

Tumor, Neoplasia, Malignancy or Cancer:

A neoplasm is an abnormal growth of tissue or cells which results from excessive cell division. Neoplastic growth can produce a tumor. The amount of a tumor in an individual is the "tumor burden" which can be measured as the number, volume, or weight of the tumor. A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Exemplary tumors, such as cancers, that can be treated using the disclosed recombinant OVs include solid tumors, such as breast carcinomas (e.g. lobular and duct carcinomas, such as a triple negative breast cancer), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage, head and neck squamous cell carcinoma, and lymphatic tumors (including B-cell and T-cell malignant lymphoma). In one example, the tumor is an adenocarcinoma.

The disclosed recombinant OVs can also be used to treat liquid tumors, such as a lymphatic, white blood cell, or other type of leukemia. In a specific example, the tumor treated is a tumor of the blood, such as a leukemia (for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia), a lymphoma (such as Hodgkin's lymphoma or non-Hodgkin's lymphoma), or a myeloma.

Under Conditions Sufficient for:

A phrase that is used to describe any environment that permits a desired activity. In one example the desired activity is increased expression or activity of one or more of leptin, insulin, chemerin, or IGF-1, for example in a tumor cell infected with a recombinant OV expressing the protein. In one example the desired activity is treatment of a tumor in vivo, for example using the disclosed recombinant oncolytic viruses.

Vector:

A nucleic acid molecule as introduced into a host cell (such as a tumor cell), thereby producing a transformed host cell. A vector may include nucleic acid sequences that permit it to replicate in the host cell, such as an origin of replication. A vector may also include one or more leptin, insulin, chemerin, and IGF-1 coding sequences, for example in combination other sequences. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Overview

Immunotherapy can reinvigorate dormant responses to cancer, but response rates remain low due to several resistance mechanisms, including immunologic ignorance/exclusion and metabolically harsh microenvironments. Oncolytic viruses (OVs), which can replicate in cancer cells, may induce tumor lysis and immune priming. It is demonstrated herein that oncolytic Vaccinia virus induces substantial remodeling of the tumor microenvironment, dominated by influx of effector T cells. However, the inventors observed that responses to oncolytic viruses were incomplete, possibly be due to metabolic insufficiencies induced by the tumor microenvironment. The adipokine leptin is identified as a potent metabolic reprogramming agent that supports antitumor responses. Leptin metabolically reprograms T cells in vitro, and melanoma cells expressing leptin are immunologically controlled in vivo. Engineering oncolytic viruses to express leptin in tumor cells induced complete responses in tumor-bearing mice and promoted a functionally superior tumor infiltrate. Leptin treatment of tumor bearing animals increased T cell infiltration and potent metabolic reprogramming Tumors engineered to overexpress leptin were controlled more effectively by the immune system and are more metabolically sufficient than wild-type tumors. Thus, leptin leverages an axis that promotes antitumor immunity by increasing the metabolic activity of tumor infiltrating T cells. Thus, leptin and other metabolic reprogramming agents (such as other adipokines such as chemerin, or other proteins such as insulin or IGF-1) can provide metabolic support to tumor immunity and oncolytic viruses represent a platform to deliver metabolic therapy.

Among the many challenges encountered by the immune response in solid tumors is the poor capacity to infiltrate as well as being able to carry out their effector function appropriately in a hostile microenvironment. The data herein show that both obstacles can be overcome by engineering an OV that can deliver metabolic modulation (e.g., the adipokine leptin) directly to the microenvironment, consequently improving therapeutic efficacy. Recent studies have explored the genetic signature defined by OVs in the tumor and determining targets that can be expressed in OVs (Zamarin et al., Nat Commun 2017; 8:14340). The data herein is the first to portray the changes in the immune landscape after oncolytic viral treatments utilizing single cell RNA-seq analysis. These findings reveal striking changes in tumor infiltrate at an early time-point when tumors are not yet regressing. These data indicate that OVs do not simply lyse a portion of tumor cells and promote some immunogenic cell death, but rather have the capacity to completely remodel the tumor immune microenvironment. The data show not only an increased infiltration in the T cell compartment, which is likely central to the observed antitumor immunity, but a wide array of changes in the myeloid population. These results shed new light on the potent immunity induced by OVs and demonstrates that this immune response can be bolstered in specific ways to promote more durable responses.

Improving T cell metabolic function in the tumor microenvironment may allow for a better therapeutic response. This disclosure provides novel methods that employ leptin (or other metabolic modulator of the immune response, such as other adipokines or other hormones such as insulin), especially in cancer. Furthermore, the disclosed methods utilize OVs as an effective delivery system for molecules that can modulate specifically the tumor microenvironment and improve therapeutic response.

Previous studies have shown that immune cells express the leptin receptor and that leptin as a cytokine can have pro-inflammatory functions in innate and adaptive immune responses (Loffreda et al., *FASEB J* 1998; 12(1):57-65; La Cava et al., *Nat Rev Immunol* 2004; 4(5):371-9; Santos-Alvarez et al., *Cell Immunol* 1999; 194(1):6-11). Regarding the adaptive immune response, leptin can activate and enhance proliferation of human T lymphocytes (Martin-Romero et al., *Cell Immunol* 2000; 199(1):15-24). Although there are some observations that leptin might inhibit regulatory T cell proliferation and function in models of inflammation and autoimmunity (Feuerer et al., *Nat Med* 2009; 15(8):930-9), the data herein using oncolytics indicate that Treg cells are not stimulated in a leptin-rich tumor environment.

Little is known about the role of leptin or the leptin receptor in cancer, particularly in the tumor microenvironment. The findings herein demonstrate that there is an increase leptin receptor expression in T cells in the tumor microenvironment compared to those in the secondary lymphoid organs. Leptin can metabolically enhance tumor infiltrating T cell effector function through the persistence of mitochondrial function and an increase in oxidative phosphorylation. Previous studies indicated that leptin can promote fatty acid oxidation in skeletal muscle. CD4+ T cells from leptin deficient mice showed a reduction in glucose uptake along with decreased proliferation and cytokine production. The data herein show that leptin signals through the activation of STAT5 and PI3K, and can increase mitochondrial content and quality. Leptin can promote PGC1α activation and promote oxidative phosphorylation as well as promote mitochondrial fusion through the expression of mitofusin 1 (Roman et al., *Mol Cell Endocrinol* 2010; 314(1):62-9; Hsu et al., *Int J Obes (Lond)* 2015; 39(12): 1750-6.). As tumor infiltrating T cells repress the expression of PGC1α (Scharping et al., *Immunity* 2016; 45(3):701-3), leptin may support TIL function through maintenance of that axis.

The disclosed analysis of the T cell infiltrate of both wild-type and leptin-engineered oncolytic Vaccinia shed light on the immune populations that were more predominant in the tumors treated with leptin-expressing Vaccinia virus. An increase in proportions of memory T cells was observed, which explains the sustained therapeutic response observed. Memory T cells are superior antitumor T cells, have a higher mitochondrial content and oxidative phosphorylation capacity (van der Windt et al., *Immunity* 2012; 36(1):68-78; Sukumar et al., *Cell Metab* 2016; 23(1):63-76), in agreement with the data herein showing an increase in mitochondrial content. TCR sequencing analysis further demonstrated the effects of OVs on tumor infiltrating lymphocytes. While oncolytics induced new T cell clones to infiltrate the tumor, T cell clonal expansion in tumors treated with leptin-expressing Vaccinia virus was observed.

There are benefits to metabolically enhancing mitochondrial function in tumor infiltrating lymphocytes. The methods provided herein increases the repertoire of metabolic modulators that can be delivered directly into the tumor. One method of therapeutic delivery of these metabolic modulators is the utilization of OVs, which can deliver genetically encoded payload directly to the tumor microenvironment. Until now, the majority of oncolytic-delivered genes have been immunologic in nature (e.g., cytokines, costimulatory molecules, etc.). However, the disclosed methods provide the first metabolic modulator delivered by OVs. While Vaccinia is demonstrated herein to be effective, other oncolytics like HSV, Newcastle Disease Virus, adenovirus, and VSV can also be used. While scRNA-seq revealed that oncolytics have potent immune-stimulatory potential early after infection, to achieve durable, complete responses, metabolic support can provide the strong early effector response into long-lived memory capable of mediating robust antitumor effects.

Based on these observations, provided herein are compositions methods that increase or enhance T cell metabolism, thereby increasing antitumor immunity, increasing a tumor's response to immunotherapy, or both. By modulating tumor microenvironment metabolism, for example by providing metabolism modulating proteins in the tumor microenvironment, for example by expressing such proteins from a recombinant OV, enhances anti-tumor effects. Such methods can be used in combination with other anti-cancer therapies, such as with a T cell agonist (e.g., with one or more agonists of 4-1BB, OX40, or GITR).

In some examples, leptin (or other metabolic modulating protein such as another adipokine (e.g., chemerin), insulin, or IGF-1) is administered (for example as a protein, or as a nucleic acid encoding the protein, for example via a vector, such as a viral vector) in therapeutic amounts, for example in combination with other anti-cancer therapy, such as immunotherapies like a T cell agonist, such as one or more agonists of 4-1BB, OX40, and GITR. In some examples, recombinant OVs that are express or overexpress leptin (or other metabolic modulating protein such as another adipokine (e.g., chemerin), insulin, or IGF-1) in tumor cells are used.

OVs that express leptin (or other metabolic modulating protein such as another adipokine (e.g., chemerin), insulin, or IGF-1) can kill tumor cells and stimulate the immune system, but the release of leptin (or other metabolic modulating protein such as another adipokine (e.g., chemerin), insulin, or IGF-1) also improve T cell metabolism at the tumor site. Thus, these recombinant OVs become a potent type of self-bolstering immunotherapy. Recombinant leptin (or other metabolic modulating protein such as another adipokine (e.g., chemerin), insulin, or IGF-1) increases T cell infiltration.

Recombinant Oncolytic Viruses (OVs)

Provided herein are recombinant OVs that can be used to improve cellular immunotherapy, such as cancer immunotherapy. For example, the disclosure provides recombinant OVs containing a nucleic acid molecule that encodes one or more metabolic modulatory proteins, such as an adipokine (e.g., leptin or chemerin), chemerin, or IGF-1. In some examples the metabolic modulatory protein (e.g., an adipokine (e.g., leptin or chemerin), insulin, or IGF-1) is part of a fusion protein expressed by the OV, such as a fusion protein including the metabolic modulatory protein and a gamma chain cytokine (such as IL-2 or IL-15). Expression of the protein in a tumor cell infected with the OVs may result in increased expression of one or more of these proteins, and thus increased activity of these proteins, thereby increasing anti-tumor activity.

The OV can be any OV, such as a naturally occurring OV or a genetically engineered OV. Examples include herpes simplex virus (HSV), vaccinia virus, adenovirus, poxvirus, reovirus, poliovirus, coxsackie virus, measles virus, vesicular stomatitis virus (VSV), Seneca valley virus, ECHO virus, Newcastle disease virus, chicken anemia virus, or parovirus. In a specific example, the OV can be talimogene laherparepvec (T-VEC). In a specific example, the OV can be Western Reserve strain Vaccinia virus. In a specific example, the OV can be vaccinia, and the one or more metabolic modulating proteins can be leptin. In a specific example, the OV can be Western Reserve strain Vaccinia virus, and the one or more metabolic modulating proteins is leptin. In a specific example, the OV is can be Reserve strain Vaccinia virus, and the one or more metabolic modulating proteins can be a leptin-IL-2 or leptin-IL-15 fusion protein (wherein the leptin and cytokine may be joined by a linker).

The nucleic acid molecule encoding the one or more metabolic modulating proteins in some examples is operably linked to a promoter, such as a constitutive or regulatable promoter. In one example, the promoter may not be native to the protein. For example, the promoter can be one from the virus, such as the 7.5 promoter.

In one example, the one or more metabolic modulating proteins can comprise at least about 80%, at least about 90%, at least about 95%, at least about 98%, at least about 99%, or 100% sequence identity to SEQ ID NO: 2, 4, 6, or 8. In one example the a nucleic acid molecule encoding the one or more metabolic modulating proteins can comprise at least about 80%, at least about 90%, at least about 95%, at least about 98%, at least about 99%, or 100% sequence identity to SEQ ID NO:1, 3, 5 or 7. In one example, the one or more metabolic modulating proteins can be a fusion protein including a first protein and a second protein, wherein the first protein comprises at least 80%, at least about 90%, at least about 95%, at least about 98%, at least about 99%, or 100% sequence identity to SEQ ID NO: 2, 4, 6, or 8. In one example the nucleic acid molecule encoding the one or more metabolic modulating proteins can comprise at least about 80%, at least about 90%, at least about 95%, at least about 98%, at least about 99%, or 100% sequence identity to SEQ ID NO:1, 3, 5 or 7. In one example the nucleic acid molecule encoding the one or more metabolic modulating proteins can encode a fusion protein that includes a metabolic protein, wherein the fusion protein can include a first protein and a second protein, wherein the first protein may be encoded by a nucleic acid molecule comprising at least about 80%, at least about 90%, at least about 95%, at least about 98%, at least about 99%, or 100% sequence identity to SEQ ID NO:1, 3, 5 or 7. In some examples, the recombinant OV may further express one or more immune stimulatory proteins, such as a costimulatory molecule, cytokine, a chemokine, such as one or more of IL-2, IL-12, IL-15, IL-18, IFN-α/β, TNF-α, and GM-CSF, or combinations thereof.

In some examples, upon infection of a tumor cell by the disclosed recombinant OVs, expression and/or activity of an adipokine in the infected tumor cells may increase by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of administering the OV, or relative to administration of an OV not expressing an adipokine. In some examples, upon infection of a tumor cell by the disclosed recombinant OVs, leptin expression and/or activity in the infected tumor cells may increase by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of administering the OV, or relative to administration of an OV not expressing leptin. In some examples, upon infection of a tumor cell by the disclosed recombinant OVs, insulin expression and/or activity in the infected tumor cells may increase by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of administering the OV, or relative to administration of an OV not expressing insulin. In some examples, upon infection of a tumor cell by the disclosed recombinant OVs, chemerin expression and/or activity in the infected tumor cells can increase by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of administering the OV, or relative to administration of an OV not expressing chemerin. In some examples, upon infection of a tumor cell by the disclosed recombinant OVs, IGF-1 expression and/or activity in the infected tumor cells may be increased by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of administering the OV, or relative to administration of an OV not expressing IGF-1.

In some examples, expressing an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 in the tumor cells from the OV may increase T cell infiltration into the tumor or tumor microenvironment by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of administering the OV, or relative to administration of an OV not expressing a metabolic modulatory protein. In some examples, expressing an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 in the tumor cells from the OV may increase mitochondrial activity in T cells at the site of the tumor by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of administering the OV, or relative to administration of an OV not expressing a metabolic modulatory protein. In some examples, expressing an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1, in the tumor cells from the OV may increase T cell oxidative phosphorylation by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of administering the OV, or relative to administration of an OV not expressing a metabolic modulatory protein. In some examples, expressing an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1, in the tumor cells from the OV may increase T cell clonal expansion in a tumor by at least about 20%, at least about 30%, at least about 40%, at least about 50%, at least about 60%, at least about 70%, at least about 75%, at least about 80%, at least about 90%, at least about 95%, at least about 100%, at least about 200%, at least about 300%, at least about 400%, at least about 500% or at least about 600%, for example relative to the absence of administering the OV, or relative to administration of an OV not expressing a metabolic modulatory protein. In some examples, combinations of these effects may be achieved.

1. Metabolic Modulating Proteins

The metabolic modulating protein, such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1, coding sequence (which can be one part of a fusion protein coding sequence) in the OV can be wild-type (e.g., non-mutated) or variant sequence. In a specific example, the metabolic modulating protein is leptin. In a specific example, the metabolic modulating protein is chemerin. In a specific example, the metabolic modulating protein is insulin. In a specific example, the metabolic modulating protein is IGF-1.

For example, wild-type leptin, insulin, chemerin, and IGF-1 sequences are provided herein via GenBank® Accession Nos. (and sequences are provided in SEQ ID NOS: 1-8). Thus, in some examples, the recombinant OV introduced into a tumor cell can include a native leptin, insulin, chemerin, and/or IGF-1 coding sequence. In some examples, the recombinant OV introduced into the tumor cell includes a non-native adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 coding sequence, but encodes a native adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 protein sequence (e.g., a coding sequence that is degenerate). In some examples, the adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 protein expressed by the recombinant OV includes the signal sequence.

Variant adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 proteins, including variants of the protein sequences provided above via GenBank® Accession Nos., can contain one or more mutations, such as a single insertion, a single deletion, a single substitution. In some examples, the variant adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 protein includes 1-20 insertions, 1-20 deletions, 1-20 substitutions, and/or any combination thereof (e.g., single insertion together with 1-19 substitutions). In some examples, the disclosure provides a variant of any native adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 protein having 1, 2, 3, 4, 5, 6, 7, 8, 9, 10, 11, 12, 13, 14, 15, 16, 17, 18, 19 or 20 additional amino acid changes, wherein the protein retains native or increased biological activity. In some examples, a variant adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 protein includes 1-8 insertions, 1-15 deletions, 1-10 substitutions, and/or any combination thereof (e.g., 1-15, 1-4, or 1-5 amino acid deletions together with 1-10, 1-5 or 1-7 amino acid substitutions). In some examples, a variant adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 protein has 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid changes. In one example, such variant peptides are produced by manipulating the nucleotide sequence encoding a peptide using standard procedures such as site-directed mutagenesis or PCR.

One type of modification includes the substitution of amino acids for amino acid residues having a similar biochemical property, that is, a conservative substitution (such as 1-4, 1-8, 1-10, or 1-20 conservative substitutions). Typically, conservative substitutions have little to no impact on the activity of a resulting peptide. For example, a conservative substitution is an amino acid substitution in any native adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 protein sequence, which does not substantially affect the native function of the protein. An alanine scan can be used to identify which amino acid residues in a protein can tolerate an amino acid substitution. In one example, the native function of adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 is not altered by more than 25%, for example not more than 20%, for example not more than 10%, when an alanine, or other conservative amino acid, is substituted for 1-4, 1-8, 1-10, or 1-20 native amino acids. Examples of amino acids which may be substituted for an original amino acid in a protein and which are regarded as conservative substitutions include: Ser for Ala; Lys, Gln, or Asn for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

More substantial changes can be made by using substitutions that are less conservative, e.g., selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine. The effects of these amino acid substitutions (or other deletions and/or additions) can be assessed by analyzing the function of the variant leptin, insulin, chemerin, or IGF-1 protein by analyzing the native function of the protein.

The metabolic modulatory protein(s) expressed by the OV can be part of a fusion protein. Thus, an OV expressing a fusion protein that includes an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1, is encompassed by this disclosure, and can be used in the disclosed methods for treating a tumor/cancer. In some embodiments, a fusion protein expressed by the OV can include at least two portions, a metabolic modulatory protein and a further protein. In a specific example, the metabolic modulating protein of the fusion protein can be leptin, chemerin, insulin, and/or IGF-1. In some examples, the further protein can be a cytokine protein, such as a chemokine, an interferon, an interleukin, a lymphokine, a tumour necrosis factor, or a fusion protein comprising any combinations thereof. The metabolic modulatory protein portion of the fusion protein can be a native or a mutated metabolic modulatory protein (such a protein having at least 80%, at least 85%, at least 90%, at least 95%, at least 96%, at least 97%, at least 99%, or 100% sequence identity to SEQ ID NO: 2, 4, 6, or 8). In one example, the further protein is a cytokine protein, such as a native or a mutated cytokine, for example a gamma chain cytokine, such as a native or mutated protein belonging to the IL-2 subfamily of cytokine proteins (such as a native IL-2 or a Super IL-2 (e.g., see Levin et al., Nature 484:529-33, 2012), the IL-1 family of cytokine protein (e.g., IL-18), the IFN subfamily of cytokine proteins, the IL-17 family of cytokine proteins, the TGF superfamily of cytokine proteins (e.g., TGF-β1, TGF-β2, TGF-β3), IL-4, IL-10, IL-13, IL-7, IL-9, IL-15, IL-21, TNFα, IFN-γ, or any combinations thereof. In some cases, the cytokine protein can be a native human protein. In a specific example, the cytokine protein portion of the fusion protein can be IL-2 (e.g., GenBank® Accession No. AAB46883.1), Super IL-2 (e.g., see Levin et al., Nature 484:529-33, 2012), or IL-15 (e.g., GenBank® Accession No. AAI00963.1 or aa 10-127 of GenBank® Accession No. AAI00963.1). In specific examples, the fusion protein can include leptin and IL-2, or leptin and IL-15. In some examples, the metabolic modulatory protein of the fusion protein is directly attached to a cytokine protein, such as at either the N-terminus or the C-terminus. In some examples (e.g., oncolytic viruses comprising a nucleic acid that can code for a fusion protein comprising a metabolic modulatory protein and a cytokine), the nucleic acid encoding the metabolic modulatory protein portion and the nucleic acid encoding the further portion (e.g., cytokine) can be linked indirectly through the use of a nucleic acid that codes for a linker, such as a peptide linker composed of at least 5, at least 10, at least 15 or at least 20 amino acids, such as 5, 6, 7, 8, 9, 10, 11, 12, 13, 14, 15, 16, 17, 18, 19 or 20 amino acids. In some examples the linker can be flexible. In one example the linker can be a polyalanine. In one example the linker can be a flexible linker, such as one that includes Gly and Ser residues (e.g., GSG, GSGSGS or GGSGGGGSGG). In specific examples, the fusion protein is leptin-GSG-IL-2, or leptin-GSG-IL-15.

2. Exemplary Oncolytic Viruses

The disclosed recombinant OVs can be generated from any OV. OVs are viral strains that can infect and kill malignant cells (oncolysis) while sparing their normal counterparts. Oncolysis can be either a natural property of the virus (naturally occurring OVs, e.g., reovirus) or a consequence of manipulation of the viral genome (genetically engineered OVs, e.g., adenovirus).

In one example, a recombinant OV is a DNA virus, such as a double stranded DNA (e.g., Herpes simplex virus (HSV) (such as HSV-1), vaccinia virus, or adenovirus) or single strand DNA virus (e.g., parovirus and chicken anemia virus, such as H-1PV). Exemplary HSV OVs include T-VEC (e.g., to treat melanoma), G207 (e.g., to treat glioma), NV1020 (e.g., to treat CRC), HFA10 (e.g., to treat breast, head and neck and pancreatic cancer). Exemplary vaccinia OVs include vvDD (TK mutant strain), JX-594 (TK mutant/GM-CSF expressing strain) (e.g., to treat HCC, CRC), and GL-ONC1 (TK mutant/HA expressing strain) (e.g., to treat solid tumors). In one example, a vaccinia virus that includes a genetic deletion of thymidine kinase (TK) and growth factor genes (VGF) is used, such as the Western Reserve laboratory strain Vaccinia virus (see for example Zeh et al., *Mol. Ther* 23:202-14, 2015). Exemplary adenovirus OVs include ONYX (E1B55 mutant), Ad5-D24, CFAd, DNX-2401, Ad5/3 D24-GMCSF and CGTG-102, ColoAd1, and Ad5/d hTERT and CD40 ligand expressing strain (e.g., to treat glioma and solid tumors).

In one example, a recombinant OV is an RNA virus, such as a double stranded RNA (e.g., reovirus) or single strand RNA virus (e.g., coxsackie virus, measles virus, Newcastle disease virus, vesicular stomatitis virus, Seneca valley virus, or ECHO).

Other exemplary OVs that can be used in the compositions and methods provided herein include those provided in Fountzilas et al. (*Oncotarget*, 8:102617-39, 2017) Jhawar et al. (*Front. Oncol.*, 7:202, 2017) and Guo et al. (*Front. Oncol.*, 8:555, 2017) (all herein incorporated by reference in their entireties). In some examples, the recombinant OV can be a lentivirus, a mengovirus, or a myxomavir.

Methods of Using Recombinant Oncolytic Viruses

The recombinant OVs provided herein, for example generated using the disclosed methods, can be used in cancer immunotherapy, for example to treat a tumor in vivo. In some examples, the cancer can comprise melanoma, hepatocellular carcinoma, breast cancer, lung cancer, peritoneal cancer, prostate cancer, bladder cancer, ovarian cancer, leukemia, lymphoma, renal carcinoma, pancreatic cancer, epithelial carcinoma, gastric cancer, colon carcinoma, duodenal cancer, pancreatic adenocarcinoma, mesothelioma, glioblastoma multiform, astrocytoma, multiple myeloma, prostate carcinoma, hepatocellular carcinoma, cholangiosarcoma, pancreatic adenocarcinoma, head and neck squamous cell carcinoma, colorectal cancer, intestinal-type gastric adenocarcinoma, cervical squamous-cell carcinoma, osteosarcoma, epithelial ovarian carcinoma, acute lymphoblastic lymphoma, myeloproliferative neoplasms, or sarcoma. In some examples, the cancer cell can be present in an organ of the subject selected from the group consisting of: the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In some examples, the cancer can be metastatic.

Solid and liquid tumors can be treated with the disclosed methods. Specific examples of tumors that can be treated include, but are not limited to, a leukemia, lymphoma, pancreatic cancer, colorectal cancer, melanoma, cervical cancer, lung cancer, ovarian cancer, bladder cancer, breast cancer, prostate cancer, HCC, RCC, or head and neck cancer. In one example, the cancer is melanoma. In one example, the cancer is breast cancer. In one example, the cancer is an adenocarcinoma. Other examples are provided herein.

Provided herein are methods of treating a tumor (such as a cancer) in a subject (such as a mammalian subject, such as a human or veterinary subject), increasing T cell infiltration into a tumor (or tumor microenvironment), increasing the metabolic activity of T cells in a tumor or tumor microenvironment, or combinations thereof. Such methods can include administering a therapeutically effective amount of one or more recombinant OVs disclosed herein to the subject (for example systemically or intratumorally), thereby treating the tumor. For example, expression of a metabolic modulating protein (such as one or more of leptin, insulin, chemerin, and IGF-1) by the OVs in tumor cells infected by the recombinant OVs, can kill the tumor cells and increase T cell activity in the vicinity of the tumor. In some examples, instead of using a recombinant OV, the methods can include administering (for example systemically or intratumorally) a therapeutically effective amount of one or more metabolic modulating proteins or nucleic acid molecules encoding the protein(s) to the subject, thereby treating the tumor. For example, expression of the metabolic modulating protein (such as one or more of leptin, insulin, chemerin, and IGF-1) in the vicinity of tumor cells can have anti-tumor effects, for example by increasing T cell activity in the vicinity of the tumor.

In some examples, such methods further include administering a therapeutically effect amount of one or more additional anti-cancer agents, such as chemotherapy (e.g., an alkylating agent, antimetabolite, a hormone, or a hormone antagonist), radiotherapy, a biologic (e.g., monoclonal antibody, such as one that specifically binds and antagonizes PD-1 or PD-L1, or a T cell agonist, such as mAb agonist of 4-1BB, OX40, or GITR), surgery, or combinations thereof. In some examples, such subjects are also administered an effective amount of IL-2 (such as 10,000 to 100,000 units/kg body weight) to the subject before, after, or both before and after, administering the disclosed recombinant OVs (or metabolic modulating protein or nucleic acid molecule encoding the protein).

For example, an effective amount of the disclosed recombinant OVs (such as at least $1\times10^6$ pfu recombinant OVs, at least $2\times10^6$ pfu recombinant OVs, at least $5\times10^6$ pfu recombinant OVs, or at least $1\times10^7$ pfu recombinant OVs) are administered to the subject, thereby treating a tumor (such as a primary tumor and/or a metastasis) in the subject. In some embodiments, an effective amount of a recombinant OV of this disclosure, administered to a subject can comprise from about $1\times10^3$ to about $1\times10^{12}$ PFU recombinant OVs, or from about $1\times10^5$ and $1\times10^{10}$ PFU recombinant OVs, or from about $1\times10^5$ and $1\times10^8$ PFU recombinant OVs, or from about $1\times10^8$ and $1\times10^{10}$ PFU recombinant OVs, about $1\times10^{11}$ PFU recombinant OVs, $1\times10^{12}$ PFU recombinant OVs, $1\times10^{13}$ PFU recombinant OVs, $1\times10^{14}$ PFU recombinant OVs, or $1\times10^{15}$ PFU recombinant OVs.

In some examples, the recombinant OVs are administered intravenously. In some examples, the recombinant OVs are administered intratumorally. In some examples, the recombinant OVs are administered subdermally. In some examples, the recombinant OVs are administered via routes such as rectal, intraurethral, intravaginal, intranasal, intrathecal, or intraperitoneal.

In some examples the subject administered the disclosed recombinant OVs was previously treated unsuccessfully with a chemotherapy, radiation therapy, biologic therapy, or combinations thereof (e.g., the tumor in the subject did not significantly decrease in size or even increased in size, and/or metastasized). In some examples the subject has a tumor that was not responsive to a PD-1 antagonist or a PD-L1 antagonist (e.g., the tumor in the subject did not significantly decrease in size or even increased in size, and/or metastasized), such as an antibody that specifically binds and antagonizes PD-1 or PD-L1, such as Atezolizumab, MPDL3280A, BNS-936558 (Nivolumab), Pembrolizumab, Pidilizumab, CT011, AMP-224, AMP-514, MEDI-0680, BMS-936559, BMS935559, MEDI-4736, MPDL-3280A, MSB-0010718C, MGA-271, Indoximod, Epacadostat, BMS-986016, MEDI-4736, MEDI-4737, MK-4166, BMS-663513, PF-05082566 (PF-2566), Lirilumab, and Durvalumab. In some examples the subject has a tumor that was not responsive to a T cell agonist, such as an agonist of 4-1BB, OX40, or GITR (e.g., the tumor in the subject did not significantly decrease in size or even increased in size, and/or metastasized) (particular examples of such reagents are provided herein).

In some examples, the method includes monitoring T cells in the tumor microenvironment, for example determining the number of cells, determining or measuring the mitochondrial activity (e.g., oxidative metabolism), and determining or measuring the mitochondrial mass of the TILs.

In some examples, the method includes monitoring tumor growth in response to treatment.

Coding Sequences

A vector, including a recombinant OV, can be used to express a metabolic modulating protein in the area of a tumor (or even in a tumor cell), wherein the vector that includes a nucleic acid molecule encoding one or more metabolic modulating proteins (such as one or more of leptin, insulin, chemerin, and IGF-1, which may be part of a fusion protein that includes a cytokine). Examples of vectors that can be used include plasmids, viral vectors, such as an OV.

Nucleic acid molecules include DNA, cDNA and RNA sequences which encode a peptide. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA.

Codon preferences and codon usage tables for a particular species can be used to engineer isolated nucleic acid molecules encoding a metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1; in one example one or more of leptin, insulin, chemerin, and IGF-1) that take advantage of the codon usage preferences of that particular species. For example, the metabolic modulating protein (such as one or more of leptin, insulin, chemerin, and IGF-1) expressed from the vector(s) can be designed to have codons that are preferentially used by a particular organism of interest (e.g., in one whom the therapy is introduced).

A nucleic acid encoding a metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], which may be part of a fusion protein that includes a cytokine) can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). A wide variety of cloning and in vitro amplification methodologies are known. In addition, nucleic acids encoding sequences encoding a metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], which may be part of a fusion protein that includes a cytokine) can be prepared by cloning techniques. Examples of appropriate cloning and sequencing techniques, and instructions are found in Sambrook et al. (ed.), Molecular Cloning: A Laboratory Manual 2nd ed., vol. 1-3, Cold Spring Harbor Laboratory Press, Cold Spring, Harbor, N.Y., 1989, and Ausubel et al., (1987) in "Current Protocols in Molecular Biology," John Wiley and Sons, New York, N.Y.

Nucleic acid sequences encoding a metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], which may be part of a fusion protein that includes a cytokine) can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is generally limited to sequences of about 100 bases, longer sequences may be obtained by the ligation of shorter sequences.

In one example, a metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], which may be part of a fusion protein that includes a cytokine) is prepared by inserting the cDNA which encodes the protein into a vector. The insertion can be made so that the protein(s) is read in frame so that the protein(s) is produced. Techniques for preparing recombinant vectors (e.g., plasmid or virus) containing a heterologous nucleic acid sequence encoding the protein are known.

The nucleic acid coding sequence for a metabolic modulating protein (such as one or more of leptin, insulin, chemerin, and IGF-1, which may be part of a fusion protein that includes a further protein, such as a cytokine) can be inserted into an expression vector including, but not limited to a plasmid, virus or other vehicle that can be manipulated to allow insertion or incorporation of sequences and can be expressed (e.g., in a tumor cell). Methods of expressing coding sequences from a vector are known. The expression vector can contain additional elements necessary for the transfer and subsequent replication of the expression vector containing the metabolic modulating protein (such as one or more of leptin, insulin, chemerin, and IGF-1, which may be part of a fusion protein that includes a cytokine) coding sequence in the cell. Examples of such elements include, but are not limited to, origins of replication and selectable markers, such as a thymidine kinase gene or an antibiotic resistance marker.

Nucleic acid sequences encoding metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], which may be part of a fusion protein that includes a cytokine) can be operatively linked to expression control sequences. An expression control sequence operatively linked to a metabolic modulating protein (such as one or more of leptin, insulin, chemerin, and IGF-1, which may be part of a fusion protein that includes a cytokine) coding sequence is ligated such that expression of the metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1]) protein coding sequence is achieved under conditions compatible with the expression control sequences. Exemplary expression control sequences include, but are not limited to appropriate promoters, enhancers, transcription terminators, a start codon (i.e., ATG) in front of a metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], which may be part of a fusion protein that includes a cytokine)-encoding gene, splicing signal for introns, maintenance of the correct reading frame of that gene to permit proper translation of mRNA, and stop codons. Examples of expression control elements that can be used include, but are not limited to, lac system, operator and promoter regions of phage lambda, and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP- 4), insulin, and/or IGF-1 [such as one or more of leptin, insulin, chemerin, and IGF-1], which may be part of a fusion protein that includes a cytokine) protein in the cell. In one example, the promoter is a 7.5 promoter. In one example, an IRES is used to drive expression. In some examples, two promoters are used.

Viral vectors can be prepared that encode a metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], which may be part of a fusion protein that includes a cytokine) protein. Exemplary viral vectors that can be used include, but are not limited to, polyoma, SV40, adenovirus, vaccinia virus, adeno-associated virus, herpes viruses including HSV and EBV, Sindbis viruses, alphaviruses and retroviruses of avian, murine, and human origin. Baculovirus (*Autographa californica* multinuclear polyhedrosis virus; AcMNPV) vectors can also be used. Other suitable vectors include orthopox vectors, avipox vectors, fowlpox vectors, capripox vectors, suipox vectors, lentiviral vectors, alpha virus vectors, and poliovirus vectors. Specific exemplary vectors are poxvirus vectors such as vaccinia virus, fowlpox virus and a highly attenuated vaccinia virus (MVA), adenovirus, baculovirus and the like. Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Other viral vectors that can be used include other DNA viruses such as herpes virus and adenoviruses, and RNA viruses such as retroviruses and polio.

Administration of a Metabolic Modulating Protein

In some examples, instead of using a recombinant OV to express the metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], which may be part of a fusion protein that includes a cytokine), metabolic modulating protein or nucleic acid molecules encoding the protein is administered to the subject.

In one example, a vector is used to express a metabolic modulating protein in the area of a tumor, wherein the vector that includes a nucleic acid molecule encoding one or more metabolic modulating proteins (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], which may be part of a fusion protein that includes a cytokine). Examples of vectors that can be used include plasmids, viral vectors, such as a lentiviral vector or retrovirus. In another example, a naked nucleic acid molecule encoding for a metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], which may be part of a fusion protein that includes a cytokine) is administered.

Nucleic acid molecules encoding a native or variant metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], which may be part of a fusion protein that includes a cytokine) can be incorporated into a vector. Nucleic acid sequences coding for a native or variant a metabolic modulating protein (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1], and IGF-1, which may be part of a fusion protein that includes a cytokine) such as those having at least 90%, at least 92%, at least 95%, at least 96%, at least 97%, at least 98%, or at least 99% sequence identity to those shown in a GenBank® Accession No. provided herein (such as SEQ ID NO: 1, 3, 5, or 7), can be generated. In addition, one of skill can readily construct a variety of clones containing functionally equivalent nucleic acids, such as nucleic acids which differ in sequence but which encode the same protein sequence. In some examples, such a sequence is optimized for expression in a host cell, such as a host tumor used to express the desired protein(s).

Additional Therapies

The subject treated with the disclosed recombinant oncolytic viruses can receive one or more additional therapies, such as one or more of an effective amount of chemotherapy, an effective amount of radiotherapy (for example administration of radioactive material or energy (such as external beam therapy) to the tumor site to help eradicate the tumor or shrink it), an effective amount of a biologic (such as a therapeutic monoclonal antibody, ligand, or aptamer), and surgery (for example surgical resection of the cancer or a portion of it). Thus, in some examples, kits that include one or more of the disclosed recombinant oncolytic viruses and one or more anti-cancer agents (such as a chemotherapeutic or biologic), are provided.

In one example, the subject is further treated with one or more chemotherapeutic agents. Chemotherapeutic agents include any chemical agent with therapeutic usefulness in the treatment of diseases characterized by abnormal cell growth, such as cancer. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, *Clinical Oncology* $2^{nd}$ ed., ©2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993; Chabner and Longo, *Cancer Chemotherapy and Biotherapy: Principles and Practice* (4th ed.). Philadelphia: Lippincott Willians & Wilkins, 2005; Skeel, *Handbook of Cancer Chemotherapy* (6th ed.). Lippincott Williams & Wilkins, 2003). Combination chemotherapy is the administration of more than one agent to treat cancer.

Examples of chemotherapeutic agents that can be used include alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Specific non-limiting examples of alkylating agents are temozolomide and dacarbazine. Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone).

Examples of commonly used chemotherapy drugs that can be used in combination with the disclosed OVs that express one or more metabolic modulatory proteins include Adriamycin, Alkeran, Ara-C, BiCNU, Busulfan, CCNU, Carboplatinum, Cisplatinum, Cytoxan, Daunorubicin, DTIC, 5-fluoruracil (5-FU), Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Additional therapeutic agents that can be used in combination with the disclosed OVs that express one or more metabolic modulatory proteins include microtubule binding agents, DNA intercalators or cross-linkers, DNA synthesis inhibitors, DNA and/or RNA transcription inhibitors, antibodies, enzymes, enzyme inhibitors, gene regulators, angiogenesis inhibitors. These agents (which are administered at a therapeutically effective amount) and treatments can be used alone or in combination. Methods and therapeutic dosages of such agents are known, and can be determined by a skilled clinician.

Microtubule binding agents refers to agents that interact with tubulin to stabilize or destabilize microtubule formation thereby inhibiting cell division. Examples of microtubule binding agents that can be used in conjunction with the disclosed therapies include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

Suitable DNA and/or RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-fluorouracil (5-FU) and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof.

The disclosed methods can further include administering to the subject a therapeutically effective amount of an immunotherapy. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech). The immunotherpautic agent can be a PD-1 antagonist or a PD-L1 antagonist, such as an antibody (such as a monoclonal antibody) that specifically binds PD-1 or PD-L1, such as Atezolizumab, MPDL3280A, BNS-936558 (Nivolumab), Pembrolizumab, Pidilizumab, Durvalumab, CT011, AMP-224, AMP-514, MEDI-0680, BMS-936559, BMS935559, MEDI-4736, MPDL-3280A, MSB-0010718C. The immunotherpautic agent can also be a CTLA-4, LAG-3, or B7-H3 antagonist, such as Tremelimumab, BMS-986016, and MGA271.

In some examples, the additional therapeutic agent administered is a T cell agonist, such as an agonist of 4-1BB (CD137), OX40, and/or GITR. OX40 is a type 1 transmembrane glycoprotein. The human OX40 sequence includes an extracellular N-terminal portion of 191 aa, and an intracellular region of 36 aa. OX40L is a type II transmembrane glycoprotein. In one example, an OX40 agonist is an anti-OX40 antibody, such as a monoclonal antibody (mAb) (e.g., PR-04518600, MEDI-6469, MEDI-0562, MEDI-6383, MOXR-0916, BMS 986178, or GSK3174998). Mimicking the natural OX40 ligand (OX40L), anti-OX40 monoclonal antibody selectively binds to and activates the OX40 receptor. In one example, an OX40 agonist is an OX40 ligand, OX40L, such as a natural ligand (such as a human OX40L). In one example, an OX40 agonist is a OX40 aptamer. 4-1BB (CD137/TNFSF9) belongs to the TNF receptor family, which includes multiple T cell costimulatory receptors. It is found on T cells, including CD8 and CD4 T cells. 4-1BB's expression on both T cells and antigen presenting cells, coupled with its capacity to promote survival, expansion, and enhanced effector function of activated T cells, makes it target for tumor immunotherapy. In one example, a 4-1BB agonist is a 4-1BB agonist antibody, such as a mAb. Specific agonist mAbs that can be used with the disclosed methods include PF-05082566 (utomilumab), and BMS-663513 (Urelumab). In one example, a 4-1BB agonist is a 4-1BB ligand (4-1BBL), such as a natural 4-1BBL (such as the human 4-1IBBL) or a streptavidinated 4-1BBL (SA-4-1BBL) complex. In one example, a 4-1BB agonist is a 4-1BB aptamer. GITR (glucocorticoid-induced tumor necrosis factor (TNF) receptor, or TNFRSF18) is a type I transmembrane protein with homology to other TNF receptor family members such as OX40, CD27, and 4-1BB. GITR is normally expressed at low levels on resting CD4+foxp3− and CD8+ T cells, but is constitutively expressed at high levels on CD4+CD25+foxp3+ regulatory T cells (Tregs). Its ligand, GITRL (TNFSF18) is also a member of the TNF superfamily and is predominantly expressed by activated antigen presenting cells (APCs), including DCs, macrophage and activated B cells. In one example, a GITR agonist is a GITR agonist antibody, such as a mAb. Specific GITR agonist mAbs that can be used with the disclosed methods include DTA-1, TRX518, MK-4166, MK-1248, AMG 228, INCAGN01876, GWN323 (from Novartis), CK-302 (from Checkpoint Therapeutics) and BMS-986156. In one example, a GITR agonist is a GITR ligand (GITRL), such as a natural GITRL or a multivalent GITR ligand fusion protein. In one example, the GITR agonist is MEDI1873, a hexameric GITRL molecule with a human IgG1 Fc domain. In one example, GITR agonist is a GITR aptamer.

Non-limiting examples of anti-angiogenic agents include molecules, such as proteins, enzymes, polysaccharides, oligonucleotides, DNA, RNA, and recombinant vectors, and small molecules that function to reduce or even inhibit blood vessel growth. Examples of suitable angiogenesis inhibitors that can be used with the disclosed methods include, without limitation, angiostatin K1-3, staurosporine, genistein, fumagillin, medroxyprogesterone, suramin, interferon-alpha, metalloproteinase inhibitors, platelet factor 4, somatostatin, thromobospondin, endostatin, thalidomide, and derivatives and analogs thereof. For example, in some embodiments the anti-angiogenesis agent is an antibody that specifically binds to VEGF (e.g., Avastin, Roche) or a VEGF receptor (e.g., a VEGFR2 antibody). In one example the anti-angiogenic agent includes a VEGFR2 antibody, or DMXAA (also known as Vadimezan or ASA404; available commercially, e.g., from Sigma Corp., St. Louis, MO) or both. The anti-angiogenic agent can be bevacizumab, sunitinib, an anti-angiogenic tyrosine kinase inhibitors (TKI), such as sunitinib, xitinib and dasatinib. These can be used individually or in any combination.

Exemplary kinase inhibitors that can be used with the disclosed methods include Gleevac, Iressa, and Tarceva, sunitinib, sorafenib, anitinib, and dasatinib that prevent phosphorylation and activation of growth factors. Antibodies that can be used include Herceptin and Avastin that block growth factors and the angiogenic pathway. These can be used individually or in combination.

In some examples, the additional therapeutic agent administered is a biologic, such as a monoclonal antibody, for example, 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, Tacatuzumab tetraxetan, Taplitumomab paptox, Tenatumomab, TGN1412, Ticilimumab (tremelimumab), Tigatuzumab, TNX-650, Trastuzumab, Tremelimumab, Tucotuzumab celmoleukin, Veltuzumab, Volociximab, Votumumab, Zalutumumab, or combinations thereof. In some examples, the therapeutic antibody is specific for PD-1 or PDL-1.

In some examples, the subject is also administered an effective amount of nonmyeloablative chemotherapy or radiotherapy. For example, the subject may receive an effective amount of nonmyeloablative chemotherapy, such as administration of one or more of cisplatin, fludarabine, idarubicin, melphalan, ara-C, 2-chlorodeoxyadenosine, antithymocyte globulin, and cyclophosphamide (such as 10 to 50 mg/kg body weight). In some examples, the subject receives an effective amount of solid tumor irradiation, thymic irradiation, or total body irradiation (e.g., 2 Gy), or combinations thereof.

In some examples, following administration of the recombinant oncolytic virus, the subject is administered one or more of an effective amount of tacrolimus, cyclosporine, and/or methotrexate.

In some examples, the recombinant OVs and the one or more additional therapies can be, for example, and not by way of limitation, can be administered concurrently to the subject being treated, or can be administered at the same time or sequentially in any order or at different points in time.

The additional therapy can be administered, in various examples, in a liquid dosage form, a solid dosage form, a suppository, an inhalable dosage form, an intranasal dosage form, in a liposomal formulation, a dosage form comprising nanoparticles, a dosage form comprising microparticles, a polymeric dosage form, or any combinations thereof. In certain cases, the additional therapy can be administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the additional therapy can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months). In certain cases, a method of treating a subject having a cancer can include administering, to the subject, an effective amount of a recombinant OV, e.g., a recombinant vaccinia virus, of this disclosure, comprising one or more nucleic acids that can code for one or more metabolic modulating proteins.

Clinical Response

Such methods can treat the tumor in the subject by reducing the volume or weight of the tumor, reducing the number of metastases, reducing the size or weight of a metastasis, or combinations thereof. In some examples a metastasis is cutaneous or subcutaneous. Thus, in some examples, administration of a disclosed recombinant oncolytic virus (alone or in combination with another anti-cancer therapy) treats a tumor in a subject by reducing the size or volume of the tumor by at least 10%, at least 20%, at least 30%, at least 40%, at least 50%, at least 60%, at least 70%, at least 75%, at least 80%, at least 90%, at least 95%, at least 98% or at least 99%, for example as compared to no administration of a disclosed recombinant oncolytic virus or administration of a recombinant oncolytic virus not containing a metabolic modulating protein coding sequence (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1]). In some examples, administration of a disclosed recombinant oncolytic virus treats a tumor in a subject by reducing the weight of the tumor by at least 10%, at least 20%, at least 30%, at least 40%, at least 50%, at least 60%, at least 70%, at least 75%, at least 80%, at least 90%, at least 95%, at least 98% or at least 99%, for example as compared to no administration of a disclosed recombinant oncolytic virus or administration of a recombinant oncolytic virus not containing a metabolic modulating protein coding sequence (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1]). In some examples, administration of a disclosed recombinant oncolytic virus treats a tumor in a subject by reducing the size or volume of a metastasis by at least 10%, at least 20%, at least 30%, at least 40%, at least 50%, at least 60%, at least 70%, at least 75%, at least 80%, at least 90%, at least 95%, at least 98% or at least 99%, for example as compared to no administration of a disclosed recombinant oncolytic virus or administration of a recombinant oncolytic virus not containing a metabolic modulating protein coding sequence (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1]). In some examples, administration of a disclosed recombinant oncolytic virus treats a tumor in a subject by reducing the number of metastases by at least 10%, at least 20%, at least 30%, at least 40%, at least 50%, at least 60%, at least 70%, at least 75%, at least 80%, at least 90%, at least 95%, at least 98% or at least 99% for example as compared to no administration of a disclosed recombinant oncolytic virus or administration of a recombinant oncolytic virus not containing a metabolic modulating protein coding sequence (such as an adipokine (e.g., leptin, chemerin, adiponectin, apelin, IL-6, MCP-1, PAI-1, RBP4, TNFα, visfatin, omentin, vaspin, progranulin and/or CTRP-4), insulin, and/or IGF-1 [such as one or more of leptin, insulin, chemerin, and IGF-1]). In some examples, combinations of these effects are achieved.

Compositions and Kits

Also provided are compositions and kits that can be used with the disclosed methods. In some examples, the composition or kit includes one or more disclosed recombinant oncolytic viruses that expresses a metabolic modulating protein, for example with a pharmaceutically acceptable carrier. In one example, the OV expresses an adipokine (e.g., leptin, chemerin, adiponectin, apelin, IL-6, MCP-1, PAI-1, RBP4, TNFα, visfatin, omentin, vaspin, progranulin and/or CTRP-4). In one example, the OV expresses insulin and/or IGF-1. In one example, the OV expresses leptin. The adipokine, insulin and/or IGF-1 can be part of a fusion protein that further includes a second protein, such as a gamma chain cytokine (e.g., L-2 or IL-15). In some examples the second protein can be a cytokine protein, such as a chemokine, an interferon, an interleukin, a lymphokine, a tumour necrosis factor, or a fusion protein comprising any combinations thereof. Other examples are provided above.

In one example, the OV expresses leptin, insulin, chemerin, or IGF-1 (which can be part of a fusion protein that further includes a gamma chain cytokine, such as IL-2 or IL-15). In a specific example, the OV is talimogene laherparepvec (T-VEC). In a specific example, the OV is Western Reserve strain Vaccinia virus. In a specific example, the OV is vaccinia, and the one or more metabolic modulating proteins is leptin. In a specific example, the OV is Western Reserve strain Vaccinia virus, and the one or more metabolic modulating proteins is leptin. In a specific example, the OV is Western Reserve strain Vaccinia virus, and the one or more metabolic modulating proteins is a leptin-IL-2 or leptin-IL-15 fusion protein (wherein the leptin and cytokine may be joined by a linker).

The kits can include additional reagents, such as one or more anti-cancer reagents, such as a chemotherapeutic, biologic, or combination thereof. In some examples, in a kit, the OV and anti-cancer reagents are present in separate containers.

In one example, the kit further includes a biologic, such as a PD-1 antagonist; a PD-L1 antagonist; a CTLA4 antagonist; a T cell agonist; or combinations thereof. In one example, the PD-1 antagonist, PD-L1 antagonist, CTLA4 antagonist, and T cell agonist, are mAbs. Exemplary T cell agonists include agonists of 4-1BB, agonists of OX40, and agonists GITR, such as a mAb, aptamer, or ligand for these receptors. Exemplary agonists of 4-1BB that can be included in the kit include mAbs, such as PF-05082.566 (utomilumab) or BMS-663513 (Urelumab), or a ligand (e.g., 4-1BBL or SA-4-1BBL). Exemplary agonists of OX40 that can be included in the kit include a mAb (e.g., PF-04518600, MEDI6469, MEDI0562, MEDI6383, MOXR0916, BMS 986178, or GSK3174998), or a ligand (e.g., OX40L). Exemplary agonists of agonists GITR that can be included in the kit include a GITR agonist mAb, such as DTA-1, TRX518, MK-4166, MK-1248, AMG 228, INCAGN01876, GWN323 (from Novartis), CK-302 (from Checkpoint Therapeutics) or BMS-986156. Exemplary agonists of GITR that can be included in the kit include a GITR ligand (GITRL), such as a natural GITRL or a multivalent GITR ligand fusion protein, such as MEDI1873.

Also provided are containers that include a composition disclosed herein, such as an OV provided herein. In some embodiments, the container is a syringe. In some examples, the syringe includes a needle. The plunger in a syringe can have a stopper to prevent the plunger from being accidentally removed during aspiration. Disposable syringes generally contain a single dose of vaccine. The syringe can have a tip cap to seal the tip prior to attachment of a needle. In non-limiting examples, the tip cap is made of rubber, such as a butyl rubber.

In other embodiments, the container is a vial. In some examples, the vial is made of glass, such as a colorless glass, for example borosilicate. In other examples, the vial is made of plastic. The vial can include a stopper, such as a rubber stopper, or a cap, such as cap adapted to enable insertion of a syringe. In some examples, the vial includes a single dose of the composition. In other examples, the vial includes multiples doses of the composition, such as 2, 3, 4, 5, 6, 7, 8, 9 or 10 or more doses of the composition. Generally, the vial is sterilized prior to adding the composition.

Also provided are kits that include a container disclosed herein. In some embodiments, the kits includes a vial (such as a vial containing the composition), a syringe (for example, an empty syringe or a syringe containing the composition), a needle, or any combination thereof. The compositions can be in a suspension, such as in PBS or other pharmaceutically acceptable carrier. Alternatively, the compositions can be in a dried or powered form, such as lyophilized or freeze dried, which can then be reconstituted by an end user (for example with PBS or other pharmaceutically acceptable carrier). In some examples the containers can include a pharmaceutically acceptable carrier, such as PBS, or the pharmaceutically acceptable carrier, such as PBS, can be in a separate container (for example if the compositions are freeze-dried or lyophilized). In some examples, the containers in the kit further include one or more stabilizers. In some examples, the kits also include a device that permits administration of the composition to a subject. Examples of such devices include a syringe. A kit can be packaged (for example, in the same box) with a leaflet including details of the composition, such as instructions for administration and/or details of the OVs within the composition.

Example 1

Materials and Methods

This example describe materials and methods used to generate the results described in the Examples below.

Mice

C57/BL6 mice and Pten$^{f/f}$Braf$^{V600E}$Tyr$^{Cre.ER}$ mice were obtained from Jackson Laboratories and bred in house.

Tumor Lines

Tumor experiments were conducted using a single-cell clone derived from a melanoma tumor formed from a Pten$^{f/f}$Braf$^{V600E}$Tyr$^{Cre.ER}$ painted with tamoxifen (clone 24). The cDNA for leptin was obtained from OriGene and transfected into clone 24 followed by hygromycin selection (an empty vector plasmid was used as a control). Single cell clones were selected and grown as cell line CL24$^{hygro}$ for control plasmid and CL24$^{leptin}$ for leptin expressing cell line.

Tumor Models

C57BL/6J mice were injected with CL24$^{hygro}$ or CL24$^{leptin}$ melanoma cell line (250,000 cells intradermally) on day 0 and followed until tumors reach 15 mm in any direction. Tumors were measured every other day with digital calipers and tumor size was calculated by L×W. Tumors were treated with PBS, VV$^{ctrl}$ or VV$^{leptin}$ (2.5×10$^6$ PFU) intratumorally when tumors reached approximately a 20 mm$^2$ and tumor growth was monitored until tumors treated with PBS reached 15 mm in any direction. For CD8 depletion experiments mice were injected every other day starting at day 0 with anti-CD8 (YTS) at 200 ug per mouse. On day 7 mice were injected with CL24$^{hygro}$ or CL24$^{leptin}$ melanoma cell line (250,000 cells intradermally) and followed until tumor reach 15 mm in any direction.

Oncolytic Virus Production

The wild-type Vaccinia virus Western Reserve (WR) strain was obtained from the American Type Culture Collection (BEI Resources). WR.TK-.Luc+ were described previously (Kim et al., *PLoS Med* 2007; 4(12):e353) and were constructed for this work, with the pSC65 plasmid (from Prof. Bernie Moss, NIH) cloned to express firefly luciferase from the viral pSE/L promoter and mouse leptin (Lep) from the p7.5 promoter. This was recombined into the viral TK gene. Vaccinia virus expressing leptin was generated by cloning in the leptin gene using Gibson Cloning (New England BioLabs) into the Vaccinia plasmid. Leptin gene was cloned from a mouse leptin ORF mammalian expression plasmid (Sino Biological Inc.).

T Cell Isolations from Lymph Node and Tumor

Spleen and lymph node CD8+ T cells were isolated from wild-type mice. Tissue was harvested, mechanically disrupted, and incubated with a biotinylated antibody cocktail consisting of antibodies (BioLegend) to B220, CD11b, CD11c, CD16/32, CD19, CD25, CD105, NK1.1, TCRγδ, and CD4. After a wash step, cells were incubated with streptavidin-coated magnetic nanoparticles (BioLegend). After washing, CD8$^+$ cells were isolated by applying a magnetic field and removing untouched cells.

To obtain single-cell suspensions of tumor infiltrating lymphocytes, tumor bearing mice were sacrificed and tumors were harvested. Excised, whole tumors were injected repeatedly using 20G needles with 2 mg/mL collagenase type VI, 2 U/mL hyluronidase (Dispase), and 10 U/mL DNAse I (Sigma) in buffered RPMI with 10% FBS and incubated for 30 min at 37° C. Tumors were then mechanically disrupted between frosted glass slides and filtered to remove particulates, then vortexed for 2 minutes. In many experiments (especially prior to sorting), tumor homogenates were debulked of tumor cells using CD105-biotin mediated magnetic depletion.

Metabolic Assays

T cell metabolic output was measured by Seahorse technology as previously described (Scharping et al., *Cancer Immunol. Res.* 2017; 5:9-16). Briefly, 100,000 T cells were seeded into Cell-Tak-coated XFe96 plates in minimal unbuffered assay media containing 25 mM glucose, 2 mM glutamine, and 1 mM sodium pyruvate. Cells received sequential injections of 2 μM oligomycin, 2 μM FCCP, 10 mM 2-deoxyglucose, and 0.5 μM rotenone/antimycin A.

Single-cell metabolic capacity was assayed by flow cytometry. Specifically, 2-NBD-glucose (Cayman Chemical) and MitoTracker FM dyes (ThermoFisher) were used to assay the propensity of cells to take up glucose or generate intermediates via their mitochondria. Nondraining and draining lymph node or tumor preparations were pulsed with 20 μM 2-NBDG in 5% FBS-containing media for 30 min at 37° C. Cells were surface stained and loaded with MitoTracker FM dyes to measure mitochondrial mass and function.

Immunoblotting

Immunoblotting was performed as previously described (Delgoffe et al., *Mol. Immunol.* 2009; 46(13):2694-8). Leptin antibody was obtained from Mouse Leptin/OB antibody (R&D system BAF498).

ELISA

ELISA plate was coated with 50 uL capture antibody (1:1000 in PBS) and put at 4° C. overnight. Next day plate was washed 3 times with Wash Buffer (1 L PBS+0.05% Tween 20). Plate was Blocked with 200 uL blocking buffer (200 mL PBS+1% BSA) for 1 hour at room temperature. Samples were added (50 μl) in blocking buffer to the wells together with Standard Curve samples. Plate was incubated at room temperature for 2 hours. Secondary antibody was added (1:2000 in blocking buffer) and incubated at room temperature for 1 hour. After one hour HRP streptavidin (1:2000 in blocking buffer) was added and incubated at room temperature for 30 min. 40 μL TMB substrate A and 40 μL TMB substrate B were added to develop samples. Plate was read at 450 nm in a plate reader. Antibodies used for leptin Elisa experiment: Capture Mouse Leptin/OB antibody (R&D systems AF498) and detection antibody Mouse Leptin/OB antibody (R&D system BAF498).

TCR Sequencing

CL24 tumors with different treatments were excised and processed for genomic DNA extraction (DNeasy QIAGEN kit). TCR sequencing was then performed following the immunoSEQ assay (Adaptive Biotechnologies) (Robins et al., Blood 2009; 114(19):4099-107).

Single Cell RNA Sequencing Analysis

CL24 tumors were treated with PBS, $VV^{ctrl}$ or $VV^{leptin}$ ($2.5 \times 10^6$ PFU) intratumorally for 7 days. Tumor infiltrating lymphocytes were isolated and sorted for $CD45^+$ lymphocytes. $CD45^+$ cell were loaded into the Chromium instrument (10× Genomics, Pleasanton, CA), and the resulting barcoded cDNAs were used to construct libraries. The libraries from each sample were then RNA-sequenced. Cell-gene unique molecular identifier counting matrices were generated and analyzed using Seurat (Satija et al., Nat Biotechnol 2015; 33(5):495-502) and were hierarchically clustered using Cluster 3.0 (de Hoon et al., Bioinformatics 2004; 20(9):1453-4).

Example 2

Figure 1B:
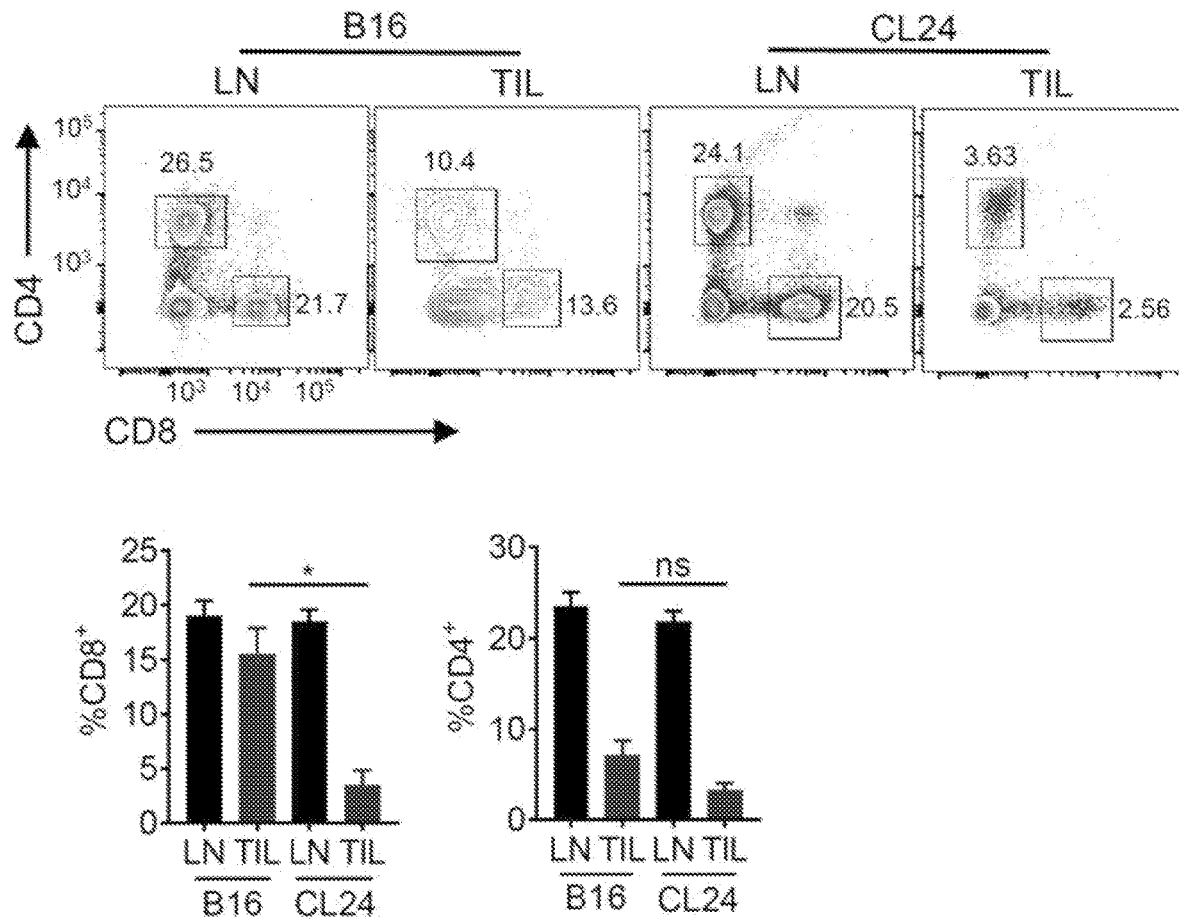
Figure 1C:
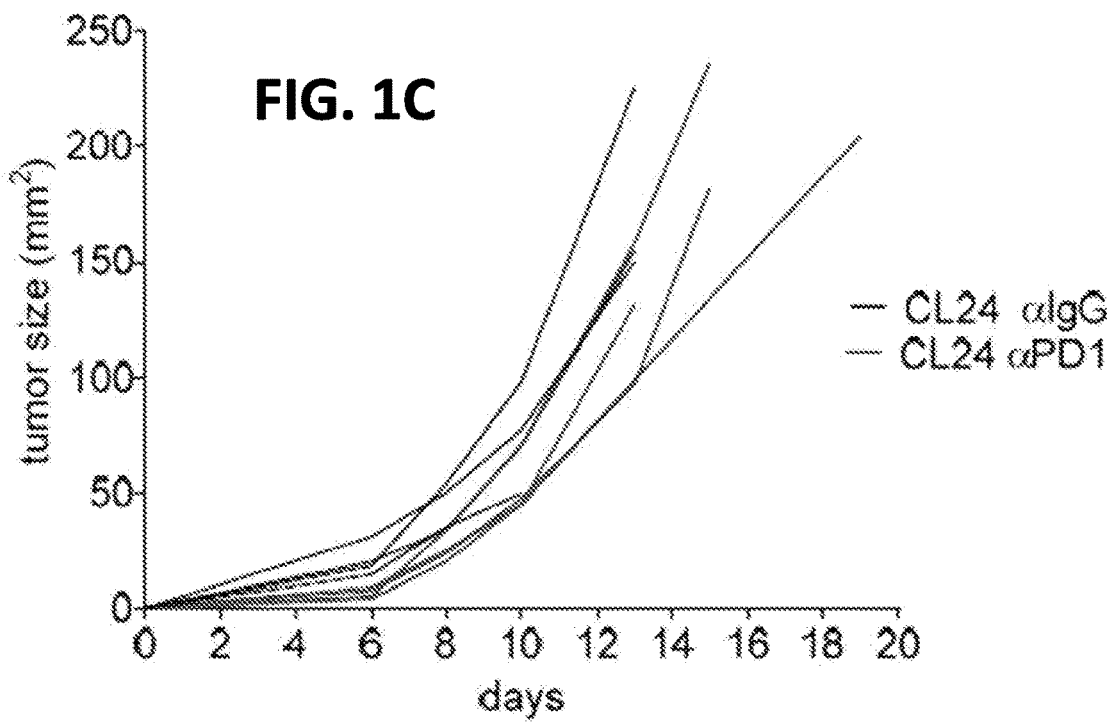

Oncolytic Vaccinia Virus Treatment of Tumors Remodels Tumor Immune Microenvironment While oncolytic viruses like T-vec are FDA approved immunotherapy for cancer treatment (e.g., see Andtbacka et al., J Clin Oncol 2015; 33(25):2780-8), the immune consequences of these agents are unclear. The immune infiltrate induced by oncolytic virus infection was systematically profiled. One major limitation of oncolytic virus therapy is that many viruses, including T-VEC, do not replicate efficiently in hypoxia (Friedman et al., Transl Oncol 2012; 5(3):200-7; Pipiya et al., Gene Ther 2005; 12(11):911-7). Thus, oncolytic Vaccinia virus, which is easily engineered, encodes its own polymerase, and, maintains replicative function in hypoxic tumor cells, was used. The Western Reserve laboratory strain Vaccinia virus was used. This virus harbors a genetic deletion of thymidine kinase and Vaccinia growth factor genes generating a potent oncolytic viral agent (Buller et al., Nature 1985; 317(6040):813-5; Whitman et al., Surgery 1994; 116(2):183-8; Puhlmann et al., Cancer Gene Ther 2000; 7(1):66-73). A melanoma cell line termed clone 24 (CL24), generated from a single-cell of a $Pten^{f/f}Braf^{LSL.V600E}Tyr2^{Cre.ER}$ mouse that developed melanoma after tamoxifen administration (Dankort et al., Nat Genet 2009; 41(5):544-52) was used (FIG. 1A). This cell line is syngeneic to C57/BL6 mice, carries driver mutations common in human melanoma (as opposed to the often used B16). Additionally, this CL24 cell line is poorly infiltrated (FIG. 1B), and is completely insensitive to anti-PD1 monotherapy (FIG. 1C).

Figure 2A:
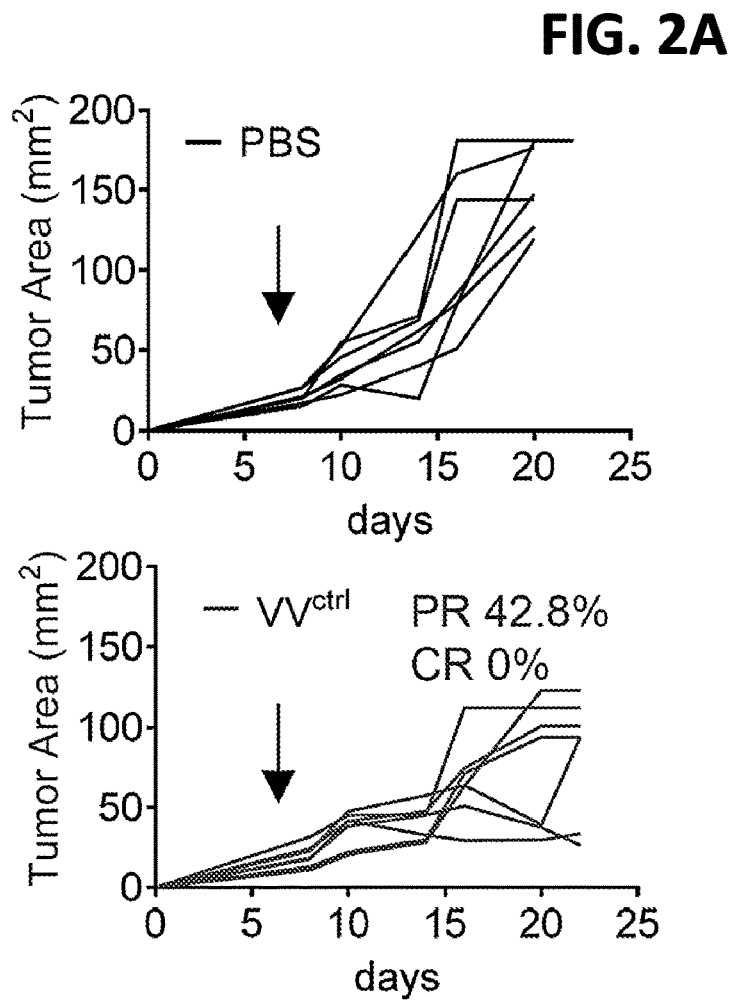
FIGS. 2A-2C. Oncolytic Vaccinia virus has potent immunostimulatory activity that can be enhanced through engineering leptin expression. (A) C57BL/6J mice were injected subdermally with CL24 cells. 5-7 days after tumor cell injection tumors were treated intratumorally with PBS, control Vaccinia virus (VV$^{control}$) at $2.5 \times 10^6$ PFU and tumor growth monitored. Each line represents an individual mouse. (B) Single-cell RNA-seq data for 4000 cells CD45+ sorted cells treated as in (A). Cells were extracted on day 7. Data was generated by unsupervised clustering through Seurat program. (C) t-SNE analysis of PBS and VV$^{ctrl}$ treated mice. Data represents n=2 per condition.
Figure 2B:
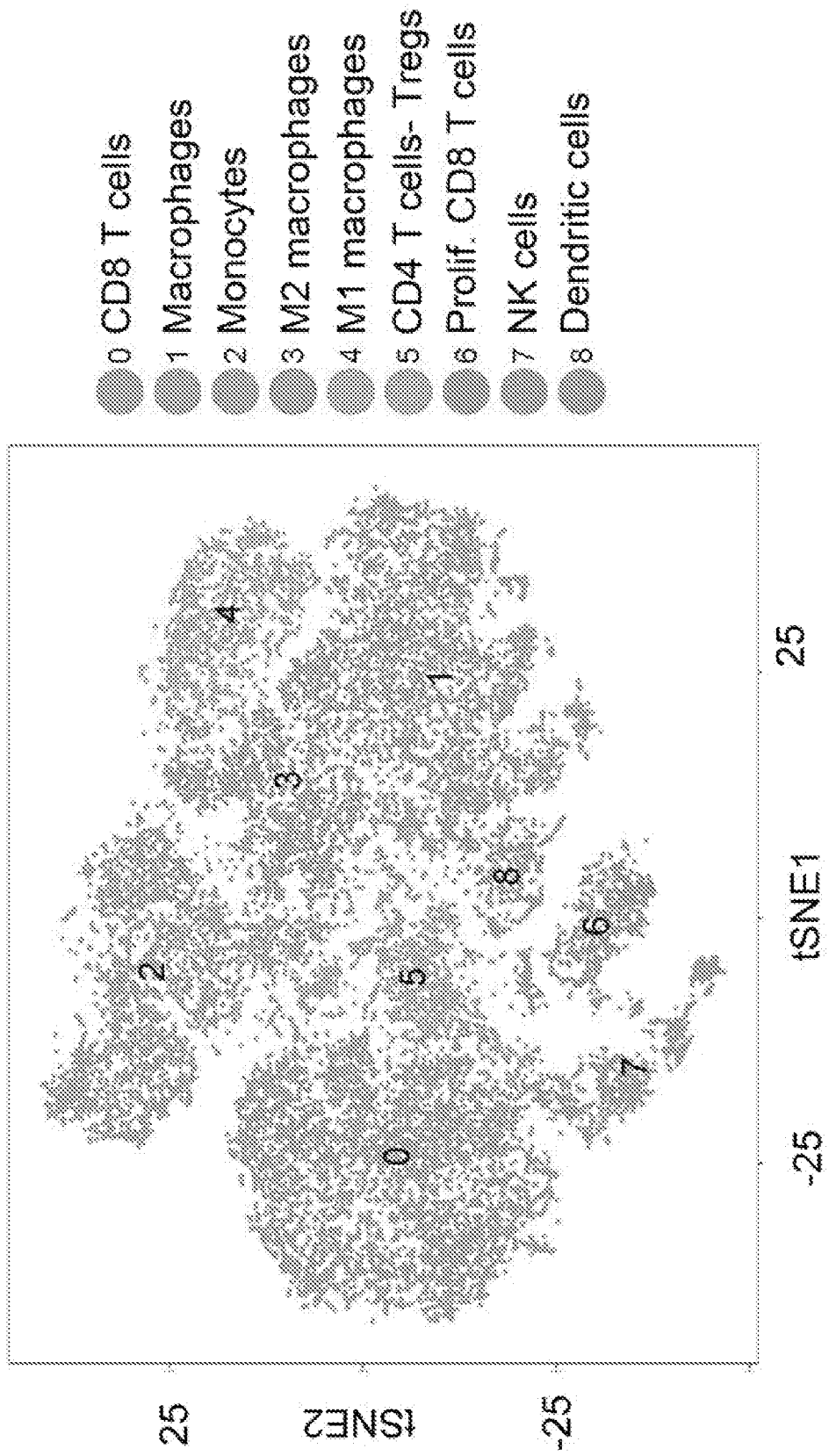
Figure 2C:
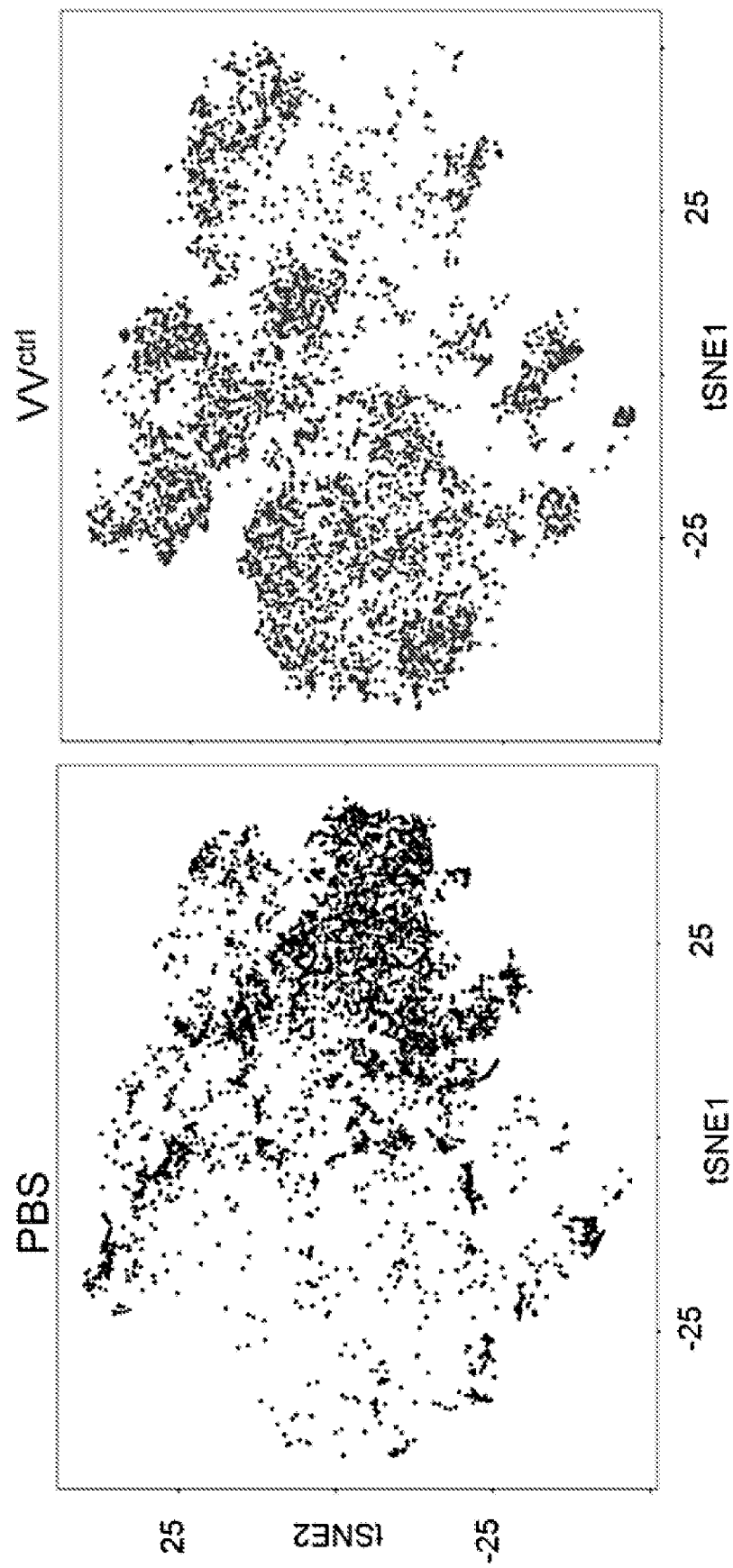
Figure 3A:
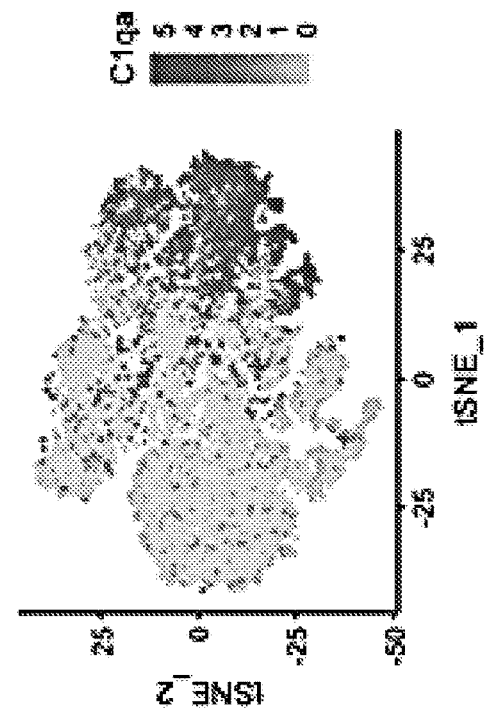
FIGS. 3A-3C. Single cell RNA sequencing analysis from TIL treated with oncolytic vaccinia virus. (A, B) Feature plots of genes defining different lymphocyte populations. Intensity of purple color indicated the normalized level of gene expression. (C) Transcriptome from CD45+ TIL after PBS, VVcontrol, or VV$^{leptin}$ treatment (n=2 per condition) clustered using Seurat (SLM clustering). Each column represent a cell with the give genes most differentially expressed between each cluster.
Figure 3A:
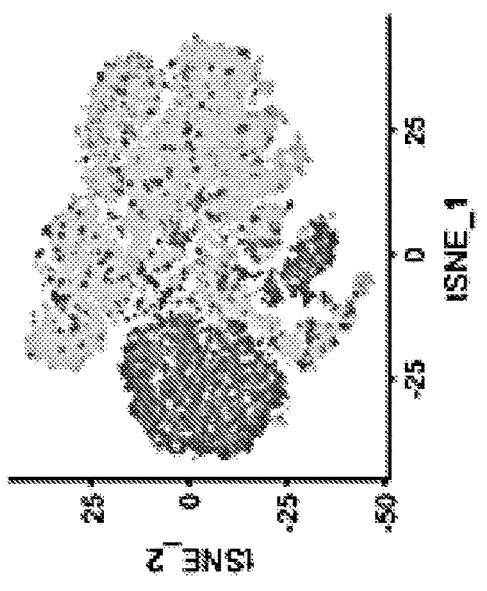
Figure 3A:
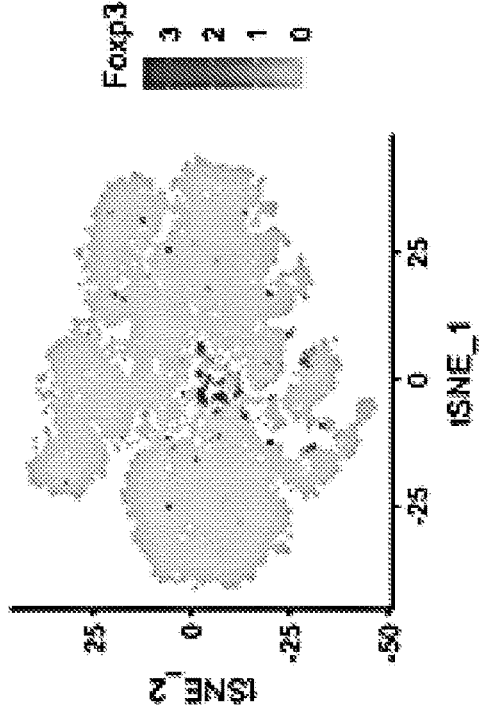
Figure 3A:
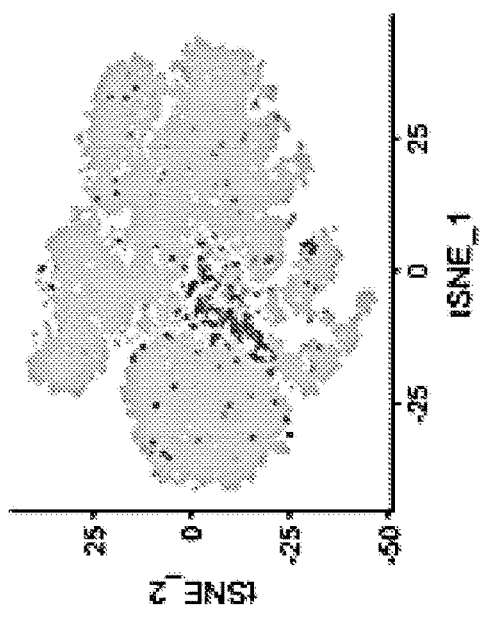
Figure 3B:
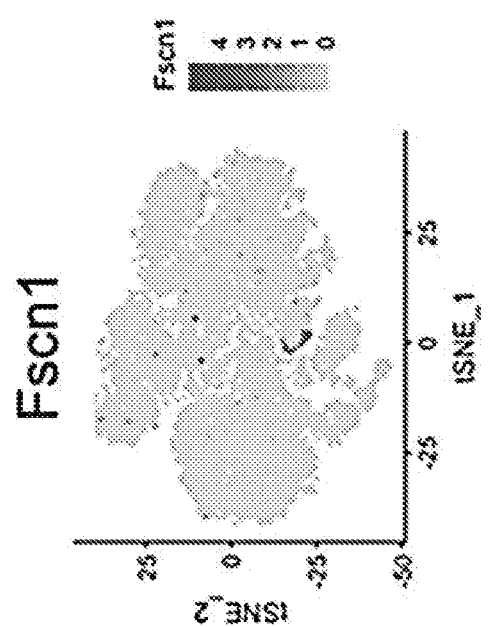
Figure 3B:
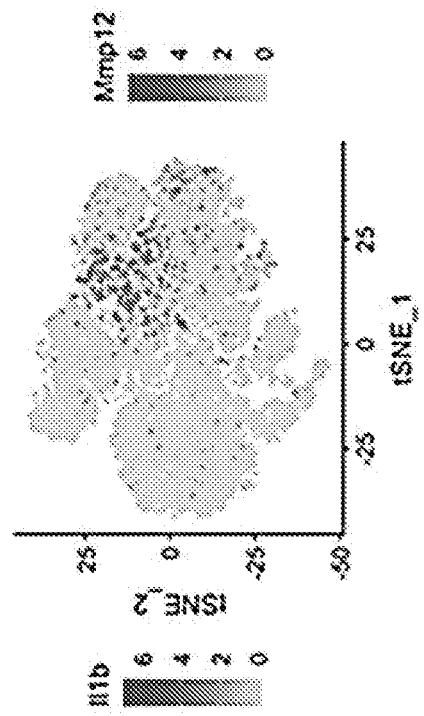
Figure 3B:
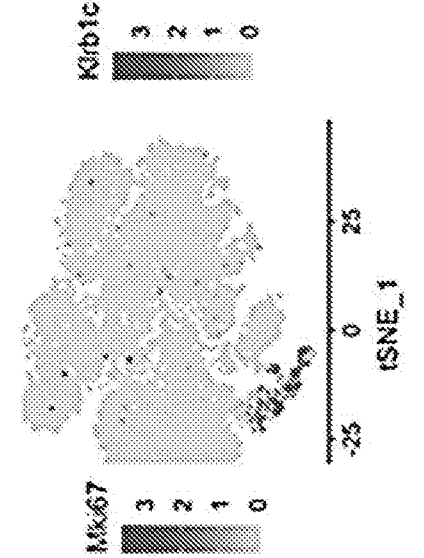
Figure 3B:
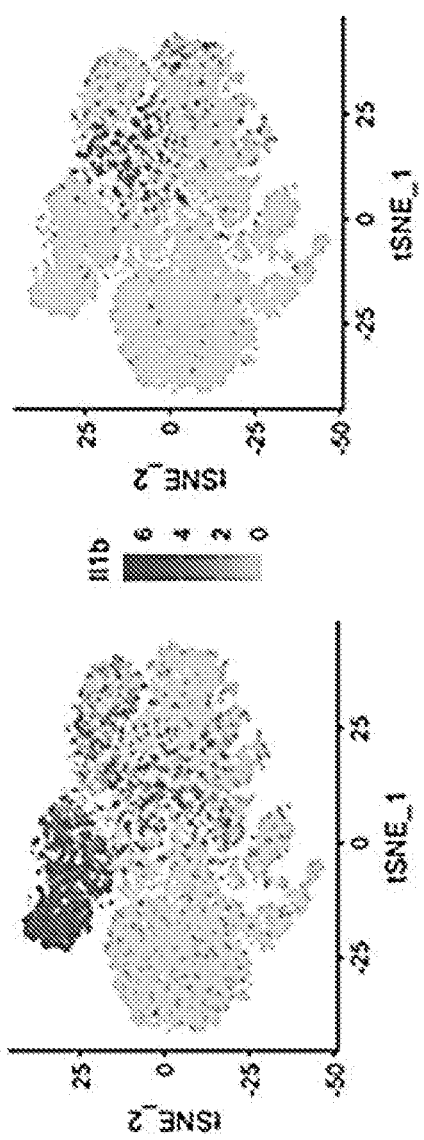
Figure 3B:
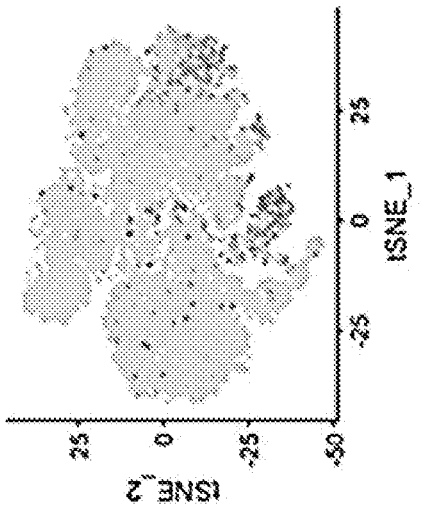
Figure 3C:
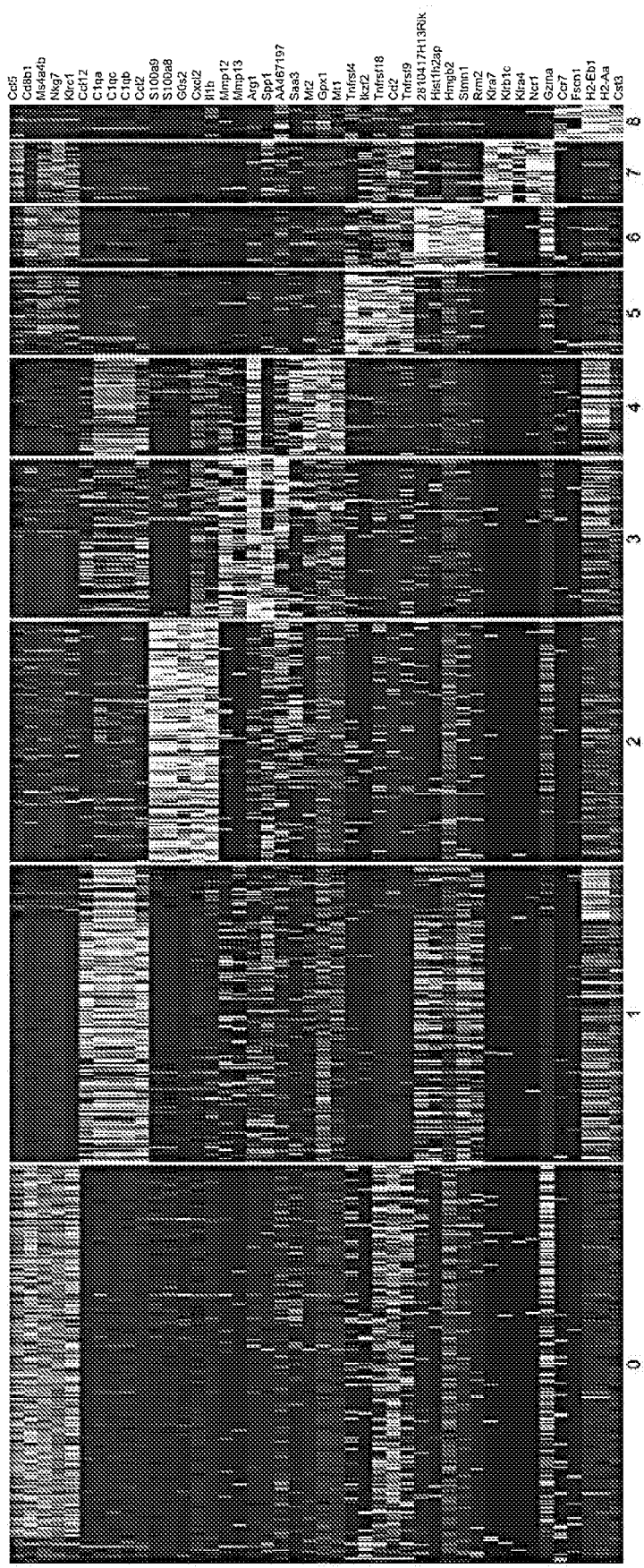

Vaccinia virus was injected intratumorally when tumors reached 4 mm in size, which resulted in substantial tumor regression, but no complete responses (FIG. 2A). To determine the character of the tumor infiltrate induced by oncolytic viruses, single cell RNA-sequencing of the $CD45^+$ tumor infiltrating leukocytes of PBS or Vaccinia infected clone 24 tumors was determined by 10× Genomics profiling. Unsupervised clustering data analysis was used to separate the CD45+ cells into distinct groups of immune populations (FIG. 2B). These immune populations were then classified based on the expression of known markers for each population (FIGS. 3A-3C). Importantly, these analyses were conducted when tumors had not yet regressed. This data identified known immune cell populations when analyzed in aggregate, however subsetting based on treatment group revealed that Vaccinia virus oncolytic immunotherapy induced striking changes in the tumor immune microenvironment (FIG. 2C). Vaccinia infected tumors showed a massive influx of new, effector and effector like $CD8^+$ T cells, M1 macrophages, and a loss of dysfunctional or suppressive cells like MDSC, M2 macrophages, exhausted T cells, and regulatory T cells (FIG. 2C). Thus, oncolytic Vaccinia virus induces a dramatic remodeling of the tumor immune microenvironment, but one that ultimately succumbs to tumor-induced immune suppression and eventual outgrowth (FIG. 2A).

Example 3

Figure 4A:
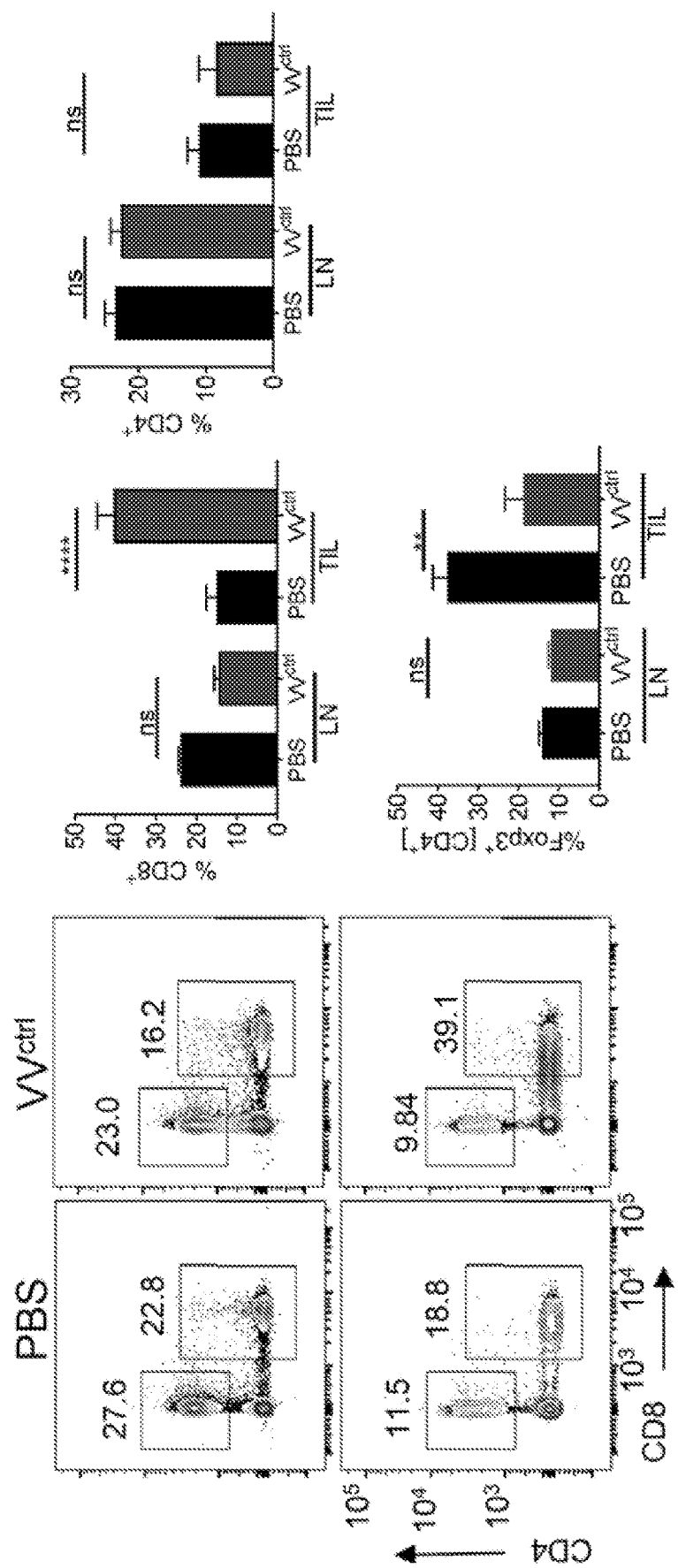

Oncolytic Vaccinia Virus Promotes Non-Exhausted T Cell Infiltration with Severe Metabolic Deficiencies Flow cytometric analysis of the TIL from oncolytic virus treated mice confirmed that the influx of new immune cells appeared to be dominated by $CD8^+$ T cells while we observe a decrease of T regulatory T cells (FIG. 4A). Analysis of the co-inhibitory marker expression of these cells show an influx of $CD8^+$ T cells that have expression of Tim3 alone (FIG. 4B) as well as a low to mid expression of PD1 (FIG. 4C) indicating these cells are not reinvigorated tumor residents but rather new immigrants and are not yet fully exhausted T cells. While co-inhibitory molecule expression is associated with T cell dysfunction, metabolic insufficiency, too, can predict T cell function. Mitochondrial content was analyzed as a marker for metabolic sufficiency, revealing that despite the 'non-exhausted' co-inhibitory molecule pattern of expression, TIL from oncolytic virus-treated tumors still succumbed to metabolic exhaustion (FIG. 4D).

Example 4

Leptin Metabolically Reprograms Activated T Cells

Given that oncolytic viruses stimulated new immune infiltrate that still succumbed to metabolic insufficiency, ways to bolster those new T cells such that they would be more competitive in the tumor microenvironment were identified. The goal was to utilize a genetically encoded payload, so that such an agent could be encoded in the viral vector. Leptin is a cytokine that modulates energy homeostasis as well as promotes an inflammatory response. To determine the metabolic reprogramming functions of leptin on T cells, activated $CD8^+$ T cells isolated from peripheral lymph nodes (LN) were cultured in increasing concentrations of leptin.

Figure 5C:
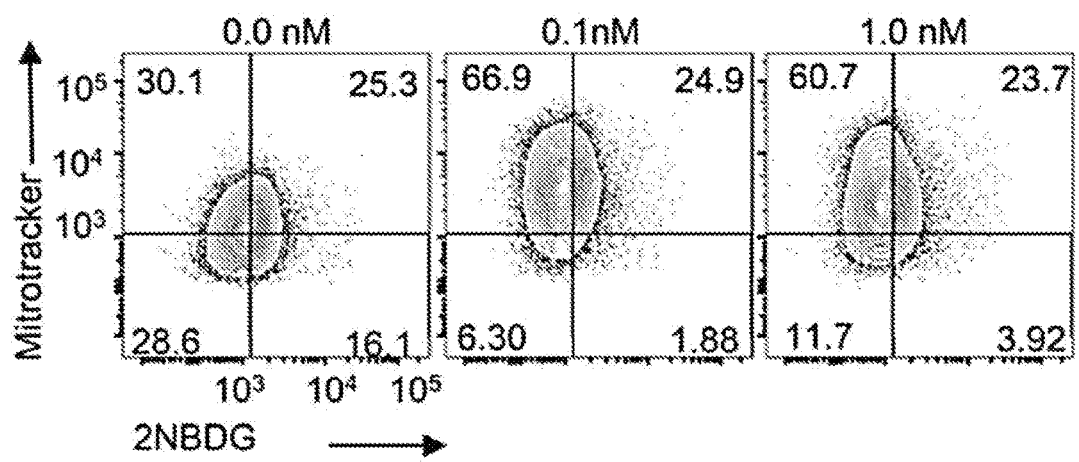
Figure 5C:
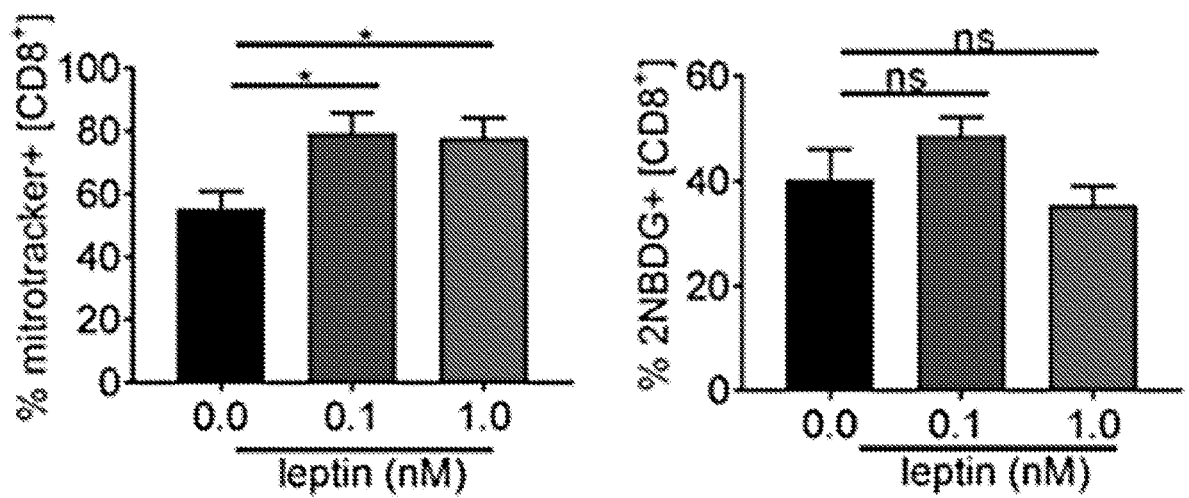

Leptin induced increases in both basal oxygen consumption rate as well as spare respiratory capacity (a measure of mitochondrial reserve that defines long-lived memory T cells (20)) of $CD8^+$ T cells (FIG. 5A), but had little effect on activated T cells' ability to perform glycolysis as measured by extracellular acidification (FIG. 5B). Flow cytometry analysis reinforces this data showing an increase in mitochondrial mass under leptin exposure indicative of higher oxidative phosphorylation, while observing no changes in glucose uptake (FIG. 5C). Thus, leptin can stimulate T cells to increase their oxidative activity and capacity, a metabolic reprogramming event highly desirable in the tumor microenvironment.

Figure 5D:
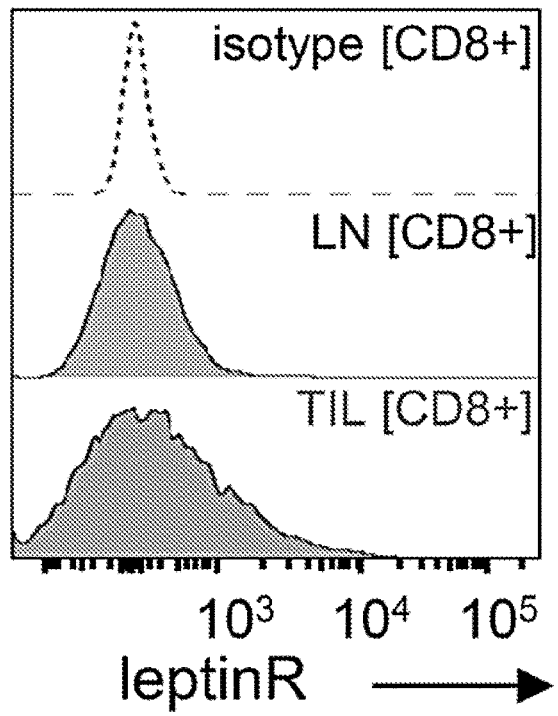
Figure 5D:
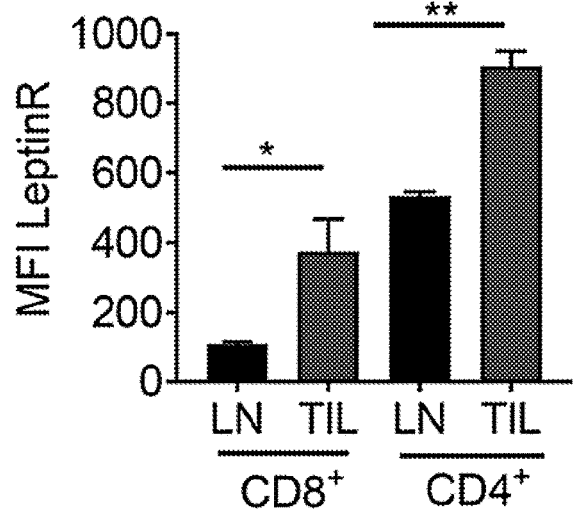

The expression of the leptin receptor in was confirmed in murine T cells, as previously observed (18) (FIG. 5D).

Figure 5E:
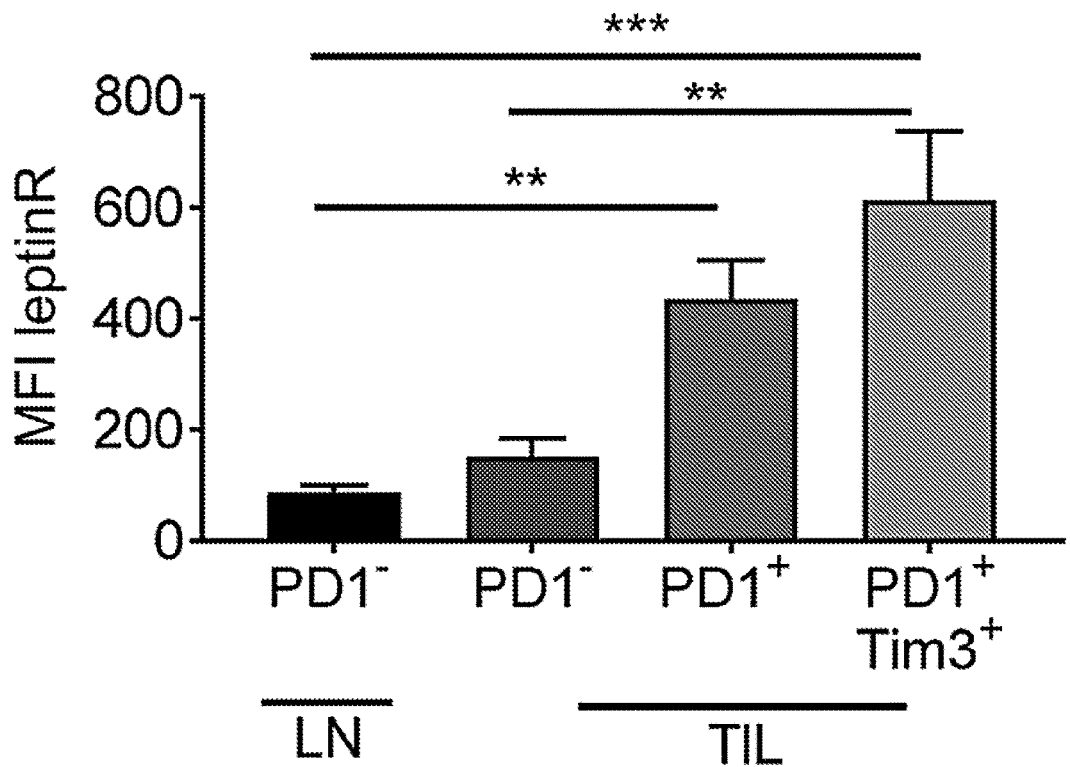

Furthermore, melanoma tumor infiltrating lymphocytes (TIL) express a higher level of the leptin receptor compared to T cells in the lymph nodes (FIG. 5D). Categorizing the TIL according to their expression levels of co-inhibitory molecules, higher expression of the leptin receptor was observed in activated or exhausted T cells with high expression of PD1 and Tim3 (FIG. 5E). Thus, leptin can promote metabolic reprogramming in T cells, and tumor-infiltrating T cells bear its receptor.

Example 5

Elevating Local Leptin Levels in the Tumor Microenvironment Enables Antitumor Immunity The therapeutic effects of leptin in the context of tumor infiltrating lymphocytes have not been previously investigated. It was hypothesized that leptin can enhance the metabolic capacity of tumor infiltrating lymphocytes, consequently enhancing their function in the tumor.

Figure 6A:
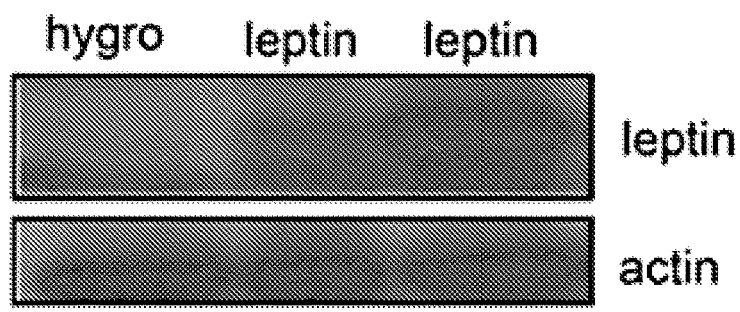
Figure 6B:
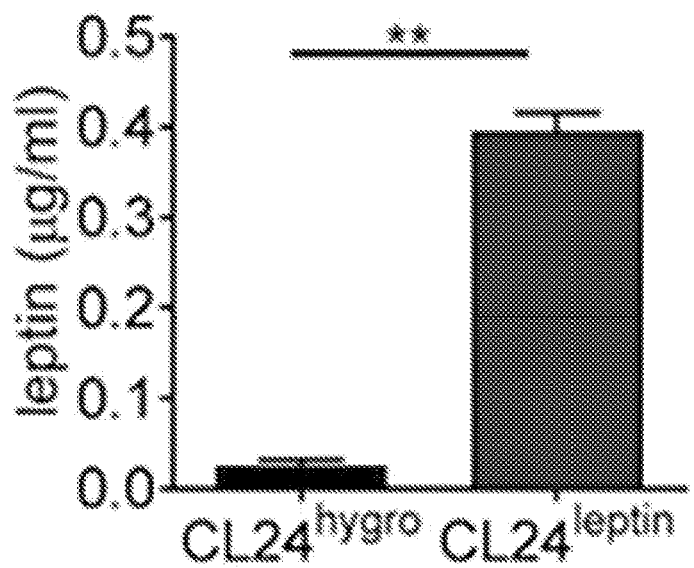
Figure 6C:
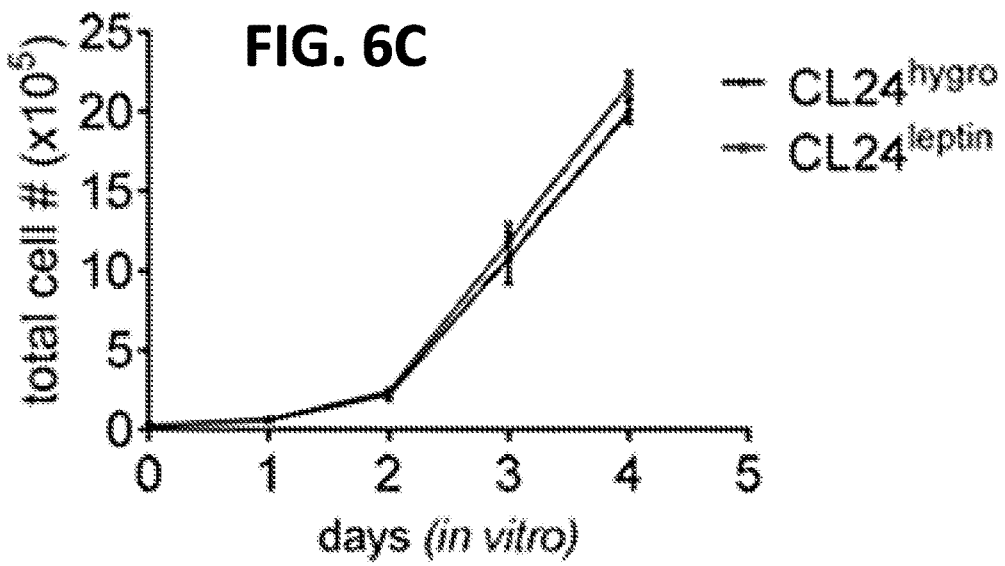
Figure 6E:
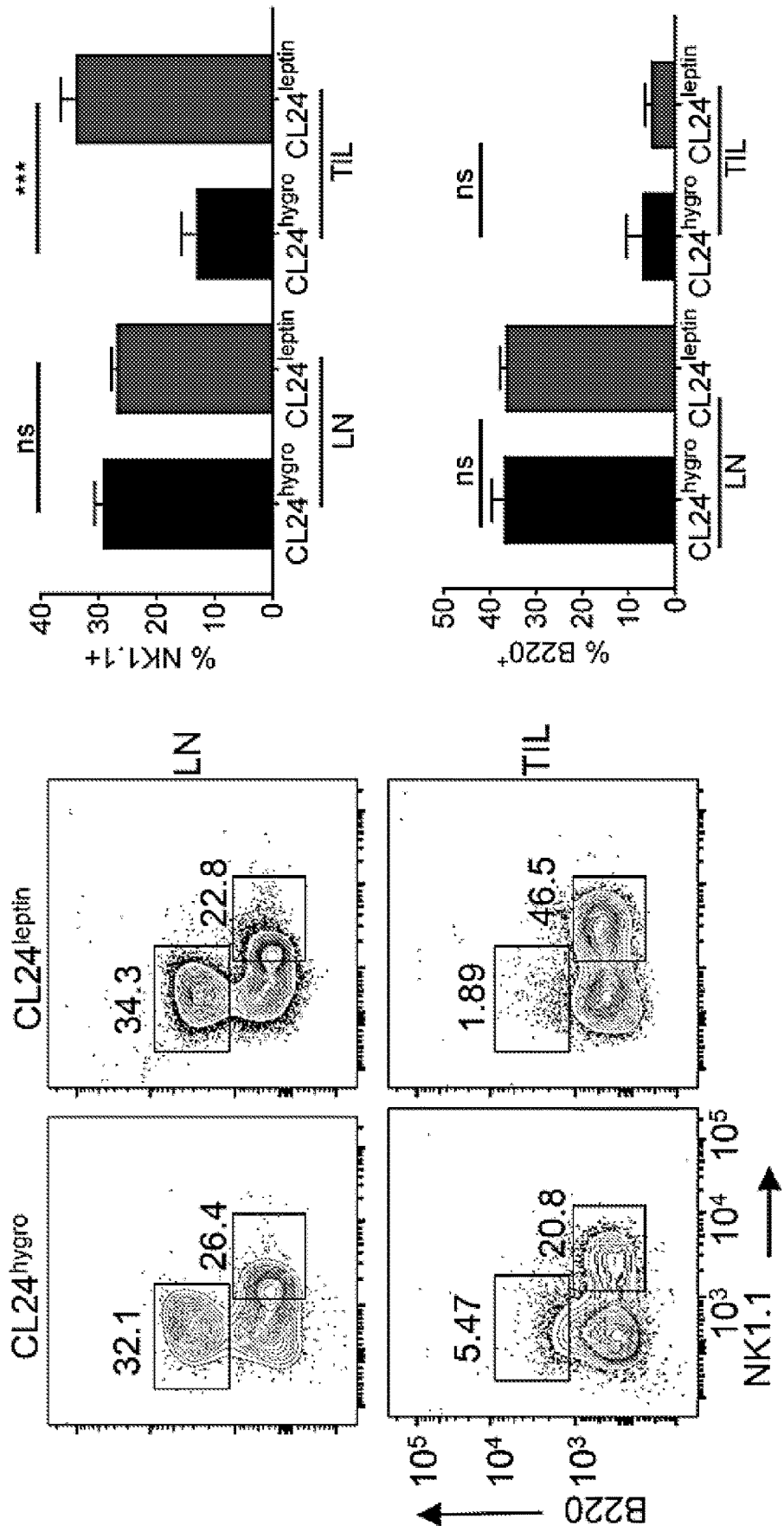
Figure 7A:
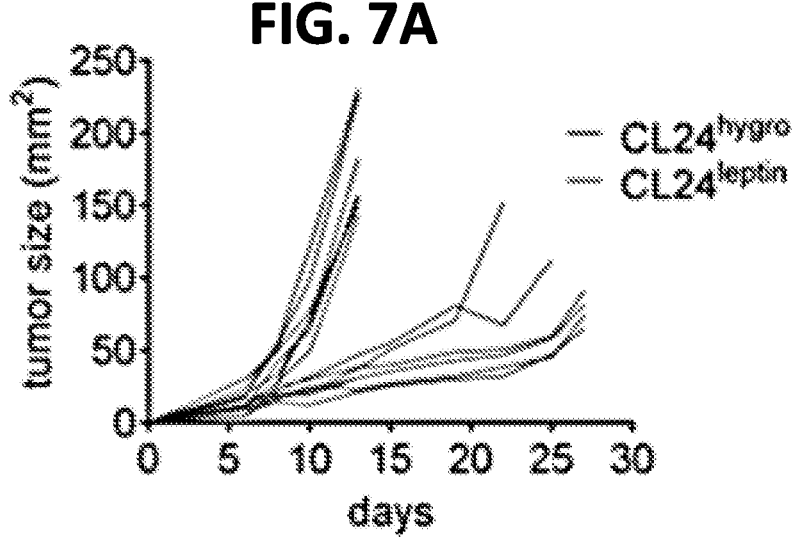
FIGS. 7A-7G. Expression of leptin in cancer cells results in immune-mediated tumor control and metabolically improves the function of tumor infiltrating lymphocytes. (A) CL24hygro and CL24leptin were injected subdermally on C57BL/6J mice and tumor growth monitored. Each line represents an individual mouse. (B) Survival plot of mice treated as in (A). (C) C57BL/6J mice were treated every other day with anti-CD8 (200 ug). At day 6 mice were injected with either CL24hygro or CL24leptin and tumor growth was monitored. (D) CD8 and CD4 expression analysis on LN and TIL from mice injected with CL24hygro and CL24leptin. Representative flow cytogram of CD8 and CD4 staining in LN and TIL and tabulated flow cytometric data. (E) Representative flow cytogram of LN and TIL from mice injected with CL24hygro and CL24leptin cells were stimulated overnight with PMA and ionomycin for cytokine production analysis by staining for IFNγ and TNFα of CD8+ T cells. Tabulated flow cytometric data are shown. (F) Representative flow cytogram and tabulated flow cytometric data for CD8+ T cells from LN and TIL from mice injected with CL24hygro and CL24leptin analyzed for Ki67 expression and metabolic markers Mitotracker FM staining and 2NBDG uptake (G). Data represents at least 3 independent experiments $*p<0.05$, $p<0.01$, $*p<0.001$ by paired t-test. Error bars indicate s.e.m.
Figure 7B:
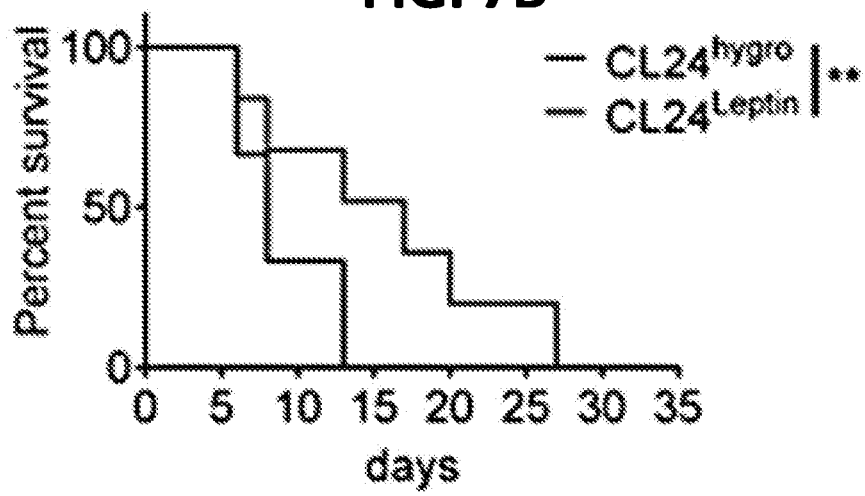
Figure 7C:
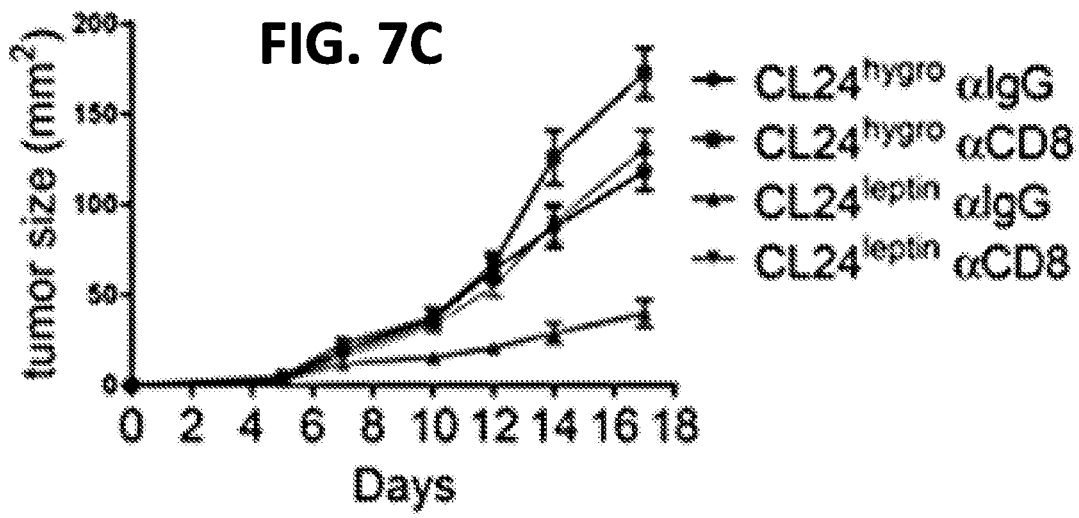
Figure 7D:
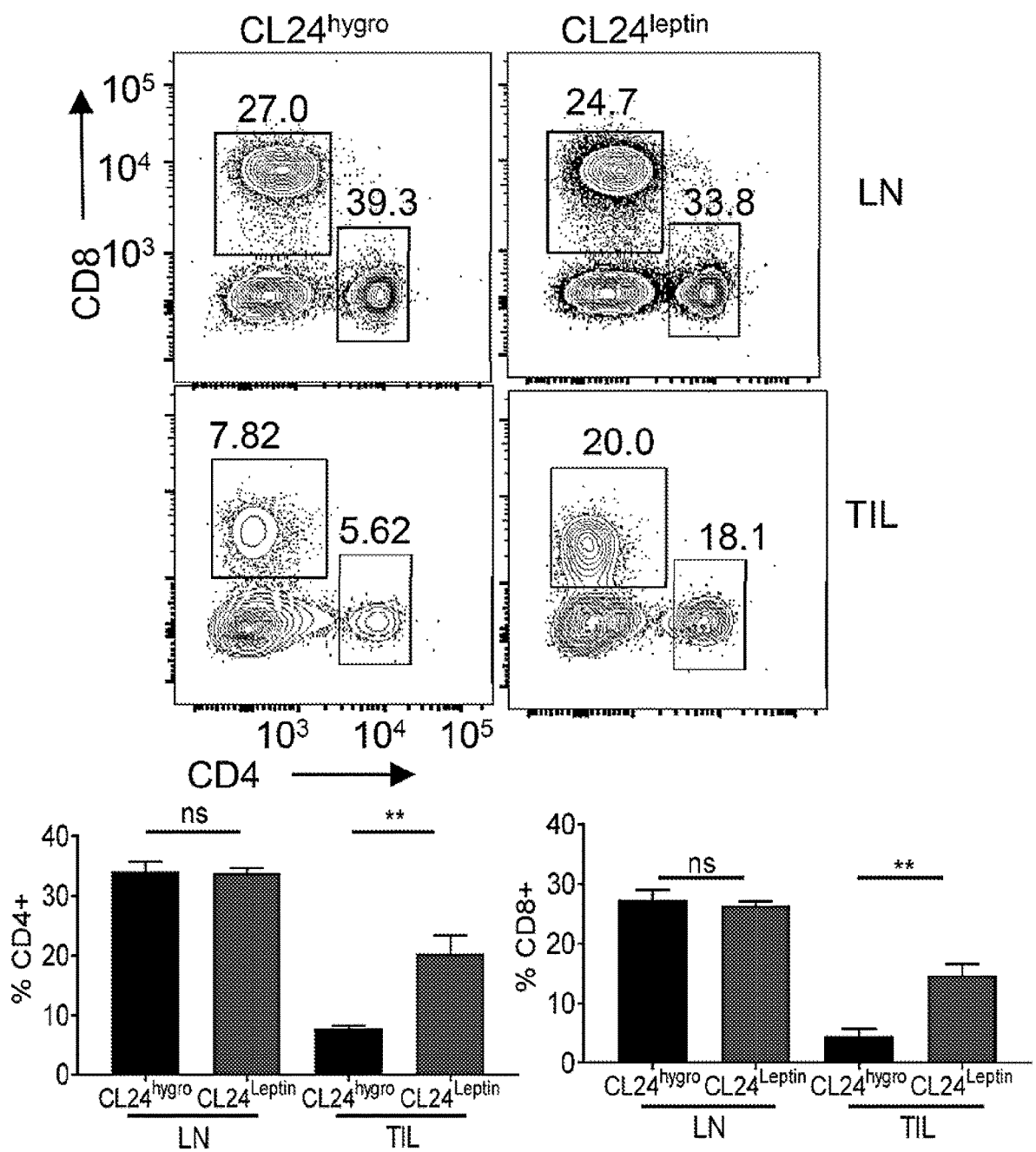

Initial studies treating tumor-bearing mice with recombinant leptin showed that systemic delivery, even at relatively high doses, cannot substantially improve leptin levels in the tumor interstitial fluid. So to first test the metabolic reprogramming functions of leptin in isolation (outside of oncolytic virus infection), CL24 were engineered cells to express an empty vector ($CL24^{hygro}$) or leptin ($CL24^{leptin}$). $CL24^{leptin}$ cells expressed leptin intracellularly (FIG. 6A) and released it into culture supernatant (FIG. 6B). In vitro, $CL24^{leptin}$ showed a comparable growth kinetics with CL24- expressing a control plasmid ($CL24^{hygro}$) (FIG. 6C). However, when $CL24^{leptin}$ cells were injected subdermally into C57BL/6J mice, they grew at a substantially slower rate compared to $CL24^{hygro}$ controls (FIG. 7A) and have significantly prolonged survival (FIG. 7B) indicating leptin may stimulate host immunity. Indeed, depletion of $CD8^+$ T cells (FIG. 6D) revealed that the controlled tumor growth observed in $CL24^{leptin}$ tumors required functional immunity (FIG. 7C). Thus, locally elevating leptin in the tumor microenvironment induced immune-mediated tumor growth control. Analysis of the tumor infiltrating lymphocytes at day ten (when tumors were of comparable size between groups) showed an increased infiltration of $CD8^+$ T cells in the tumors expressing leptin compared to control tumors (FIG. 7D). Increased infiltration of natural killer cells, but not other immune populations such as B cells, was observed (FIG. 6E).

Example 6

Leptin Metabolically Improves the Function of Tumor Infiltrating Lymphocytes

Figure 7E:
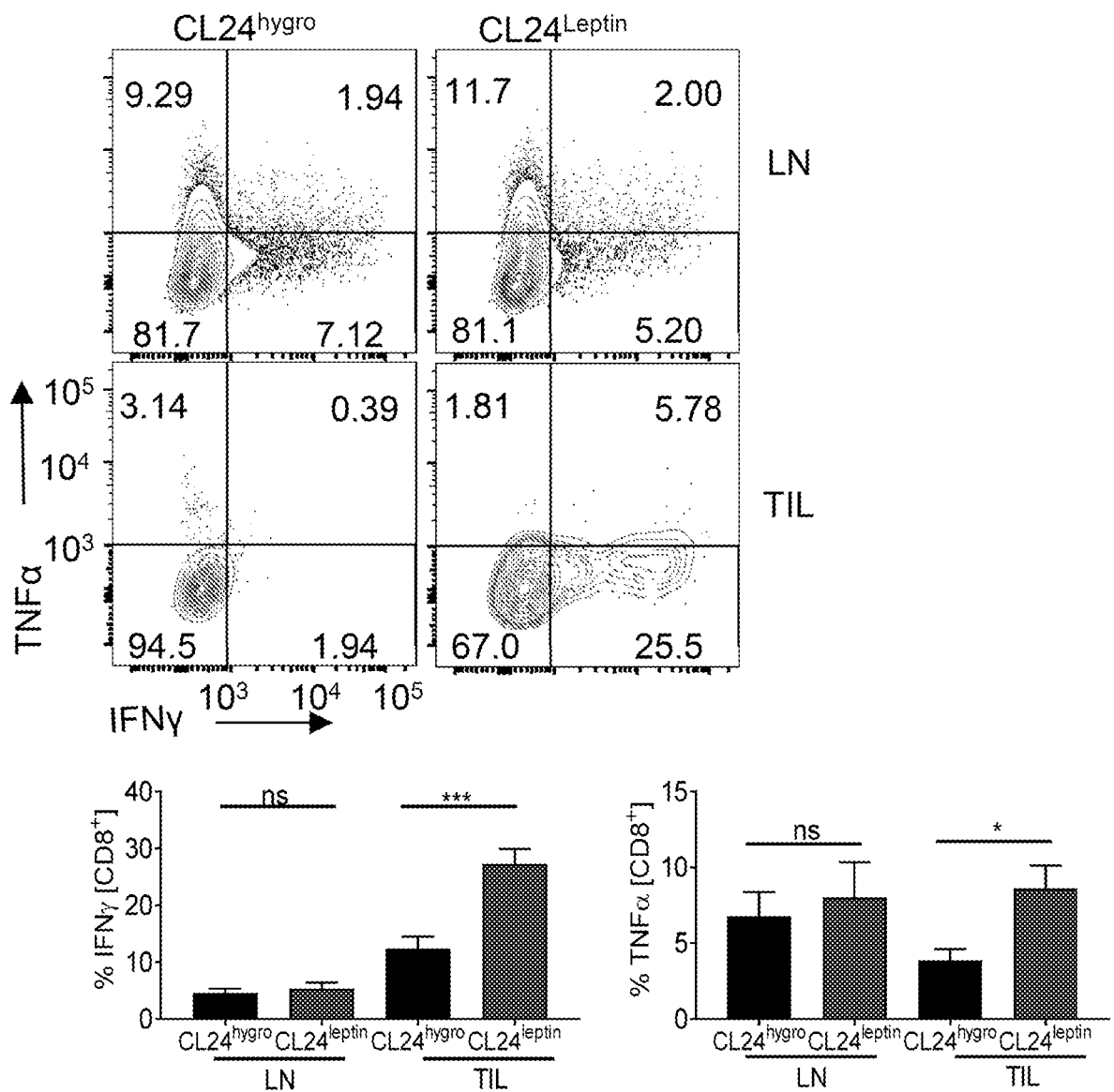
Figure 7F:
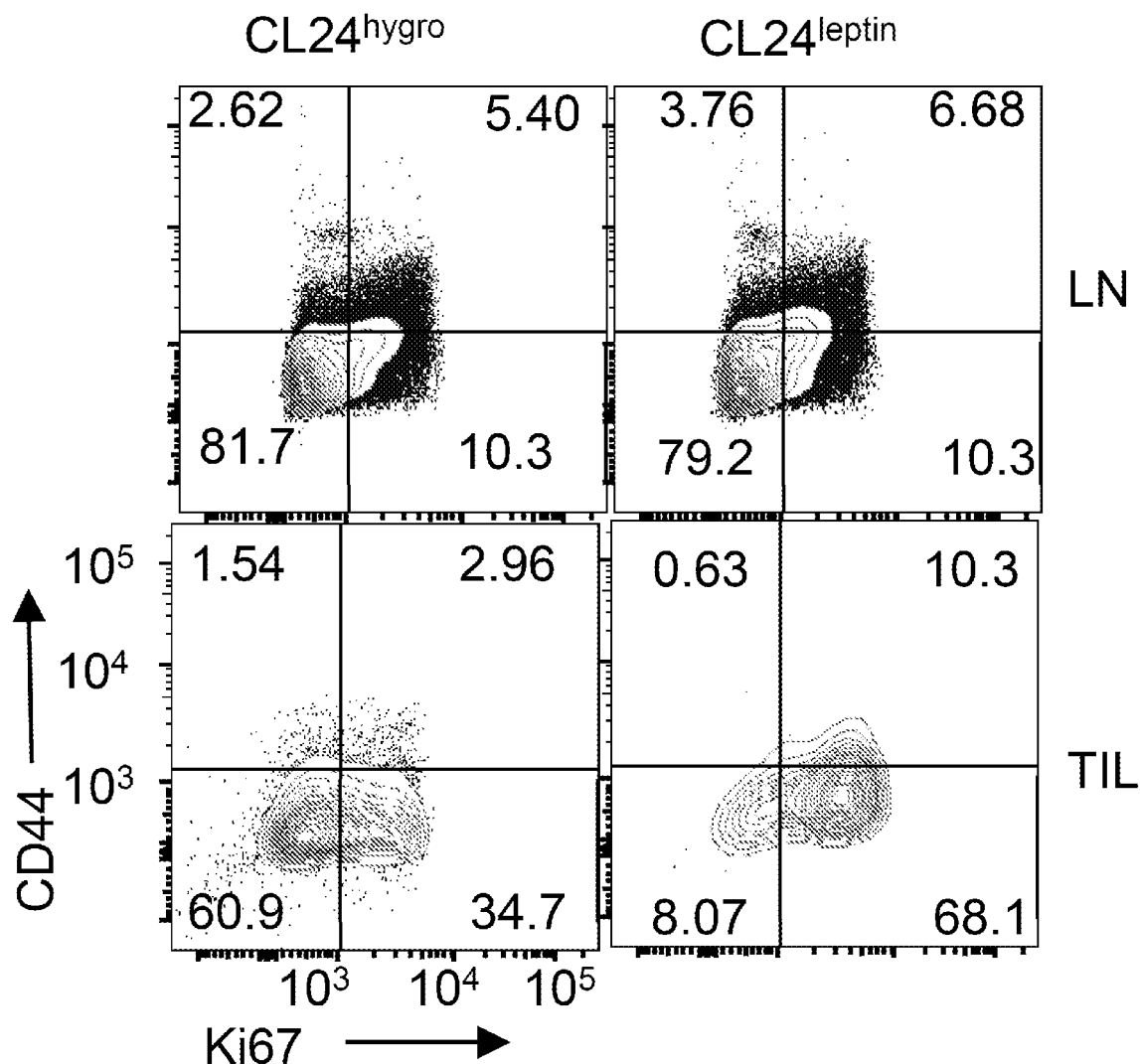
Figure 7F:
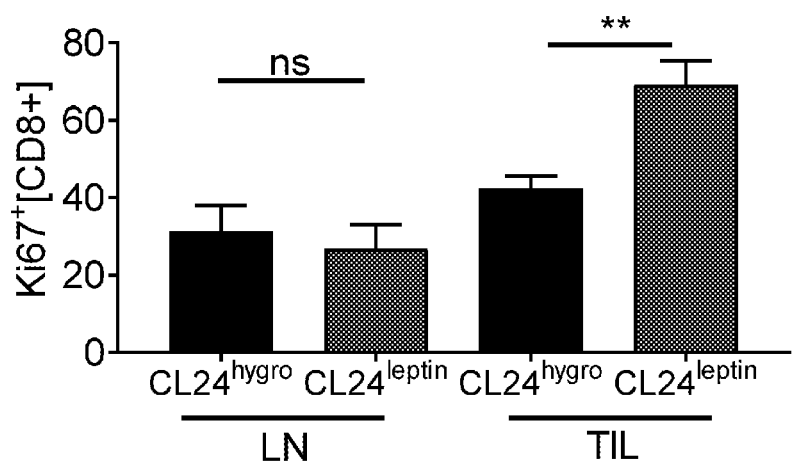
Figure 7G:
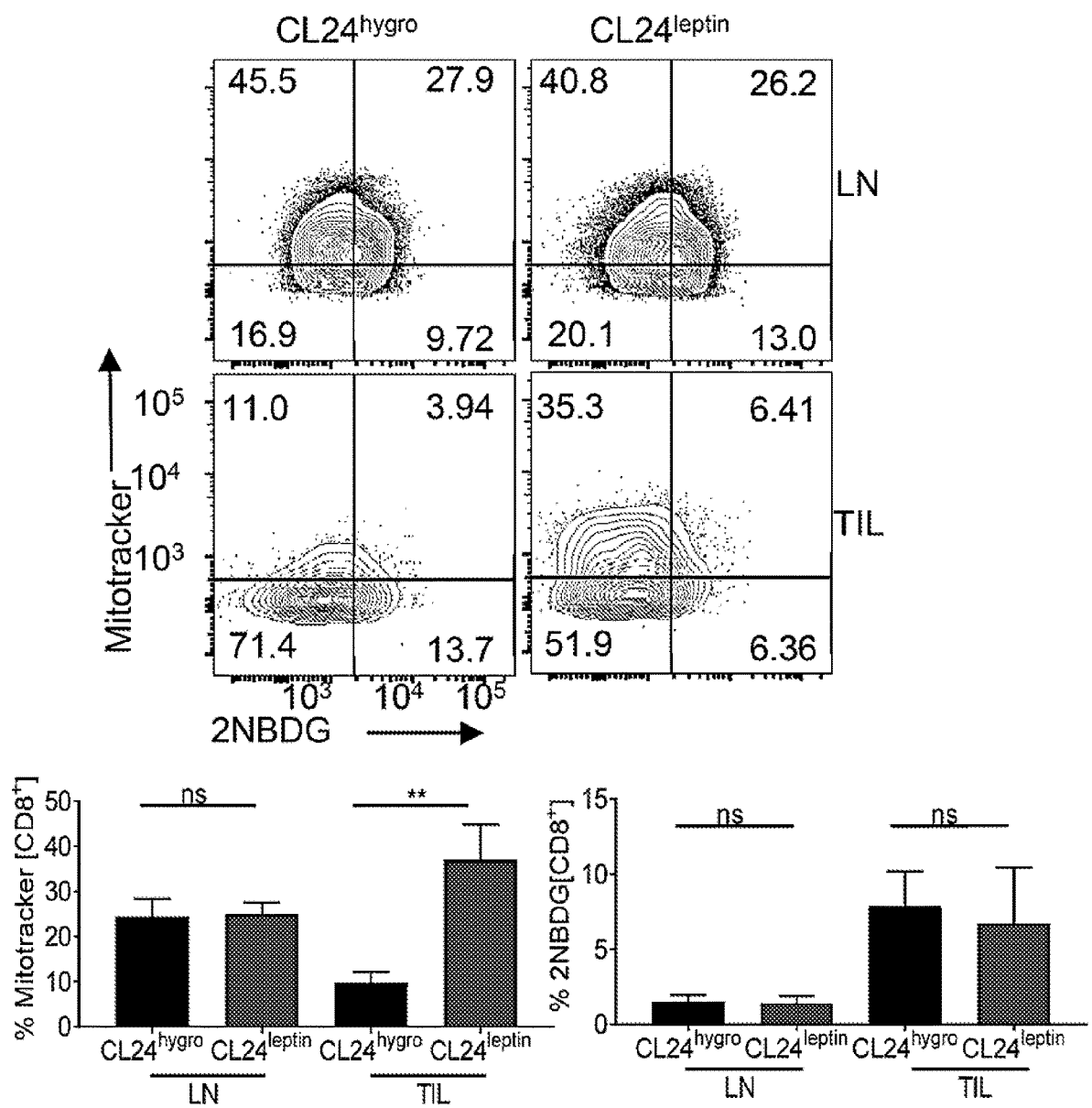

It was observed that leptin functionally improved T cells. $CD8^+$ T cells infiltrating leptin-overexpressing tumors synthesized elevated levels of IFNγ and TNFα upon restimulation with PMA and ionomycin (FIG. 7E). Additionally, $CD8^+$ T cells that infiltrate leptin expressing tumors are more proliferative in situ as measured by Ki67 staining (FIG. 7F). Leptin can activate downstream signals via the leptin receptors through the JAK-Stat3 and MAPK pathway, and indeed, T cells infiltrating leptin-overexpressing tumors had higher steady-state phosphorylation of AKT, STAT5 and p38-MAPK (FIG. 6F). Thus, while these cells may appear more phenotypically 'exhausted', leptin-induced metabolic support allowed cells to be polyfunctional, proliferative, and mediate tumor control.

Example 7

Leptin Expressing Oncolytic Vaccinia Virus Induces Superior Antitumor Responses

Figure 8A:
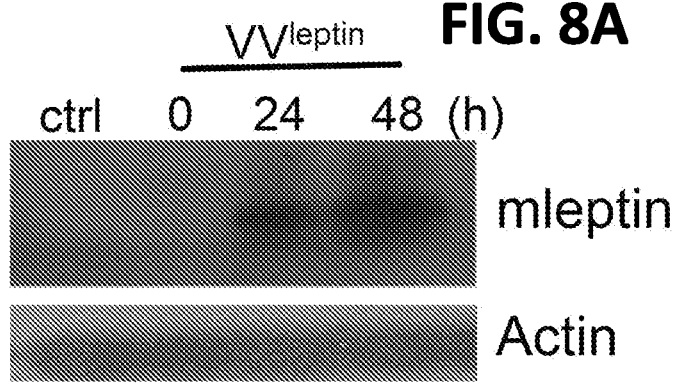
FIGS. 8A-8F. Leptin-engineered oncolytic Vaccinia virus induces leptin secretion in vitro and in vivo without affecting infectivity. (A) Immunoblot analysis of mouse leptin protein expression of CL24 cell line treated with VVleptin at 2.5×106 PFU in vitro 24 h and 48 h. (B) ELISA analysis of leptin in the media of CL24 cells treated with VVleptin. (C) ELISA analysis of leptin in interstitial fluid of tumors treated with VVcontrol or VVleptin. Interstitial fluid from white adipose tissue (WA) used as control. Data represents at least 3 independent experiments $*p<0.05$ by two-way ANOVA. Error bars indicate s.e.m. (D) C57BL/6J mice were injected subdermally with CL24 cells. 5-7 days after tumor cell injection tumors were treated intratumorally with PBS, VVcontrol, or VVleptin 24 h later mice were injected with luciferin (30 mg/ml) IP for 10 min and conducted In Vivo Bioluminescence Imaging (E) C57BL/6J mice were injected subdermally with CL24 cells. 5-7 days after tumor cell injection tumors were treated intratumorally with PBS, VVcontrol, or VVleptin. On day 10 after treatment lymphocytes were isolated from TIL. Representative flow cytogram and tabulated flow cytometric data for leptin receptor (leptinR) expression. Error bars indicate s.e.m. (F) Representative flow cytogram and tabulated flow cytometric data for CD4+ Foxp3+T cells (T regulatory cells) from LN and TIL from mice injected with PBS, VVcontrol, or VVleptin. Data represents at least 3 independent experiments $*p<0.05$, $p<0.01$, $*p<0.001$ by two-way ANOVA. Error bars indicate s.e.m.
Figure 8B:
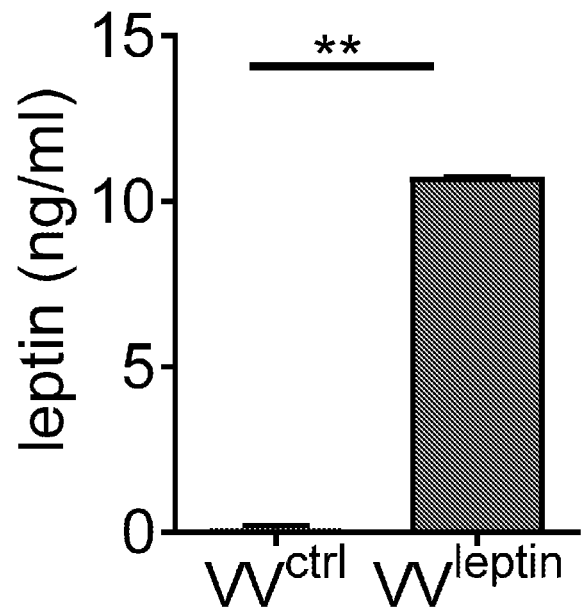
Figure 8C:
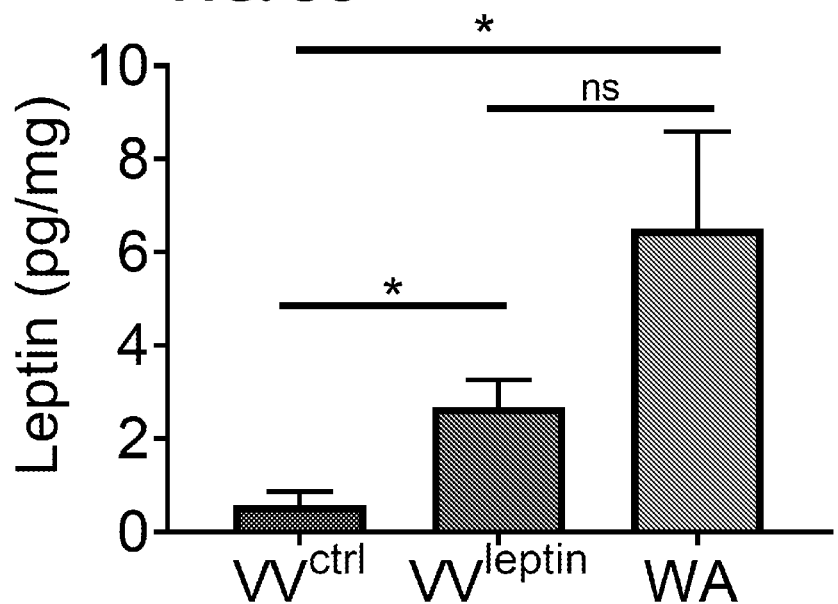
Figure 8D:
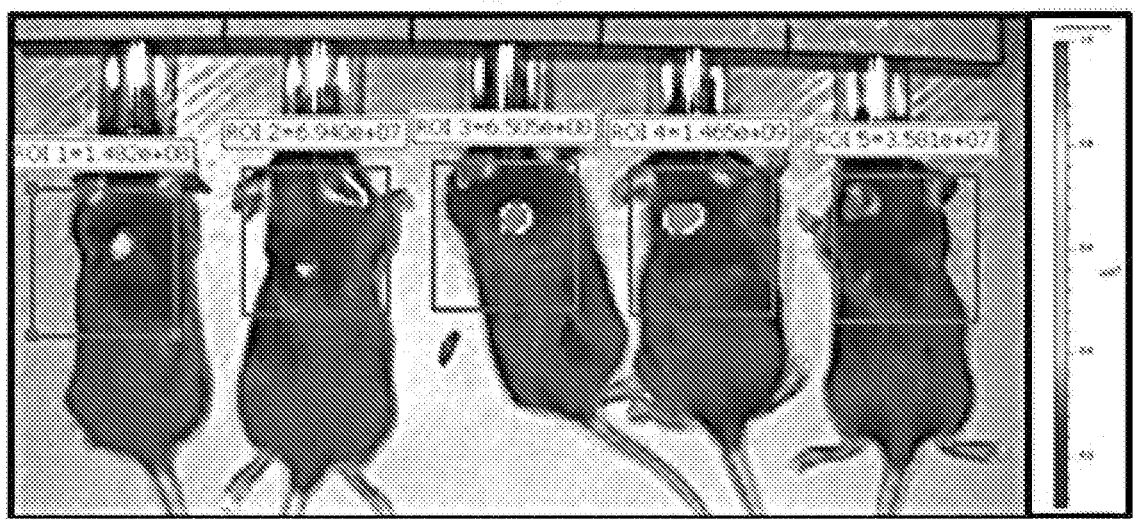
Figure 8D:
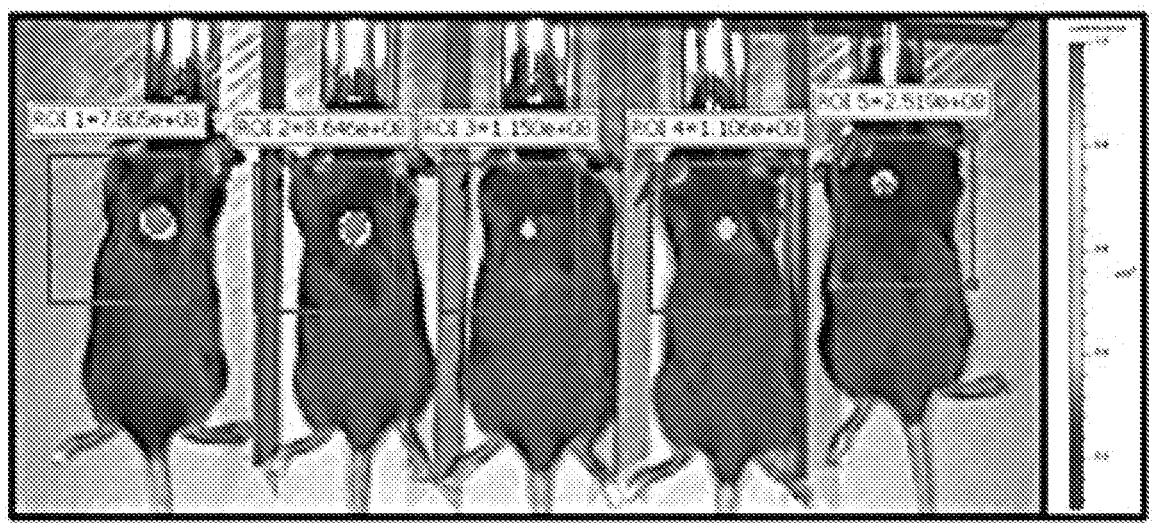
Figure 8E:
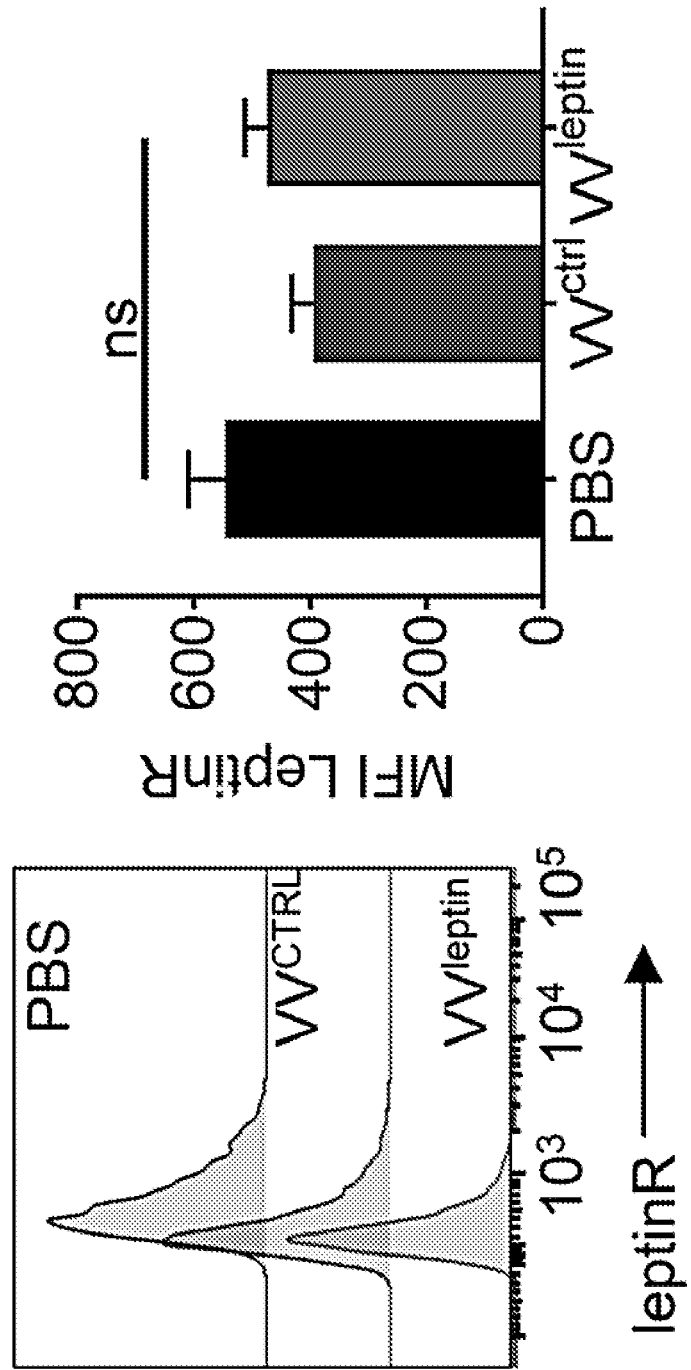

To generate a leptin expressing Vaccinia virus, the leptin gene (Lep) was cloned in the luciferase expressing pSC65 vector under the control of the Vaccinia p7.5 promoter. Leptin containing recombinant vaccinia virus ($VV^{leptin}$) and control luciferase expressing virus ($VV^{ctrl}$) were generated and used to infect CL24 cells. Expression of leptin in CL24 cells was analyzed 24 and 48 hour post infection (FIG. 8A) as well as the release of leptin in the media (FIG. 8B). Mice harboring CL24 tumors were treated with $VV^{ctrl}$ or $VV^{leptin}$ with a dose of $2.5 \times 10^6$ PFU intratumorally, which was sufficient to induce luciferase expression specifically in the tumor (FIG. 8D) and detect free leptin in the tumor interstitial fluid; white adipose (WA) tissue interstitial fluid acted as a positive control (FIG. 8C). Furthermore, analysis of leptin receptor (LeptinR) expression in TIL show no changes between the three treatment conditions (FIG. 8E).

Figure 9A:
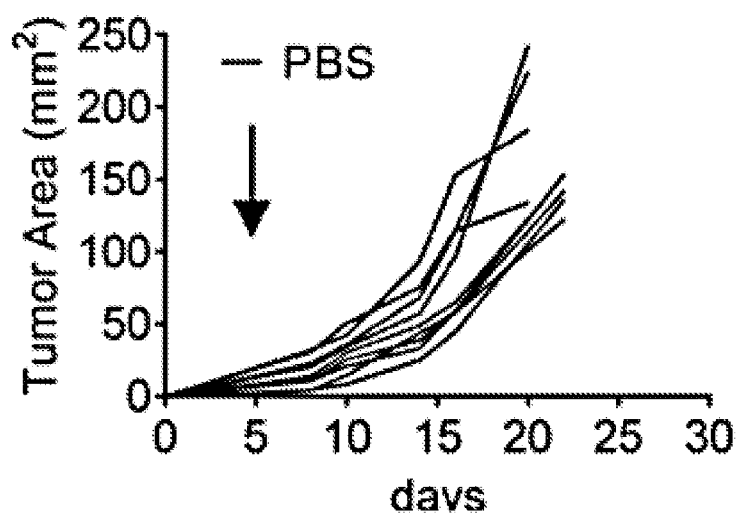
Figure 9A:
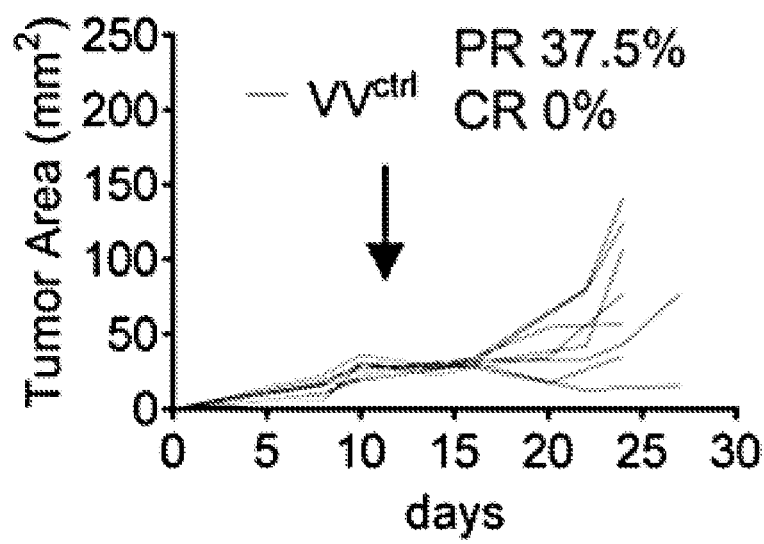
Figure 9A:
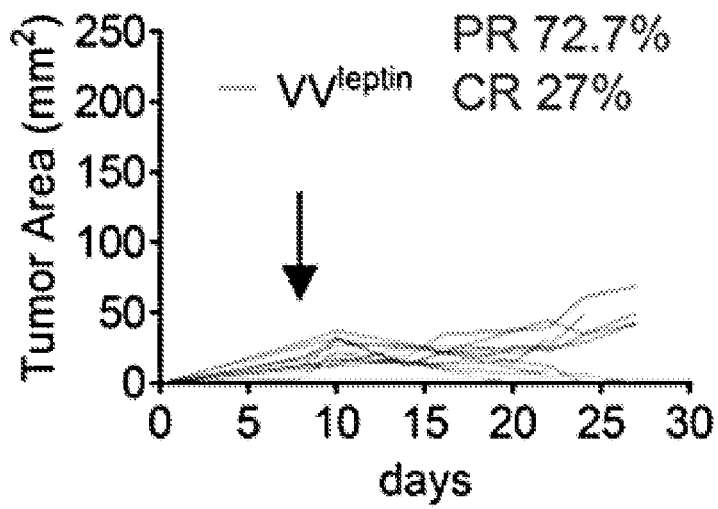

Consistent with previous results, all mice injected with control virus experienced partial responses, leading to eventual tumor outgrowth. The partial response to control virus was especially exciting as this aggressive melanoma line is completely resistant to anti-PD1 immunotherapy (FIG. 1C). In contrast to mice treated with $VV^{ctrl}$, those injected with the same dose of $VV^{leptin}$ had larger regressions, including a substantial proportion of complete responses (FIG. 9A).

Figure 9C:
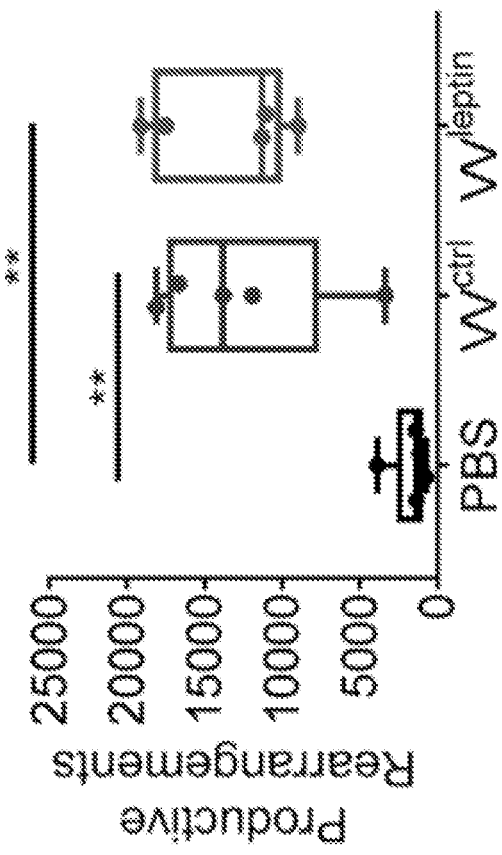
Figure 9D:
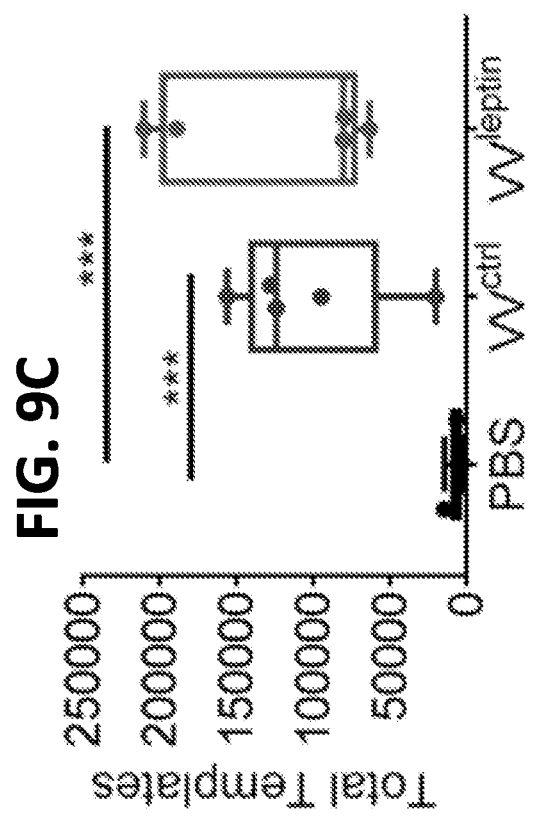
Figure 9D:
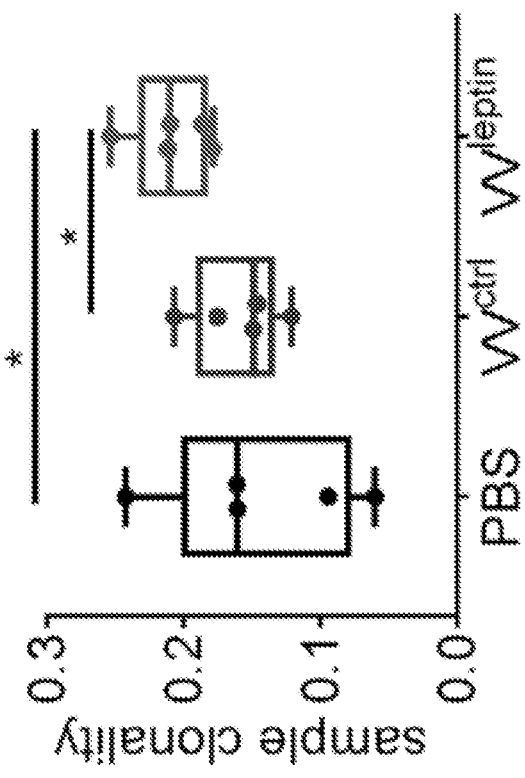
Figure 9E:
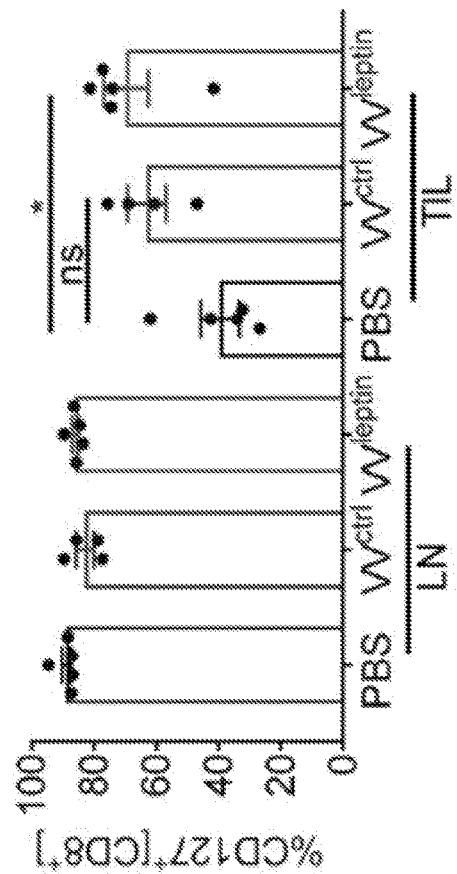
Figure 9E:
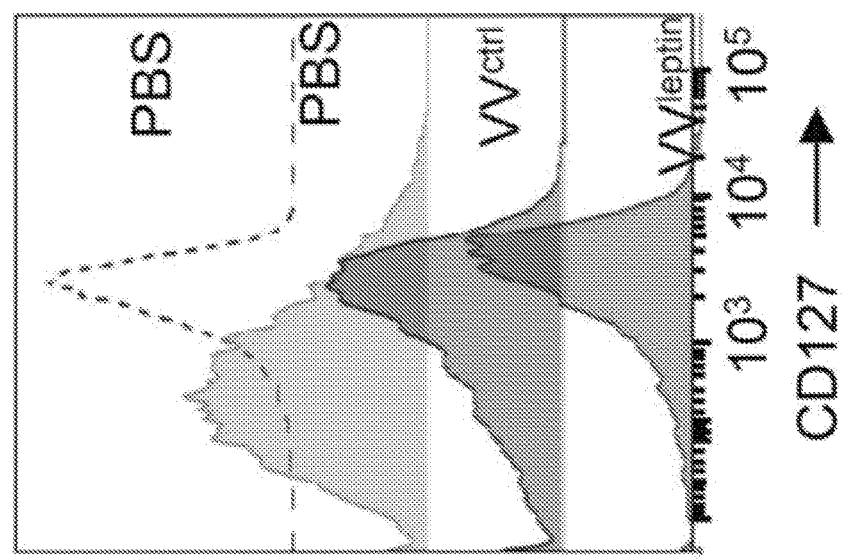

The transcriptomic profiles were confirmed with analysis of the tumor infiltrate. Consistent with the scRNAseq data, analysis of immune infiltrate in tumors treated with $VV^{ctrl}$ and $VV^{leptin}$ showed that both oncolytic viruses induced an increase in T cell infiltration at the tumor site (FIG. 9B). As oncolytic viruses have been purported to induce new T cell priming to viral and tumor antigens (Brown et al., *Sci Transl Med* 2017; 9(408); Russell et al., *Cancer Cell* 2018; 33(4): 599-605), the effects of the treatments on the T cell repertoire at the tumor site was examined TCR sequencing revealed that while PBS treated tumors had few infiltrating T cells dominated by an oligoclonal population, treatment with Vaccinia resulted in a substantial influx of new T cells with a polyclonal repertoire (FIG. 9C). Leptin-engineered Vaccinia had a slightly less clonal population, suggesting at this time point (7 days after viral treatment) some clones were preferentially expanding (FIG. 9D). The clonal expansion could be indicative of expansion of some memory precursors, and indeed leptin-engineered VV induced a greater percentage of $CD127^{hi}$ memory precursors (FIG. 9E).

Figure 8F:
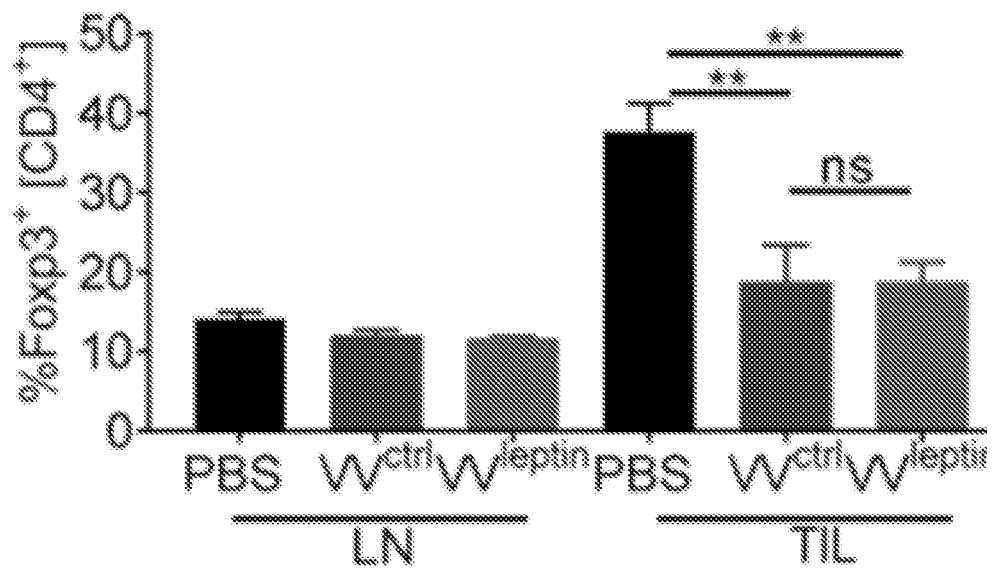
Figure 8F:
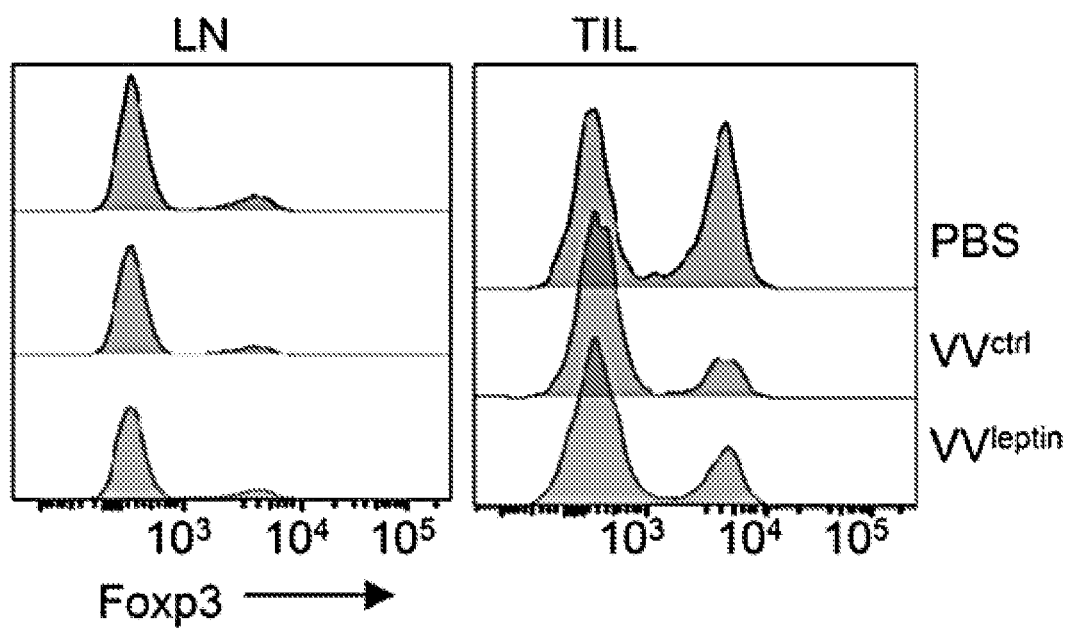

Leptin inhibits regulatory T cells ($T_{reg}$) and modulates the inflammatory response in autoimmune diseases. Furthermore, oncolytic virus therapy can reduce the infiltration of $T_{reg}$ cells (Barve et al., *J Clin Oncol* 2008; 26(27):4418-25; Ricca J et al., *Mol Ther* 2018; 26(4):1008-19). Consistently, after oncolytic virus treatment of $VV^{ctrl}$ and $VV^{leptin}$ a decrease in percentage of the $T_{reg}$ population compared to PBS treatment was observed with comparable levels between $VV^{ctrl}$ and $VV^{leptin}$ (FIG. 8F) indicating that leptin was not necessarily acting at the level of $T_{reg}$ cell modulation.

Figure 10A:
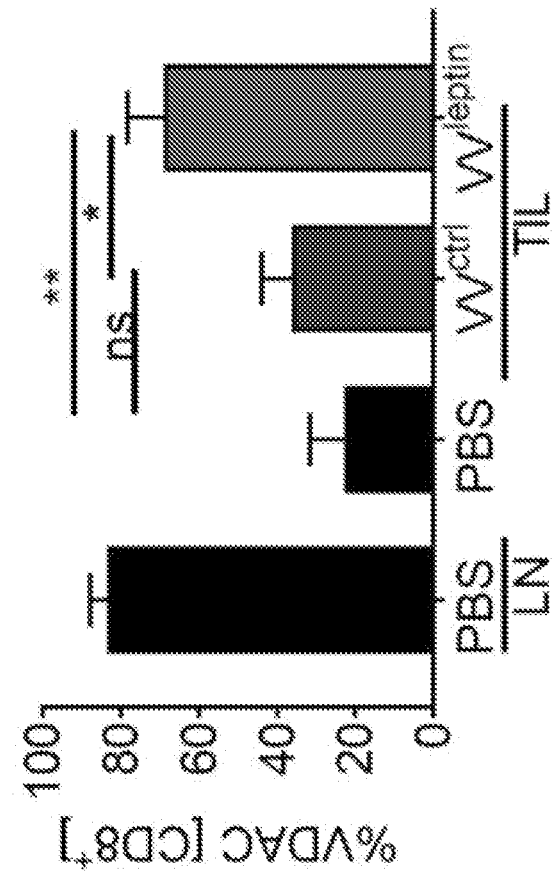
Figure 10A:
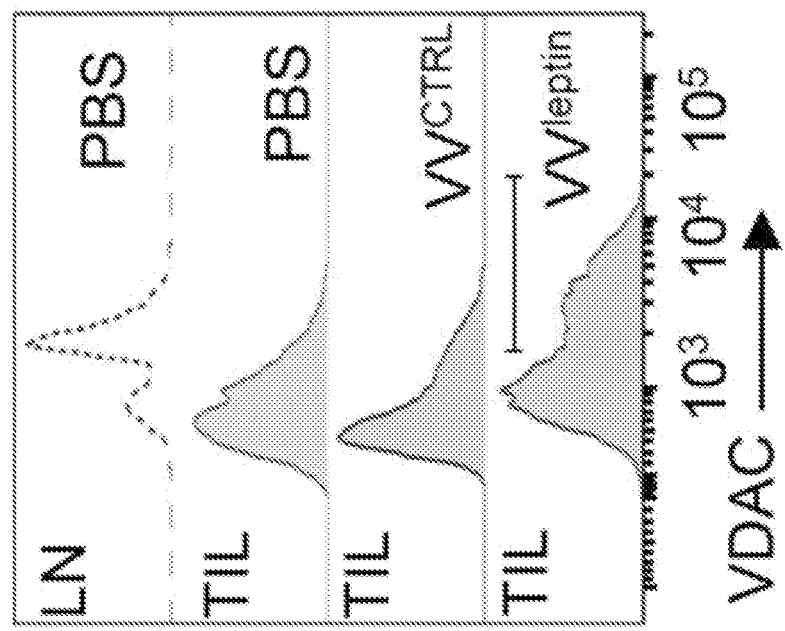

Memory T cells have increased mitochondrial reserve and depend on that reserve for their memory function (van der Windt et al., *PNAS* 2013; 110(35):14336-41). As such, leptin may metabolically support $CD8^+$ T cells. $CD8^+$ T cells in tumors treated with $VV^{leptin}$ exhibited an increase in mitochondrial mass as measured by VDAC staining (FIG. 10A).

Figure 10B:
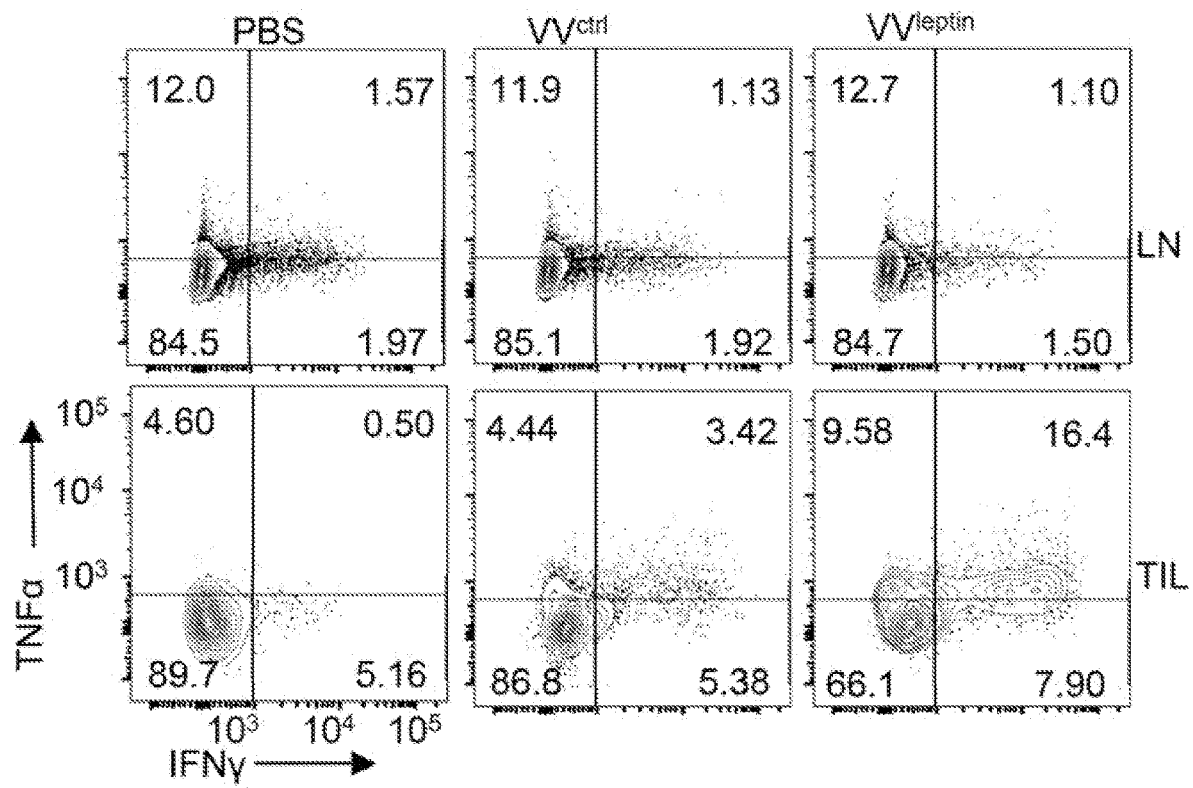
Figure 10B:
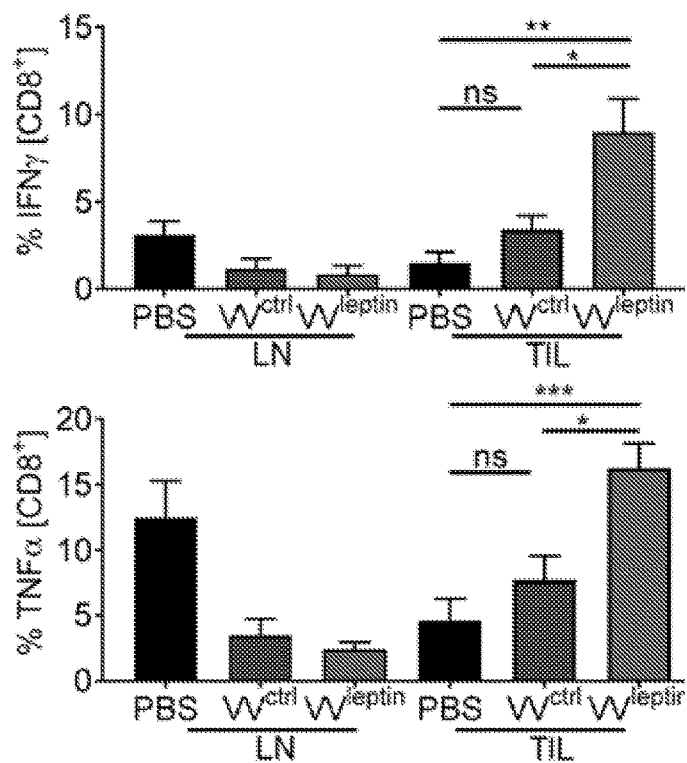

Furthermore, analysis of CD8+ T cells infiltrating treated tumors revealed VV$^{leptin}$ induced a qualitatively superior tumor infiltrate: increased T cell activity at the tumor site shown by an increase in cytokine competency (FIG. 10B), as well as increased proliferative capacity (FIG. 10C).

In summary, these data demonstrate that by providing metabolic support to newly infiltrated T cells induced by oncolytic virus treatment, memory precursor populations with superior anti-tumor capabilities can preferentially expand and mediate complete responses.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A recombinant oncolytic virus, comprising:
   a nucleic acid molecule encoding one or more metabolic modulating proteins, wherein the one or more metabolic modulating proteins is leptin, adiponectin, apelin, or chemerin.

2. The recombinant oncolytic virus of claim 1, wherein the nucleic acid is operably linked to a promoter.

3. The recombinant oncolytic virus of claim 1, wherein the oncolytic virus is a herpes simplex virus (HSV), adenovirus, poxvirus, reovirus, poliovirus, coxsackie virus, measles virus, vesicular stomatitis virus (VSV), Seneca valley virus, ECHO virus, Newcastle disease virus, chicken anemia virus, or parovirus.

4. The recombinant oncolytic virus of claim 3, wherein:
   the HSV is talimogene laherparepvec (T-VEC) or HSV-1; or
   the poxvirus is vaccinia virus.

5. The recombinant oncolytic virus of claim 4, wherein the vaccinia virus is Western Reserve strain Vaccinia virus.

6. The recombinant oncolytic virus of claim 1, wherein the one or more metabolic modulating proteins is leptin.

7. The recombinant oncolytic virus of claim 1, wherein the one or more metabolic modulating proteins comprises a fusion protein, wherein the fusion protein comprises a first protein and a second protein, wherein the first protein comprises the one of the one or more metabolic modulating proteins.

8. The recombinant oncolytic virus of claim 7, wherein the second protein is a cytokine, chemokine, an interferon, an interleukin, a lymphokine, and/or a tumour necrosis factor.

9. The recombinant oncolytic virus of claim 8, wherein the cytokine is interleukin (IL)-1, IL-2, IL-17, IL-18, TGF-β1, TGF-β2, TGF-β3, IL-4, IL-10, IL-13, IL-7, IL-9, IL-15, IL-21, TNFα, IFN-γ, or any combinations thereof.

10. The recombinant oncolytic virus of claim 7, wherein the fusion protein comprises a linker between the first protein and the second protein.

11. The recombinant oncolytic virus of claim 1, wherein the one or more metabolic modulating proteins comprises at least about 80%, at least about 90%, or at least about 95% sequence identity to SEQ ID NO: 2 or 6.

12. The recombinant oncolytic virus of claim 1, wherein the nucleic acid molecule encoding the one or more metabolic modulating proteins comprises at least about 80%, at least about 90%, or at least about 95% sequence identity to SEQ ID NO: 1 or 5.

13. The recombinant oncolytic virus of claim 2, wherein the promoter is not native to the one or more metabolic modulating proteins.

14. A method of treating a tumor in a subject, comprising administering a therapeutically effective amount of the recombinant oncolytic virus of claim 1 to the subject, thereby treating the tumor.

15. A method of increasing T cell infiltration into a tumor, comprising
   administering a therapeutically effective amount of the recombinant oncolytic virus of claim 1 to a subject with the tumor, thereby increasing T cell infiltration into the tumor.

16. The method of claim 14, wherein the tumor is a cancer of the lung, breast, prostate, liver, pancreas, skin, colon, head and neck, kidney, cervix, or ovary.

17. The method of any of claim 14, further comprising administering a therapeutically effect amount of one or more additional therapies.

18. The method of claim 17, wherein the one or more additional therapies comprise:
   a PD-1 antagonist;
   a PD-L1 antagonist;
   a CTLA4 antagonist;
   a T cell agonist; or
   combinations thereof.

19. A composition or kit, comprising:
   (a) the recombinant oncolytic virus of claim 1; and
   (b) a PD-1 antagonist, a PD-L1 antagonist, a CTLA4 antagonist, a T cell agonist; or combinations thereof.

20. The composition or kit of claim 19, wherein the T cell agonist is an agonist of 4-1BB, an agonist of OX40, an agonist of glucocorticoid-induced tumor necrosis factor (TNF) receptor (GITR), or combinations thereof.

* * * * *

SEQUENCE LISTING

<160> NUMBER OF SEQ ID NOS: 8

<210> SEQ ID NO 1
<211> LENGTH: 3444
<212> TYPE: DNA
<213> ORGANISM: Homo sapiens

<400> SEQUENCE: 1

```
gtaggaatcg cagcgccagc ggttgcaagg cccaagaagc ccatcctggg aaggaaaatg      60
cattggggaa ccctgtgcgg attcttgtgg ctttggccct atcttttcta tgtccaagct     120
gtgcccatcc aaaaagtcca agatgacacc aaaaccctca tcaagacaat tgtcaccagg     180
atcaatgaca tttcacacac gcagtcagtc tcctccaaac agaaagtcac cggtttggac     240
ttcattcctg ggctccaccc catcctgacc ttatccaaga tggaccagac actggcagtc     300
taccaacaga tcctcaccag tatgccttcc agaaacgtga tccaaatatc caacgacctg     360
gagaacctcc gggatcttct tcacgtgctg gccttctcta agagctgcca cttgccctgg     420
gccagtggcc tggagacctt ggacagcctg ggggtgtcc tggaagcttc aggctactcc     480
acagaggtgg tggccctgag caggctgcag gggtctctgc aggacatgct gtggcagctg     540
gacctcagcc ctgggtgctg aggccttgaa ggtcactctt cctgcaagga ctacgttaag     600
ggaaggaact ctggcttcca ggtatctcca ggattgaaga gcattgcatg gacaccctt     660
atccaggact ctgtcaattt ccctgactcc tctaagccac tcttccaaag gcataagacc     720
ctaagcctcc ttttgcttga aaccaaagat atatacacag gatcctattc tcaccaggaa     780
gggggtccac ccagcaaaga gtgggctgca tctgggattc ccaccaaggt cttcagccat     840
caacaagagt tgtcttgtcc cctcttgacc catctccccc tcactgaatg cctcaatgtg     900
accaggggtg atttcagaga gggcagaggg gtaggcagag cctttggatg accagaacaa     960
ggttccctct gagaattcca aggagttcca tgaagaccac atccacacac gcaggaactc    1020
ccagcaacac aagctggaag cacatgttta tttattctgc attttattct ggatggattt    1080
gaagcaaagc accagcttct ccaggctctt tggggtcagc cagggccagg ggtctccctg    1140
gagtgcagtt ccaatcccca tagatgggtc tggctgagct gaacccattt tgagtgactc    1200
gagggttggg ttcatctgag caagagctgg caaaggtggc tctccagtta gttctctcgt    1260
aactggtttc atttctactg tgactgatgt tacatcacag tgtttgcaat ggtgttgccc    1320
tgagtggatc tccaaggacc aggttatttt aaaaagattt gttttgtcaa gtgtcatatg    1380
taggtgtctg cacccagggg tggggaatgt ttgggcagaa gggagaagga tctagaatgt    1440
gttttctgaa taacatttgt gtggtgggtt ctttggaagg agtgagatca ttttcttatc    1500
ttctgcaatt gcttaggatg ttttttcatga aaatagctct ttcaggggg ttgtgaggcc    1560
tggccaggca cccctggag agaagtttct ggccctggct gacccaaag agcctggaga    1620
agctgatgct ttgcttcaaa tccatccaga ataaaacgca aagggctgaa agccatttgt    1680
```

-continued

```
tggggcagtg gtaagctctg gctttctccg actgctaggg agtggtcttt cctatcatgg    1740
agtgacggtc ccacactggt gactgcgatc ttcagagcag gggtccttgg tgtgaccctc    1800
tgaatggtcc agggttgatc acactctggg tttattacat ggcagtgttc ctatttgggg    1860
cttgcatgcc aaattgtagt tcttgtctga ttggctcacc caagcaaggc caaaattacc    1920
aaaaatcttg gggggttttt actccagtgg tgaagaaaac tcctttagca ggtggtcctg    1980
agacctgaca agcactgcta ggcgagtgcc aggactcccc aggccaggcc accaggatgg    2040
cccttcccac tggaggtcac attcaggaag atgaaagagg aggtttgggg tctgccacca    2100
tcctgctgct gtgttttttgc tatcacacag tgggtggtgg atctgtccaa ggaaacttga    2160
atcaaagcag ttaactttaa gactgagcac ctgcttcatg ctcagccctg actggtgcta    2220
taggctggag aagctcaccc aataaacatt aagattgagg cctgccctca gggatcttgc    2280
attcccagtg gtcaaaccgc actcacccat gtgccaaggt ggggtattta ccacagcagc    2340
tgaacagcca aatgcatggt gcagttgaca gcaggtggga aatggtatga gctgaggggg    2400
gccgtgccca ggggcccaca gggaaccctg cttgcacttt gtaacatgtt tacttttcag    2460
ggcatcttag cttctattat agccacatcc ctttgaaaca agataactga gaatttaaaa    2520
ataagaaaat acataagacc ataacagcca acaggtggca ggaccaggac tatagcccag    2580
gtcctctgat acccagagca ttacgtgagc caggtaatga gggactggaa ccagggagac    2640
cgagcgcttt ctggaaaaga ggagtttcga ggtagagttt gaaggaggtg agggatgtga    2700
attgcctgca gagagaagcc tgttttgttg gaaggtttgg tgtgtggaga tgcagaggta    2760
aaagtgtgag cagtgagtta cagcgagagg cagagaaaga agagacagga gggcaagggc    2820
catgctgaag ggaccttgaa gggtaaagaa gtttgatatt aaaggagtta agagtagcaa    2880
gttctagaga agaggctggt gctgtggcca gggtgagagc tgctctggaa aatgtgaccc    2940
agatcctcac aaccacctaa tcaggctgag gtgtcttaag cctttgctc acaaaacctg    3000
gcacaatggc taattcccag agtgtgaaac ttcctaagta taaatggttg tctgtttttg    3060
taacttaaaa aaaaaaaaaa aagtttggcc gggtgcggtg gctcacgcct gtaatcccag    3120
cactttggga ggccaaggtg ggggatcac aaggtcacta gatggcgagc atcctggcca    3180
acatggtgaa accccgtctc tactaaaaac acaaaagtta gctgagcgtg gtggcgggcg    3240
cctgtagtcc cagccactcg ggaggctgag acaggagaat cgcttaaacc tgggaggcgg    3300
agagtacagt gagccaagat cgcgccactg cactccggcc tgatgacaga gcgagattcc    3360
gtcttaaaaa aaaaaaaaaa aaagtttgtt tttaaaaaaa tctaaataaa ataactttgc    3420
cccctgcaaa aaaaaaaaaa aaaa                                           3444
```

<210> SEQ ID NO 2
<211> LENGTH: 167
<212> TYPE: PRT
<213> ORGANISM: Homo sapiens

<400> SEQUENCE: 2

```
Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60
```

```
Gly Leu His Pro Ile Leu Thr Leu Ser Lys Met Asp Gln Thr Leu Ala
 65                  70                  75                  80

Val Tyr Gln Gln Ile Leu Thr Ser Met Pro Ser Arg Asn Val Ile Gln
                 85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 3
<211> LENGTH: 4969
<212> TYPE: DNA
<213> ORGANISM: Homo sapiens
<220> FEATURE:
<221> NAME/KEY: misc_feature
<222> LOCATION: (4045)..(4144)
<223> OTHER INFORMATION: n is a, c, g, t or u

<400> SEQUENCE: 3
```

| | | | | | |
|---|---|---|---|---|---|
| ctcgagggc | ctagacattg | ccctccagag | agagcaccca | acaccctcca | ggcttgaccg | 60 |
| gccagggtgt | ccccttccta | ccttggagag | agcagcccca | gggcatcctg | caggggtgc | 120 |
| tgggacacca | gctggccttc | aaggtctctg | cctccctcca | gccaccccac | tacacgctgc | 180 |
| tgggatcctg | gatctcagct | ccctggccga | caacactggc | aaaactcctac | tcatccacga | 240 |
| aggccctcct | gggcatggtg | gtccttccca | gcctggcagt | ctgttcctca | cacaccttgt | 300 |
| tagtgcccag | cccctgaggt | tgcagctggg | ggtgtctctg | aagggctgtg | agccccagg | 360 |
| aagccctggg | gaagtgcctg | ccttgcctcc | ccccggccct | gccagcgcct | ggctctgccc | 420 |
| tcctacctgg | gctcccccca | tccagcctcc | ctccctacac | actcctctca | aggaggcacc | 480 |
| catgtcctct | ccagctgccg | ggcctcagag | cactgtggcg | tcctggggca | gccaccgcat | 540 |
| gtcctgctgt | ggcatggctc | agggtggaaa | gggcggaagg | gagggtcct | gcagatagct | 600 |
| ggtgcccact | accaaacccg | ctcggggcag | agagccaaa | ggctgggtgt | gtgcagagcg | 660 |
| gccccgagag | gttccgaggc | tgaggccagg | gtgggacata | gggatgcgag | gggccggggc | 720 |
| acaggatact | ccaacctgcc | tgcccccatg | gtctcatcct | cctgcttctg | ggacctcctg | 780 |
| atcctgcccc | tggtgctaag | aggcaggtaa | ggggctgcag | gcagcagggc | tcggagccca | 840 |
| tgccccctca | ccatgggtca | ggctggacct | ccaggtgcct | gttctgggga | gctgggaggg | 900 |
| ccggaggggt | gtaccccagg | ggctcagccc | agatgacact | atgggggtga | tggtgtcatg | 960 |
| ggacctggcc | aggagagggg | agatgggctc | ccagaagagg | agtgggggct | gagagggtgc | 1020 |
| ctgggggcc | aggacggagc | tgggccagtg | cacagcttcc | cacacctgcc | caccccaga | 1080 |
| gtcctgccgc | caccccaga | tcacacggaa | gatgaggtcc | gagtggcctg | ctgaggactt | 1140 |
| gctgcttgtc | cccaggtccc | caggtcatgc | cctccttctg | ccaccctggg | gagctgaggg | 1200 |
| cctcagctgg | ggctgctgtc | ctaaggcagg | gtgggaacta | ggcagccagc | agggagggga | 1260 |
| cccctccctc | actcccactc | tcccaccccc | accaccttgg | cccatccatg | gcggcatctt | 1320 |
| gggccatccg | ggactgggga | cagggggtcct | ggggacaggg | gtccggggac | agggtcctgg | 1380 |

```
ggacagggt  gtggggacag  gggtctgggg  acagggtgt   ggggacaggg  gtgtggggac  1440
aggggtctgg  ggacagggt   gtggggacag  gggtccgggg  acagggtgt   ggggacaggg  1500
gtctggggac  aggggtgtgg  ggacagggt   gtggggacag  gggtctgggg  acagggtgt   1560
ggggacaggg  gtcctgggga  cagggtgtg   ggacagggg   tgtggggaca  ggggtgtggg  1620
gacagggtg   tggggacagg  ggtcctgggg  ataggggtgt  ggggacaggg  gtgtggggac  1680
aggggtcccg  gggacagggg  tgtggggaca  ggggtgtggg  gacagggtc   ctggggacag  1740
gggtctgagg  acagggtgt   gggcacaggg  gtcctgggga  cagggtcct   ggggacaggg  1800
gtcctgggga  cagggtctg   ggacagcag   cgcaaagagc  cccgccctgc  agcctccagc  1860
tctcctggtc  taatgtggaa  agtggcccag  gtgagggctt  tgctctcctg  gagacatttg  1920
cccccagctg  tgagcaggga  caggtctggc  caccgggccc  ctggttaaga  ctctaatgac  1980
ccgctggtcc  tgaggaagag  gtgctgacga  ccaaggagat  cttcccacag  acccagcacc  2040
agggaaatgg  tccggaaatt  gcagcctcag  cccccagcca  tctgccgacc  cccccacccc  2100
gccctaatgg  gccaggcggc  aggggttgac  aggtagggga  gatgggctct  gagactataa  2160
agccagcgg   ggcccagcag  ccctcagccc  tccaggacag  gctgcatcag  aagaggccat  2220
caagcaggtc  tgttccaagg  gcctttgcgt  caggtgggct  cagggttcca  gggtggctgg  2280
accccaggcc  ccagctctgc  agcagggagg  acgtggctgg  gctcgtgaag  catgtggggg  2340
tgagcccagg  ggcccaagg   cagggcacct  ggccttcagc  ctgcctcagc  cctgcctgtc  2400
tcccagatca  ctgtccttct  gccatggccc  tgtggatgcg  cctcctgccc  ctgctggcgc  2460
tgctggccct  ctggggacct  gacccagccg  cagcctttgt  gaaccaacac  ctgtgcggct  2520
cacacctggt  ggaagctctc  tacctagtgt  gcggggaacg  aggcttcttc  tacacaccca  2580
agacccgccg  ggaggcagag  gacctgcagg  gtgagccaac  cgcccattgc  tgcccctggc  2640
cgccccagc   caccccctgc  tcctggcgct  cccaccagc   atgggcagaa  ggggcagga   2700
ggctgccacc  cagcagggg   tcaggtgcac  ttttttaaaa  agaagttctc  ttggtcacgt  2760
cctaaaagtg  accagctccc  tgtggcccag  tcagaatctc  agcctgagga  cggtgttggc  2820
ttcggcagcc  ccgagataca  tcagagggtg  ggcacgctcc  tccctccact  cgcccctcaa  2880
acaaatgccc  cgcagcccat  ttctccaccc  tcatttgatg  accgcagatt  caagtgtttt  2940
gttaagtaaa  gtcctgggtg  acctgggtc   acagggtgcc  ccacgctgcc  tgcctctggg  3000
cgaacacccc  atcacgcccg  gaggagggcg  tggctgcctg  cctgagtggg  ccagacccct  3060
gtcgccagcc  tcacggcagc  tccatagtca  ggagatgggg  aagatgctgg  ggacaggccc  3120
tggggagaag  tactgggatc  acctgttcag  gctcccactg  tgacgctgcc  ccggggcggg  3180
ggaaggaggt  gggacatgtg  ggcgttgggg  cctgtaggtc  cacacccagt  gtgggtgacc  3240
ctccctctaa  cctgggtcca  gccggctgg   agatgggtgg  gagtgcgacc  tagggctggc  3300
gggcaggcgg  gcactgtgtc  tccctgactg  tgtcctcctg  tgtccctctg  cctcgccgct  3360
gttccggaac  ctgctctgcg  cggcacgtcc  tggcagtggg  gcaggtggag  ctgggcgggg  3420
gccctggtgc  aggcagcctg  cagcccttgg  ccctggaggg  gtccctgcag  aagcgtggca  3480
ttgtggaaca  atgctgtacc  agcatctgct  ccctctacca  gctggagaac  tactgcaact  3540
agacgcagcc  tgcaggcagc  cccacacccg  ccgcctcctg  caccgagaga  gatggaataa  3600
agcccttgaa  ccagccctgc  tgtgccgtct  gtgtgtcttg  ggggccctgg  gccaagcccc  3660
acttcccggc  actgttgtga  gccccctccca  gctctctcca  cgctctctgg  gtgcccacag  3720
```

```
gtgccaacgc cggccaggcc cagcatgcag tggctctccc caaagcggcc atgcctgttg    3780
gctgcctgct gcccccaccc tgtggctcag ggtccagtat gggagcttcg ggggtctctg    3840
aggggccagg gatggtgggg ccactgagaa gtgacttctt gttcagtagc tctggactct    3900
tggagtcccc agagaccttg ttcaggaaag gaatgagaa cattccagca attttccccc     3960
cacctagccc tcccaggttc tattttaga gttatttctg atggagtccc tgtggaggga     4020
ggaggctggg ctgagggagg gggtnnnnnn nnnnnnnnnn nnnnnnnnnn nnnnnnnnnn    4080
nnnnnnnnnn nnnnnnnnnn nnnnnnnnnn nnnnnnnnnn nnnnnnnnnn nnnnnnnnnn    4140
nnnnctcgag ggaggagccc ggggctgggg tacggaggcc tctgcacatc ttagagtaaa    4200
acaagcagga gaggctgggt gcggtggctc atgcctataa tcccagcact ttaggaggct    4260
gaggcgggca gatcacctga ggtcgggagt tcaagaccag cctgaccaac agggagaaac    4320
cccatcttta ctaaaactac aaaattagct gggtgtggtg gcacatgcct gtaatcccag    4380
atattcggga ggctgaggca ggagaatcgc ttgaacctgg gaagcagagg ttgcgctgag    4440
ccgagatggc accattgcac tccagcctgg gcaacgagag cgaaactccg tctcaaaaaa    4500
acaaaaacaa aaaatcaaa acaatcaaaa aaacaagcag gaggggctct gaggtgcctg     4560
caacacccag gtacaatccg tggccctgag gcccatcaca gggaaggggt ctttgcagct    4620
ctttcaaccc ccagcccagc atccaaggaa gcccagggca gggagaaacc tcagctgcac    4680
catcagagct cagaacagag aaggcagaaa ttagcaggga gtggggctgg ggaggcttcc    4740
tagaagacgt gtctcccgcc ttgctggcac tgaggccttg aggatgggtc catactgggc    4800
ccccactgcc agggatgcag atccggccca ctgctgaaat ctgtgctcct ggagcctccc    4860
tcctgttcat gggccacagg ctgtgaaaac cccagagtcc tcccaggcag caagttttgt    4920 tttgttttt gtttgtttgc ttgtttgttt tttgagagtc tgctcgtca              4969
```

<210> SEQ ID NO 4
<211> LENGTH: 110
<212> TYPE: PRT
<213> ORGANISM: Homo sapiens

<400> SEQUENCE: 4

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 5
<211> LENGTH: 767
<212> TYPE: DNA
<213> ORGANISM: Homo sapiens

<400> SEQUENCE: 5

```
gccgccccgc gagaagaaga gcgggaagag gcggacagcg aggccaagat tcagctgcg      60 ggacggtcag gggagacctc caggcgcagg aaggacggc cagggtgaca cggaagcatg     120
cgacggctgc tgatccctct ggccctgtgg ctgggtgcgg tgggcgtggg cgtcgccgag     180
ctcacggaag cccagcgccg gggcctgcag gtggccctgg aggaatttca caagcacccg     240
cccgtgcagt gggccttcca ggagaccagt gtggagagcg ccgtggacac gcccttccca     300
gctggaatat ttgtgaggct ggaatttaag ctgcagcaga caagctgccg gaagagggac     360
tggaagaaac ccgagtgcaa agtcaggccc aatggggaga aacggaaatg cctggcctgc     420
atcaaactgg gctctgagga caaagttctg ggccggttgg tccactgccc catagagacc     480
caagttctgc gggaggctga ggagcaccag gagacccagt gcctcagggt gcagcgggct     540
ggtgaggacc cccacagctt ctacttccct ggacagttcg ccttctccaa ggccctgccc     600
cgcagctaag ccagcactga gatgcgtggt gcctccagga ccgctgcggg tggtaaccag     660
tggaagaccc cagcccccag ggagaggaac ccgttctatc cccagccatg ataataaagc     720
tgctctccca gctgcctctc aaaaaaaaaa aaaaaaaaa aaaaaa                    767
```

<210> SEQ ID NO 6
<211> LENGTH: 163
<212> TYPE: PRT
<213> ORGANISM: Homo sapiens

<400> SEQUENCE: 6

```
Met Arg Arg Leu Leu Ile Pro Leu Ala Leu Trp Leu Gly Ala Val Gly
1               5                   10                  15

Val Gly Val Ala Glu Leu Thr Glu Ala Gln Arg Arg Gly Leu Gln Val
            20                  25                  30

Ala Leu Glu Glu Phe His Lys His Pro Pro Val Gln Trp Ala Phe Gln
        35                  40                  45

Glu Thr Ser Val Glu Ser Ala Val Asp Thr Pro Phe Pro Ala Gly Ile
    50                  55                  60

Phe Val Arg Leu Glu Phe Lys Leu Gln Gln Thr Ser Cys Arg Lys Arg
65                  70                  75                  80

Asp Trp Lys Lys Pro Glu Cys Lys Val Arg Pro Asn Gly Arg Lys Arg
                85                  90                  95

Lys Cys Leu Ala Cys Ile Lys Leu Gly Ser Glu Asp Lys Val Leu Gly
            100                 105                 110

Arg Leu Val His Cys Pro Ile Glu Thr Gln Val Leu Arg Glu Ala Glu
        115                 120                 125

Glu His Gln Glu Thr Gln Cys Leu Arg Val Gln Arg Ala Gly Glu Asp
    130                 135                 140

Pro His Ser Phe Tyr Phe Pro Gly Gln Phe Ala Phe Ser Lys Ala Leu
145                 150                 155                 160

Pro Arg Ser
```

<210> SEQ ID NO 7
<211> LENGTH: 7415
<212> TYPE: DNA
<213> ORGANISM: Homo sapiens

<400> SEQUENCE: 7

```
gaaggcaaat gttcccccag ctgtttcctg tctacagtgt ctgtgttttg tagataaatg      60
tgaggatttt ctctaaatcc ctcttctgtt tgctaaatct cactgtcact gctaaattca     120
gagcagatag agcctgcgca atggaataaa gtcctcaaaa ttgaaatgtg acattgctct     180
```

```
caacatctcc catctctctg gatttctttt tgcttcatta ttcctgctaa ccaattcatt      240
ttcagacttt gtacttcaga agcaatggga aaaatcagca gtcttccaac ccaattattt      300
aagtgctgct tttgtgattt cttgaaggtg aagatgcaca ccatgtcctc ctcgcatctc      360
ttctacctgg cgctgtgcct gctcaccttc accagctctg ccacggctgg accggagacg      420
ctctgcgggg ctgagctggt ggatgctctt cagttcgtgt gtggagacag gggcttttat      480
ttcaacaagc ccacagggta tggctccagc agtcggaggg cgcctcagac aggcatcgtg      540
gatgagtgct gcttccggag ctgtgatcta aggaggctgg agatgtattg cgcacccctc      600
aagcctgcca gtcagctcg ctctgtccgt gcccagcgcc acaccgacat gcccaagacc      660
cagaagtatc agcccccatc taccaacaag aacacgaagt ctcagagaag gaaaggaagt      720
acatttgaag aacgcaagta gagggagtgc aggaaacaag aactacagga tgtaggaaga      780
ccctcctgag gagtgaagag tgacatgcca ccgcaggatc ctttgctctg cacgagttac      840
ctgttaaact ttggaacacc taccaaaaaa taagtttgat aacatttaaa agatgggcgt      900
ttcccccaat gaaatacaca agtaaacatt ccaacattgt ctttaggagt gatttgcacc      960
ttgcaaaaat ggtcctggag ttggtagatt gctgttgatc ttttatcaat aatgttctat     1020
agaaaagaaa aaaaaaatat atatatatat atatcttagt ccctgcctct caagagccac     1080
aaatgcatgg gtgttgtata gatccagttg cactaaattc ctctctgaat cttggctgct     1140
ggagccattc attcagcaac cttgtctaag tggtttatga attgtttcct tatttgcact     1200
tctttctaca caactcgggc tgtttgtttt acagtgtctg ataatcttgt tagtctatac     1260
ccaccacctc ccttcataac ctttatattt gccgaatttg gcctcctcaa aagcagcagc     1320
aagtcgtcaa gaagcacacc aattctaacc cacaagattc catctgtggc atttgtacca     1380
aatataagtt ggatgcattt tattttagac acaaagcttt attttttccac atcatgctta     1440 caaaaaagaa taatgcaaat agttgcaact ttgaggccaa tcattttag gcatatgttt     1500 taaacataga aagtttcttc aactcaaaag agttccttca aatgatgagt taatgtgcaa     1560
cctaattagt aactttcctc ttttatttt ttccatatag agcactatgt aaatttagca     1620
tatcaattat acaggatata tcaaacagta tgtaaaactc tgttttttag tataatggtg     1680 ctatttgta gtttgttata tgaaagagtc tggccaaaac ggtaatacgt gaaagcaaaa     1740 caataggga agcctggagc caaagatgac acaaggggaa gggtactgaa acaccatcc     1800 atttgggaaa gaaggcaaag tcccccagt tatgccttcc aagaggaact tcagacacaa     1860
aagtccactg atgcaaattg gactggcgag tccagagagg aaactgtgga atggaaaaag     1920
cagaaggcta ggaatttag cagtcctggt ttcttttct catggaagaa atgaacatct     1980
gccagctgtg tcatggactc accactgtgt gaccttgggc aagtcacttc acctctctgt     2040
gcctcagttt cctcatctgc aaaatggggg caatatgtca tctacctacc tcaaaggggt     2100
ggtataaggt ttaaaaagat aaagattcag attttttta ccctgggttg ctgtaagggt     2160
gcaacatcag ggcgcttgag ttgctgagat gcaaggaatt ctataaataa cccattcata     2220
gcatagctag agattggtga attgaatgct cctgacatct cagttcttgt cagtgaagct     2280
atccaaataa ctgccaact agttgttaaa agctaacagc tcaatctctt aaaacacttt     2340
tcaaaatatg tgggaagcat ttgattttca atttgatttt gaattctgca tttggtttta     2400
tgaatacaaa gataagtgaa aagagagaaa ggaaagaaaa aaggagaaaa acaaagagat     2460
ttctaccagt gaaaggggaa ttaattactc tttgttagca ctcactgact cttctatgca     2520
```

-continued

```
gttactacat atctagtaaa acctcgttta atactataaa taatattcta ttcattttga    2580
aaaacacaat gattccttct tttctaggca atataaggaa agtgatccaa aatttgaaat    2640
attaaaataa tatctaataa aaagtcacaa agttatcttc tttaacaaac tttactctta    2700
ttcttagctg tatatacatt ttttttaaaag tttgttaaaa tatgcttgac tagagttttcc   2760 agttgaaagg caaaaacttc catcacaaca agaaatttcc catgcctgct cagaagggta    2820 gccctagct ctctgtgaat gtgttttatc cattcaactg aaaattggta tcaagaaagt    2880
ccactggtta gtgtactagt ccatcatagc ctagaaaatg atccctatct gcagatcaag    2940
attttctcat tagaacaatg aattatccag cattcagatc tttctagtca ccttagaact    3000
ttttggttaa aagtacccag gcttgattat ttcatgcaaa ttctatattt tacattcttg    3060
gaaagtctat atgaaaaaca aaaataacat cttcagtttt tctcccactg ggtcacctca    3120
aggatcagag gccaggaaaa aaaaaaaaaa gactccctgg atctctgaat atatgcaaaa    3180
agaaggcccc atttagtgga gccagcaatc ctgttcagtc aacaagtatt ttaactctca    3240
gtccaacatt atttgaattg agcacctcaa gcatgcttag caatgttcta atcactatgg    3300
acagatgtaa aagaaactat acatcatttt tgccctctgc ctgttttcca gacatacagg    3360
ttctgtggaa taagatactg gactcctctt cccaagatgg cacttctttt tatttcttgt    3420
ccccagtgtg taccttttaa aattattccc tctcaacaaa actttatagg cagtcttctg    3480
cagacttaac gtgttttctg tcatagttag atgtgataat tctaagagtg tctatgactt    3540
atttccttca cttaattcta tccacagtca aaaatccccc aaggaggaaa gctgaaagat    3600
gcactgccat attatctttc ttaacttttt ccaacacata atcctctcca actggattat    3660
aaataaattg aaaataactc attataccaa ttcactattt tattttttaa tgaattaaaa    3720
ctagaaaaca aattgatgca aaccctggaa gtcagttgat tactatatac tacagcagaa    3780
tgactcagat ttcatagaaa ggagcaacca aaatgtcaca acccaaaact ttacaagctt    3840
tgcttcagaa ttagattgct ttataattct tgaatgaggc aatttcaaga tatttgtaaa    3900
agaacagtaa acattggtaa gaatgagctt tcaactcata ggcttatttc caatttaatt    3960
gaccatactg gatacttagg tcaaatttct gttctctctt ccccaaataa tattaaagta    4020
ttatttgaac tttttaagat gaggcagttc ccctgaaaaa gttaatgcag ctctccatca    4080
gaatccactc ttctagggat atgaaaaatct cttaacaccc accctacata cacagacaca    4140
cacacacaca cacacacaca cacacacaca cacattcacc ctaaggatcc aatggaatac    4200 tgaaagaaa tcacttcctt gaaaatttta ttaaaaaaca aacaaacaaa caaaaagcct    4260
gtccacccct gagaatcctt cctctccttg gaacgtcaat gtttgtgtag atgaaaccat    4320
ctcatgctct gtggctccag ggtttctgtt actattttat gcacttggga gaaggcttag    4380
aataaaagat gtagcacatt ttgctttccc atttattgtt tggccagcta tgccaatgtg    4440
gtgctattgt ttctttaaga aagtacttga ctaaaaaaaa aagaaaaaaa gaaaaaaag    4500 aaagcataga catatttttt taaagtataa aaacaacaat tctatagata gatggcttaa    4560
taaaatagca ttaggtctat ctagccacca ccacctttca acttttatc actcacaagt    4620 agtgtactgt tcaccaaatt gtgaatttgg gggtgcaggg gcaggagttg gaaattttt    4680 aaagttagaa ggctccattg ttttgttggc tctcaaactt agcaaaatta gcaatatatt    4740
atccaatctt ctgaacttga tcaagagcat ggagaataaa cgcgggaaaa aagatccttat    4800 aggcaaaatag aagaatttaa aagataagta agttccttat tgattttttgt gcactctgct    4860 ctaaaacaga tattcagcaa gtggagaaaa taagaacaaa gagaaaaaat acatagattt    4920
```

```
acctgcaaaa aatagcttct gccaaatccc ccttgggtat tctttggcat ttactggttt     4980
atagaagaca ttctcccttc acccagacat ctcaaagagc agtagctctc atgaaaagca     5040
atcactgatc tcatttggga aatgttggaa agtatttcct tatgagatgg gggttatcta     5100
ctgataaaga aagaatttat gagaaattgt tgaaagagat ggctaacaat ctgtgaagat     5160
tttttgtttc ttgttttttgt tttttttttt ttttttacttt atacagtctt tatgaatttc     5220
ttaatgttca aaatgacttg gttcttttct tcttttttta tatcagaatg aggaataata     5280
agttaaaccc acatagactc tttaaaacta taggctagat agaaatgtat gtttgacttg     5340
ttgaagctat aatcagacta tttaaaatgt tttgctattt ttaatcttaa aagattgtgc     5400
taatttatta gagcagaacc tgtttggctc tcctcagaag aaagaatctt tccattcaaa     5460
tcacatggct ttccaccaat attttcaaaa gataaatctg attatgcaa tggcatcatt      5520
tattttaaaa cagaagaatt gtgaaagttt atgcccctcc cttgcaaaga ccataaagtc     5580
cagatctggt agggggggcaa caacaaaagg aaaatgttgt tgattcttgg ttttggattt    5640
tgttttgttt tcaatgctag tgtttaatcc tgtagtacat atttgcttat tgctatttta    5700
atattttata agaccttcct gttaggtatt agaaagtgat acatagatat ctttttttgtg   5760
taatttctat ttaaaaaaga gagaagactg tcagaagctt taagtgcata tggtacagga    5820
taaagatatc aatttaaata accaattcct atctggaaca atgcttttgt tttttaaaga    5880
aacctctcac agataagaca gaggcccagg ggattttga agctgtcttt attctgcccc      5940
catcccaacc cagcccttat tattttagta tctgcctcag aattttatag agggctgacc     6000
aagctgaaac tctagaatta aaggaacctc actgaaaaca tatatttcac gtgttccctc     6060
tttttttttt tccttttttgt gagatggggt ctcgcactgt cccccaggct ggagtgcagt    6120
ggcatgatct cggctcactg caacctccac ctcctgggtt taagcgattc tcctgcctca    6180
gcctcctgag tagctgggat tacaggcacc caccactatg cccggctaat ttttttggatt   6240
tttaatagag acggggtttt accatgttgg ccaggttggt ctcaaactcc tgaccttgtg    6300
atttgcccgc ctcagcctcc caaattgctg ggattacagg catgagccac cacaccctgc    6360
ccatgtgttc cctcttaatg tatgattaca tggatcttaa acatgatcct tctctcctca    6420
ttcttcaact atctttgatg gggtcttttca aggggaaaaa aatccaagct ttttttaaagt  6480
aaaaaaaaaa aaagagagga cacaaaacca aatgttactg ctcaactgaa atatgagtta    6540
agatggagac agagtttctc ctaataaccg gagctgaatt accttttcact ttcaaaaaca   6600
tgaccttcca caatccttag aatctgcctt ttttttatatt actgaggcct aaaagtaaac   6660
attactcatt ttattttgcc caaaatgcac tgatgtaaag taggaaaaat aaaaacagag    6720
ctctaaaatc cctttcaagc cacccattga ccccactcac caactcatag caaagtcact   6780
tctgttaatc ccttaatctg attttgtttg gatatttatc ttgtacccgc tgctaaacac    6840
actgcaggag ggactctgaa acctcaagct gtctacttac atcttttatc tgtgtctgtg    6900
tatcatgaaa atgtctattc aaaatatcaa aacctttcaa atatcacgca gcttatattc    6960
agtttacata aaggcccaa ataccatgtc agatctttt ggtaaaagag ttaatgaact       7020
atgagaattg ggattacatc atgtatttttg cctcatgtat tttatcaca cttataggcc     7080
aagtgtgata aataaactta cagacactga attaatttcc cctgctactt tgaaaccaga    7140
aaataatgac tggccattcg ttacatctgt cttagttgaa aagcatattt tttattaaat    7200
taattctgat tgtatttgaa attattattc aattcactta tggcagagga atatcaatcc   7260
```

```
                                        -continued taatgacttc taaaaatgta actaattgaa tcattatctt acatttactg tttaataagc    7320
atattttgaa aatgtatggc tagagtgtca taataaaatg gtatatcttt ctttagtaat    7380
tacattaaaa ttagtcatgt ttgattaatt agttc                              7415

<210> SEQ ID NO 8
<211> LENGTH: 158
<212> TYPE: PRT
<213> ORGANISM: Homo sapiens

<400> SEQUENCE: 8

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
                100                 105                 110

Lys Pro Ala Lys Ser Ala Arg Ser Val Arg Ala Gln Arg His Thr Asp
            115                 120                 125

Met Pro Lys Thr Gln Lys Tyr Gln Pro Pro Ser Thr Asn Lys Asn Thr
        130                 135                 140

Lys Ser Gln Arg Arg Lys Gly Ser Thr Phe Glu Glu Arg Lys
145                 150                 155
```